(12) United States Patent
Zarkadas et al.

(10) Patent No.: US 8,420,122 B2
(45) Date of Patent: Apr. 16, 2013

(54) PROCESS FOR THE PRECIPITATION AND ISOLATION OF 6,6-DIMETHYL-3-AZA-BICYCLO [3.1.0] HEXANE-AMIDE COMPOUNDS BY CONTROLLED PRECIPITATION AND PHARMACEUTICAL FORMULATIONS CONTAINING SAME

(75) Inventors: Dimitrios Zarkadas, Fanwood, NJ (US); Vincenzo Liotta, Glen Ridge, NJ (US); Christopher Stanley Pridgen, Union City, NJ (US); Wing-Kee Philip Cho, Princeton, NJ (US); Zhihui Qiu, Bridgewater, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 919 days.

(21) Appl. No.: 12/080,989

(22) Filed: Apr. 8, 2008

(65) Prior Publication Data

US 2008/0254128 A1 Oct. 16, 2008

Related U.S. Application Data

(63) Continuation-in-part of application No. 11/789,915, filed on Apr. 26, 2007, now abandoned.

(60) Provisional application No. 60/795,753, filed on Apr. 28, 2006, provisional application No. 60/796,717, filed on May 2, 2006, provisional application No. 60/796,490, filed on May 1, 2006, provisional application No. 60/873, 877, filed on Dec. 7, 2006.

(51) Int. Cl.
*A61K 9/16* (2006.01)
*A61K 31/403* (2006.01)
*C07D 209/52* (2006.01)

(52) U.S. Cl.
USPC ............................ 424/489; 514/412; 548/515

(58) Field of Classification Search ........................ None
See application file for complete search history.

(56) References Cited

U.S. PATENT DOCUMENTS

| 5,133,908 | A | 7/1992 | Stainmesse et al. |
| 5,314,506 | A | 5/1994 | Midler, Jr. et al. |
| 5,389,263 | A | 2/1995 | Gallagher et al. |
| 6,558,435 | B2 | 5/2003 | Am Ende et al. |
| 7,012,066 | B2 * | 3/2006 | Saksena et al. ................. 514/1.3 |
| 2003/0049323 | A1 * | 3/2003 | Hitt et al. ........................ 424/489 |
| 2003/0216325 | A1 | 11/2003 | Saksena et al. |
| 2005/0249702 | A1 | 11/2005 | Njoroge et al. |
| 2006/0255323 | A1 | 11/2006 | Seki et al. |
| 2009/0264425 | A1 * | 10/2009 | Jones et al. ................. 514/235.2 |

FOREIGN PATENT DOCUMENTS

| JP | 11 171700 A | 6/1999 |
| JP | 2004 223451 A | 8/2004 |
| WO | WO 02/00198 A1 | 1/2002 |
| WO | WO 2002/008244 A2 | 1/2002 |
| WO | WO 03/008082 A1 | 1/2003 |
| WO | WO 03/080034 A2 | 10/2003 |
| WO | WO 2005/032511 A2 | 4/2005 |
| WO | WO 2005/041970 A1 | 5/2005 |
| WO | WO 2005/107745 A1 | 11/2005 |
| WO | WO 2006/009441 A2 | 1/2006 |
| WO | WO 2006/130628 A2 | 12/2006 |

OTHER PUBLICATIONS

International Search Report for international Application No. PCT/US2007/010255 filed Apr. 26, 2007; mail date Apr. 1, 2008; 2 pages; published as WO2007/127380 on May 22, 2007 with Search Report (copy enclosed).

* cited by examiner

*Primary Examiner* — Suzanne Ziska
(74) *Attorney, Agent, or Firm* — Julie M. Lake; Sheldon O. Heber

(57) ABSTRACT

The present invention provides a method of continuous precipitation and isolation of an amorphous solid particulate form of 3-[2-(3-tert-Butyl-ureido)-3,3-dimethyl-butyryl]-6,6-dimethyl-3-aza-bicyclo[3.1.0]hexane-2-carboxylic acid (2-carbamoyl-1-cyclobutylmethyl-2-oxo-ethyl)-amide having controlled physical properties. The present invention provides also pharmaceutical formulations comprising the precipitated compound.

4 Claims, 7 Drawing Sheets

7a        7b

PROCESS FOR THE PRECIPITATION AND ISOLATION OF 6,6-DIMETHYL-3-AZA-BICYCLO [3.1.0] HEXANE-AMIDE COMPOUNDS BY CONTROLLED PRECIPITATION AND PHARMACEUTICAL FORMULATIONS CONTAINING SAME

CROSS-REFERENCE TO RELATED APPLICATIONS

The present application is a continuation-in-part of U.S. Ser. No. 11/789,915, filed Apr. 26, 2007, which in turn is based on and claims the priority of each of U.S. Provisional Application Nos. 60/795,753 filed Apr. 28, 2006, 60/796,717 filed May 2, 2006, 60/796,490 filed May 1, 2006, and 60/873,877 filed Dec. 7, 2006, each of which is incorporated herein by reference in its entirety.

FIELD OF THE INVENTION

The present invention is directed to a process for precipitation and isolation of compounds having therapeutic properties, more particularly, precipitation and isolation of 3-[2-(3-tert-Butyl-ureido)-3,3-dimethyl-butyryl]-6,6-dimethyl-3-aza-bicyclo[3.1.0]hexane-2-carboxylic acid (2-carbamoyl-1-cyclobutylmethyl-2-oxo-ethyl)-amide and granular pharmaceutical formulations containing the same.

BACKGROUND OF THE INVENTION

Identification of any publication in this section or any section of this application is not an admission that such publication is prior art to the present invention.

One method of providing a pharmaceutical compound in a solid form is to precipitate the compound from a solution by combining an anti-solvent and a solution of a compound to be precipitated (solvent/anti-solvent precipitation processes). Generally, when preparing a precipitate using solvent/anti-solvent precipitation processes, the characteristics of the precipitated material show increasing sensitivity to the presence of concentration gradients created during solution and anti-solvent mixing with increasing rapidity of particle formation upon combining the solution and anti-solvent. Examples of the precipitated product characteristics which can be affected by the presence of concentration gradients in a solvent/anti-solvent precipitation process include the range of primary particle sizes provided by the precipitation process, the size, bulk surface area, and bulk density of precipitated particles (agglomerates of primary particles), and the amount of solvent included in the precipitated particles.

Solvent/anti-solvent precipitation processes are typically carried out in a batch process. In general, batch processes are run by introducing, at a slow rate under mixing conditions, small aliquots of a solution of the compound to be precipitated into a tank containing the anti-solvent. It is common in batch processes of this type for the mixing shear in the anti-solvent tank to be insufficient to provide mixing of the anti-solvent and the solution that is sufficiently free from concentration gradients that the process provides particles of consistent and controlled size range with low solvent inclusion.

Solvent/anti-solvent precipitation processes in which nucleation rate is on the same order of magnitude as, or faster than, the rate of mixing are said to be mixing-controlled processes. In mixing-controlled processes for producing precipitated particle materials some workers have adopted methods which include high-velocity impinging of substantially opposed streams of solvent and anti-solvent to provide better control of particle size range and maintain low solvent inclusion in the precipitated material, see for example U.S. Pat. No. 5,314,506 to Midler et al. (the '506 patent), and U.S. Pat. No. 6,558,435 to Am-Ende et al., each of which teaches producing crystals of controlled size by utilizing substantially diametrically opposed impinging jets of solution and anti-solvent to produce high-intensity micromixing and precipitate crystals of the dissolved compound. U.S. Pat. No. 6,302,958 to Lindrud et al., teaches utilizing the impinging streams as taught in the '506 patent and in addition utilizing an ultrasonic probe placed in the zone of impingement to increase the mixing rate to a point at which the rate of homogenization of the admixed liquids is on a time scale smaller than the crystal nucleation time within the mixing zone. Each of these solutions to mixing controlled precipitation requires the use of precise mechanisms and relies on precise control of fluid dynamics to control the physical aspects of the crystalline solids precipitated.

U.S. Pat. No. 7,012,066 to Saskena, et al. (the '066 patent) describes 6,6-dimethyl-3-aza-bicyclo[3.1.0]-hexane-amide compounds of Formula A,

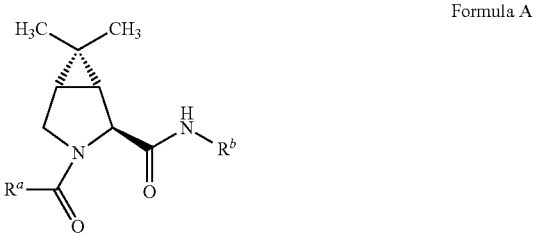

Formula A wherein $R^a$ represents the moieties described in the '066 patent as $R_3$, Z, $R_4$, W and Y, and $R^b$ represents the moieties described in the '066 patent as methylene substituted by $R_1$ and $R_2$. One specific example of the compounds described in the '066 patent is 3-[2-(3-tert-Butyl-ureido)-3,3-dimethyl-butyryl]-6,6-dimethyl-3-aza-bicyclo[3.1.0]hexane-2-carboxylic acid (2-carbamoyl-1-cyclobutylmethyl-2-oxo-ethyl)-amide (the compound of Formula B, see the '066 patent at col. 113, Example XXIV (cols. 448 to 451) and col. 1259). These compounds have desirable properties as hepatitis C virus (HCV) protease inhibitors in the treatment of HCV infections.

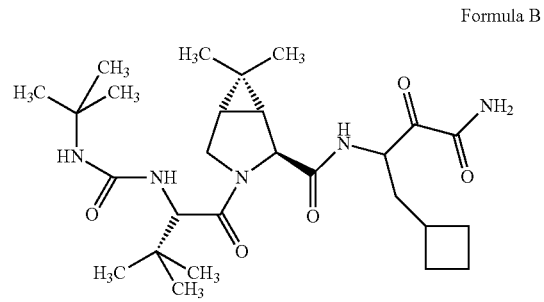

Formula B

When incorporating such compounds into a medicament for the treatment or prevention of conditions amenable to HCV protease inhibitor therapy, it is desirable to provide an active compound used in a pharmaceutical formulation (API), for example, a compound of Formulae A or B, in a highly pure form which has consistent physical properties, for example, in the form of an agglomerated particulate material having an average size in the micron range, with a narrow particulate size distribution, consistent bulk density, low amounts of included solvent, and a sharply defined melting point. It is preferable if a compound can be crystallized as the dynamics of crystallization can be employed to insure high purity and utilized to insure uniform physical properties. Attempts to provide the compound of Formula B in a crystalline form have not met with success.

In the provision of compounds suitable for pharmaceutical use it is common practice to purify and isolate pharmaceutically active compounds by precipitating the solid compound from a solution of the compound. One common precipitation method, termed herein "the solution/anti-solvent method", is carried out by mixing a solution of the desired compound into a sufficient amount of an anti-solvent to provide a solvent/anti-solvent mixture in which the desired compound has reduced solubility. Accordingly, upon mixing a solution of the desired compound and an anti-solvent, the desired compound forms primary particles which aggregate and precipitate from the combined liquids forming a slurry comprising precipitated particles and the combined solvent and anti-solvent liquid.

When the solvent/anti-solvent method is applied to the provision of the compound of Formula B in a batch crystallizer, there is precipitated an amorphous, particulate material which has highly varied primary particle size and a wide range in size of agglomerates, necessitating secondary classification of the particulate material produced from the precipitation process. Moreover, the precipitation product of the compound of Formula B provided from a batch crystallizer by the solution/anti-solvent method yields a precipitated material which retains a widely varied amount of solvent, batch to batch, and often provides a product which either requires a prolonged drying time to drive off the excess included solvent or has the form of a gum rather than a particle form, and accordingly is unusable.

OBJECTIVES AND SUMMARY OF THE INVENTION

In view of the foregoing, what is needed is a method of providing a compound of Formula A, for example, 3-[2-(3-tert-Butyl-ureido)-3,3-dimethyl-butyryl]-6,6-dimethyl-3-aza-bicyclo[3.1.0]hexane-2-carboxylic acid (2-carbamoyl-1-cyclobutylmethyl-2-oxo-ethyl)-amide, the compound of Formula B, in a solid, high purity, precipitated particle form and/or agglomerated particulate form, the method consistently yielding solids having a narrow size range, for example, particle sizes of from about 200 nm to about 300 nm, a narrow chord length range for agglomerated particulate and precipitated particles, and in addition provides the desired level of control over the quantity of included solvent. These and other objectives and/or advantages are provided by the present invention.

Accordingly, in one aspect of the present invention there is disclosed a method of precipitating a compound of Formula A, for example, 3-[2-(3-tert-Butyl-ureido)-3,3-dimethyl-butyryl]-6,6-dimethyl-3-aza-bicyclo[3.1.0]hexane-2-carboxylic acid (2-carbamoyl-1-cyclobutylmethyl-2-oxo-ethyl)-amide (the compound of Formula B) in an amorphous, solid particulate form comprising primary particles within a size range of from about 200 nm to about 300 nm, the method comprising introducing a stream of a solution of the compound of Formula B into a stream of an anti-solvent for the compound of Formula B under controlled turbulent flow conditions. In some embodiments it is preferred to maintain the Reynolds number (Re) of the solution stream at a value which is at least sufficient to provide turbulent flow, for example, a value of at least about 2,000, more preferably a value of at least about 5,500, more preferably at value of at least about 10,000. In some embodiments it is preferred to maintain the Reynolds number of the anti-solvent stream at a value of at least about 9,000, preferably at a value of at least about 15,000, more preferably at a value of at least about 20,000. In some embodiments it is preferred to combine the streams absent any co-current component. In some embodiments it is preferred to combine solvent stream with an anti-solvent stream at an angle substantially 90 degrees with respect to the anti-solvent stream. In some embodiments it is preferred to combine the streams absent any stream impinging component.

In some embodiments the inventive method comprises utilizing a stream of a solution of Formula B wherein the Reynolds number of the solution stream is maintained at a value of at least about 5,500, and the volumetric ratio of the stream of solvent and the stream of anti-solvent is from about 1:15 to about 1:3 solution:anti-solvent, preferably about 1:4 solution:anti-solvent.

In some embodiments it is preferred to maintain the region of the equipment in which contact between the solution and anti-solvent occurs at a temperature of from about −25° C. to about +25° C., preferably from about −25° C. to about +20° C. Preferably, region of the equipment wherein contact between the solution and the anti-solvent occurs is maintained at a temperature of about −15° C. In some embodiments it is preferred to maintain the anti-solvent at a temperature of from about −25° C. to about +20° C., preferably at a temperature of about −20° C. In some embodiments it is preferred to maintain the solution of the compound of Formula B at a temperature of from about −10° C. to about +20° C., preferably at a temperature of about 0° C. In some embodiments the anti-solvent and solution are cooled to the desired temperature and the region of the equipment in which the solution and anti-solvent are combined, for example, a mixing Tee, is operated at ambient temperature.

In some embodiments preferably the solution of the compound of Formula B comprises methyl-tertiarybutyl-ether (MTBE) as a solvent. In some embodiments preferably the solution contains an amount of the compound of Formula B providing a solution having from about 80 mg/ml (0.15 M) to about 250 mg/ml (0.48 M) of the compound of Formula B, preferably from about 166 mg/ml to about 200 mg/ml of the compound of Formula B, more preferably about 166 mg/ml of the compound of Formula B. In some embodiments it is preferred for the solvent to be selected from methyl-tertiarybutyl-ether (MTBE) and a mixture of ethylacetate and MTBE. In some embodiments preferably the anti-solvent is n-heptane. In some embodiments it is preferred to substantially remove water from the solution prior to precipitation, for example, by drying the solution with a drying agent, distillation, or CUNO filtration. In some embodiments the solvent is acetone and the anti-solvent is water.

In some embodiments it is preferred to carry out the precipitation process by utilizing a continuously blended stream of solution and anti-solvent, forming a slurry of solvent, anti-solvent and precipitated particles (initial slurry). In some embodiments it is preferred to conduct the initial slurry from the region where the solution and anti-solvent are combined to a holding tank in which the initial slurry is collected. In some embodiments, optionally, a static mixer is disposed in the conduit between the blending region and holding tank through which the slurry is conducted. In some processes utilizing a continuously blended stream of solution and anti-solvent it is preferred to collect the precipitated solids by one or more techniques selected from decantation, filtration and centrifugation.

In some embodiments it is preferred to collect the slurry formed by combining streams of solution and antisolvent in a holding tank, and additionally carry out a distillation step on the collected slurry.

In some embodiments it is preferred to remove an amount of liquid that provides a residual slurry having a volume which is from about 90 vol. % to about 25 vol % of the initial slurry volume, more preferably to provide a volume of from about 90 vol. % to about 30 vol. % of the initial slurry volume, more preferably to provide a slurry volume which is about one third of the initial slurry volume.

In some embodiments the distillation step is carried out in a controlled pressure/temperature distillation regime to facilitate reproducible agglomeration of the precipitated solids (precipitated particles), thereby forming an agglomerated particulate of controlled chord length, bulk surface area, and bulk density. In some embodiments it is preferred to perform the distillation step under reduced atmosphere conditions, preferably under pressure conditions of greater than about −0.97 Bar gage (barg), at a temperature of less than about 32° C. In some embodiments it is preferred to distill off from about 18 vol % to about 22 vol % of the initial slurry volume at a temperature of less than about 30° C. In some embodiments it is preferred to distill off the first 10 vol % of the initial slurry volume at a temperature of less than about 26° C. In some embodiments it is preferred to distill off the first 8 vol % of the initial slurry volume at a temperature of less than about 25° C. In some embodiments it is preferred to distill off the first 6 vol % of the initial slurry volume at a temperature of less than about 23° C. In some embodiments it is preferred to distill off the first 4 vol % of the initial slurry volume at a temperature of less than about 22° C. In some embodiments it is preferred to distill off the first 2 vol. % of the initial slurry volume at a temperature of less than about 21° C.

In some embodiments, following concentration of the initial slurry, the process further comprises isolating the agglomerated particulate by filtration followed by washing the filter cake with aliquots of anti-solvent. In some embodiments it is preferred to wash the filter cake with n-heptane, equal in volume to about 4 times the volume of the filter cake. In some embodiments it is preferred to wash the filter cake with a mass of anti-solvent equal to the mass of the filter cake. In some embodiments it is preferred to wash the filter cake with 2 aliquots of antisolvent equal in mass of the filter cake. In some embodiments it is preferred to wash the filter cake with anti-solvent until the residual solvent level in the filter cake is less than from about 1 to about 1.5 wt. %.

In some embodiments, after washing the filter cake the process further comprises drying the isolated agglomerated particulate in the ambient environment at a temperature of from about 25° C. to about 45° C. for a period sufficient to reduce the total residual solvent to a value of less than about 1.0 wt. %, preferably less than about 0.8 wt. %.

In some embodiments it is preferred that the concentration of 3-[2-(3-tert-Butyl-ureido)-3,3-dimethyl-butyryl]-6,6-dimethyl-3-aza-bicyclo[3.1.0]hexane-2-carboxylic acid (2-carbamoyl-1-cyclobutylmethyl-2-oxo-ethyl)-amide (the compound of Formula B), the volumetric ratio of the stream of solution and anti-solvent, and the linear velocity of the combining streams are selected to produce a precipitate of the compound of Formula B having a primary particle of less than about 1.0 micron, a median precipitated particle size (aggregation of primary particles) of from about 1 micron to about 2.5 microns, preferably about 1.5 microns, a precipitated particle size distribution of from about 1 micron to about 50 microns and a level of included solvent of less than about 1 wt. %. In some embodiments it is preferred to select process conditions producing precipitated particles in the initial slurry having a bulk surface area of from about 16 $m^2/g$ to about 33 $m^2/g$, preferably from about 25 $m^2/g$ to about 32.5 $m^2/g$. In some embodiments it is preferred to select process conditions providing a slurry wherein the solids in the slurry have a softening point of from about 20° C. to about 50° C., preferably from about 25° C. to about 50° C. In some embodiments it is preferred to carry out a distillation step on the initially collected slurry under conditions yielding an agglomerated particulate having a bulk surface area range of from about 5 $m^2/g$ to about 12 $m^2/g$. In some embodiments it is preferred to select distillation step conditions yielding an agglomerated particulate having a median bulk surface area of about 7 $m^2/g$.

Another aspect of the present invention is the provision of a pharmaceutical formulation having a bulk density of from about 0.4 mg/ml to about 0.6 mg/ml, preferably a bulk density of about 0.47 mg/ml and a tapped density of about 0.64 mg/ml, and comprising the an agglomerated particulate prepared in accordance with the present invention. In some embodiments it is preferred for the granular pharmaceutical formulation to comprise up to 50 wt. % API comprising the compound of Formula B prepared in accordance with the process of the invention, preferably 50 wt. % API, up to 14 wt. % lactose monohydrate, preferably 14 wt. % lactose monohydrate, up to 6 wt % croscarmellose sodium, preferably 6 wt. % croscarmellose sodium, up to 10 wt. % microcrystalline cellulose, preferably 10 wt. % microcrystalline cellulose, up to 15 wt. % pregelatinized starch, preferably 15 wt. % pregelatinized starch, up to 6 wt. % sodium lauryl sulfate, preferably 3 wt. % sodium lauryl sulfate, and up to 2 wt. % magnesium stearate, preferably 2 wt. % magnesium stearate.

In some embodiments it is preferred to prepare a granular pharmaceutical formulation by a process comprising:
  (a) forming a first granulate by a process comprising:
    (i) blending an amount of the compound of Formula B prepared in accordance with the process of the invention (API) sufficient to provide up to 58 wt %, preferably 55.6 wt. %, of the first granulate, an amount of microcrystalline cellulose sufficient to provide up to 6.0 wt. %, preferably 5.6 wt. % of the first granulate, an amount of pregelatinized starch sufficient to provide up to 18 wt. %, preferably 16.6 wt. % of the first granulate, an amount of croscarmellose sodium sufficient to provide up to 4 wt. %, preferably 3.3 wt. % of the first granulate, and an amount of lactose monohydrate sufficient to provide up to 16 wt. %, preferably 15.6 wt % of the first granulate, to provide a first dry-blended mixture;
    (ii) granulating the mixture from step "a(i)" using a granulating fluid comprising an amount of sodium lauryl sulfate (SLS) sufficient to provide up to 6.6 wt %, preferably 3.3 wt. % of the first granulate dissolved in an amount of water equal to about seven times the weight of SLS,
    (iii) wet-milling the granulate from step "ii" to provide a uniform granulate size;
    (iv) drying the wet granulate prepared in step (iii) until the granulate displays a loss on drying (LOD) of less than 2.5 wt. %;

(b) milling the dried first granulate through a screen to provide a classified granulate;

(c) forming a second dry-blended mixture by blending the classified granulate from step "a(iv)" with an amount of microcrystalline cellulose sufficient to provide up to 6 wt %, preferably 5.1 wt % of the second dry-blended mixture and an amount of croscarmellose sodium sufficient to provide up to 6.2 wt. %, preferably 3.1 wt % of the second dry-blended mixture; and (d) forming a granulate pharmaceutical formulation product by dry-blending the second dry-blended mixture with and an amount of magnesium stearate sufficient to provide up to 3 wt %, preferably 2 wt. % of the granulate product.

In some embodiments it is preferred to provide a medicament in capsule dosage form by filling capsules with an amount of the granular pharmaceutical formulation prepared in accordance with the above-described process sufficient to provide a desired quantity of the API contained in the particulate formulation. In some embodiments it is preferred to prepare the first granulate using a high shear mixer/granulator for blending and granulation, a wet mill equipped with a screen having 0.375 inch holes, a fluid bed dryer and a dry mill equipped with a screen having 0.040 inch holes. In some embodiments it is preferred to carry out dry-blending operations in a bin blender.

In some embodiments It is preferred to form the first granulate from a mixture made by dry-blend 40 Kg of the compound of Formula B (API), prepared in accordance with the above-described precipitation method and used as prepared, with 4.0 Kg of microcrystalline cellulose, 11.2 Kg of lactose monohydrate, 12.0 Kg of pregelatinized starch, and 2.4 Kg of croscarmellose sodium to make the first dry-blended mixture. In some embodiments it is preferred to provide a granulating fluid comprising 2.4 Kg of sodium lauryl sulfate dissolved in 48 Kg of water and to granulate the dry blended mixture until no free-flowing powder is observed. In some embodiments it is preferred to dry the granulate in a fluid bed dryer until it demonstrates a loss on drying of less than about 2.5 wt %. In some embodiments it is preferred to mill the dried granulate in a screen mill equipped with a 0.032 inch screen to provide a granular material having an average 32 mesh size. In some embodiments it is preferred to blend the dried, milled granulate with 4.0 Kg additional of microcrystalline cellulose and 2.4 Kg additional of croscarmellose sodium to provide a second dry-blended mixture, then blend 1.6 Kg of magnesium stearate with the second dry-blended mixture to provide the granular pharmaceutical formulation.

In some embodiments, optionally, aliquots of the granular pharmaceutical formulation described above are charged into gelatin capsules to provide a dosage form having the component weights shown in the table below (each dose having approximately 200 mg of API.

| Constituent | Function | Concentration (mg/capsule) |
| --- | --- | --- |
| Precipitate of Compound of Formula B[c] | Drug Substance | 200 |
| Microcrystalline Cellulose | Binder/Filler | 40 |
| Lactose Monohydrate | Filler | 56 |
| Croscarmellose Sodium | Disintegrant | 24 |
| Pregelatinized Starch | Binder | 60 |
| Sodium Lauryl Sulfate | Surfactant | 12 |
| Magnesium Stearate | Lubricant | 8 |
| Purified Water[a] | Processing Aid | (—)[a] |
| Capsule Net Fill Weight | | 400 |
| Hard Gelatin Capsule[b] | Contain Capsule Fill | 1 each |

[a]Added for processing; evaporates during the manufacturing process,
[b]No. 0, blue, opaque, preservative-free, two-piece hard gelatin capsules,
[c]Weight assumes 100% activity for precipitate - actual formulation weight adjusted upwards for lower activity.

Another aspect of the present invention is the provision of a dosage form comprising an amount of the granular pharmaceutical formulation comprising up to 58 wt. % API of the compound of Formula B, up to 6 wt. % microcrystalline cellulose, up to 18 wt. % pregelatinized starch, up to 4 wt. % croscarmellose sodium, up to 16 wt. % lactose monohydrate, and up to 6 wt. % sodium lauryl sulfate, further characterized by a bulk density of from about 0.4 g/ml to about 0.6 g/ml and wherein the particulate form of the API is an agglomerated particulate characterized by a bulk surface area of from about 5 $m^2$/g to about 12 $m^2$/g and a bulk density of from about 0.15 g/ml to about 0.19 g/ml, said dosage form further characterized by containing 800 mg of the API and exhibiting a Cmax of 2106 at about 3.0 hours and an AUC of 7029 when administered as a single dose.

In some embodiments it is preferred to provide the above-described pharmaceutical formulation by substituting for the above-described API of Formula B, one or more compounds selected from the compounds of Formulae I-XXVIII as described herein. Such formulations can be useful for inhibiting HCV protease and/or capthesin activity and have good dissolution characteristics to facilitate absorption of the compounds of Formulae I-XXVIII.

In some embodiments, it is preferred to select at least one HCV protease inhibitor from the group of HCV protease inhibitors referred to in the following documents (which are incorporated by reference herein): US20040048802A1, US20040043949A1, US20040001853A1, US20030008828A1, US20020182227A1, US20020177725A1, US20020150947A1, US20050267018A1, US20020034732A1, US20010034019A1, US20050153877A1, US20050074465A1, US20050053921A1, US20040253577A1, US20040229936A1, US20040229840A1, US20040077551A1, EP1408031A1, WO9837180A2, U.S. Pat. No. 6,696,281B1, JP11137252A, WO0111089A1, U.S. Pat. No. 6,280,940B1, EP1106702A1, US20050118603A1, JP2000007645A, WO0053740A1, WO0020400A1, WO2004013349A2, WO2005027871A2, WO2002100900A2, WO0155703A1, US20030125541A1, US20040039187A1, U.S. Pat. No. 6,608,027B1, US20030224977A1, WO2003010141A2, WO2003007945A1, WO2002052015A2, WO0248375A2, WO0066623A2, WO0009543A2, WO9907734A2, U.S. Pat. No. 6,767,991B1, US20030187018A1, US20030186895A1, WO2004087741A1, WO2004039970A1, WO2004039833A1, WO2004037855A1, WO2004030670A1, US20040229818A1, US20040224900A1, WO2005028501A1, WO2004103996A1, WO2004065367A1, WO2004064925A1, WO2004093915A1, WO2004009121A1, WO2003066103A1, WO2005034850A2, WO2004094452A2, WO2004015131A2, WO2003099316A1, WO2003099274A1, WO2003053349A2, WO2002060926A2, WO0040745A1, U.S. Pat. No. 6,586,615B1, WO2002061048A2, WO0248157A2, WO0248116A2, WO2005017125A2, WO0022160A1, US20060051745A1, WO2004021871A2, WO2004011647A1, WO9816657A1, U.S. Pat. No. 5,371,017A, WO9849190A2, U.S. Pat. No. 5,807,829A, WO0005243A2, WO0208251A2, WO2005067437A2, WO9918856A1, WO0004914A1, WO0212543A2, WO9845040A1, WO0140262A1, WO0102424A2, WO0196540A2, WO0164678A2, U.S. Pat. No. 5,512,391A, WO0218369A2, WO9846597A1, WO2005010029A1, WO2004113365A2, WO2004093798A2, WO2004072243A2, WO9822496A2, WO2004046159A1, JP11199509A, WO2005012288A1, WO2004108687A2, WO9740168A1, US20060110755A1, WO2002093519A2, U.S. Pat. No. 6,187,905B1, WO2003077729A2, WO9524414A1, WO2005009418A2, WO2004003000A2, US20050037018A1, WO9963998A1, WO0063444A2, WO9938888A2, WO9964442A1, WO0031129A1, WO0168818A2, WO9812308A1, WO9522985A1, WO0132691A1, WO9708304A2, WO2002079234A1, JP10298151A, JP09206076A, JP09009961A, JP2001103993A, JP11127861A, JP11124400A, JP11124398A, WO2003051910A2, WO2004021861A2, WO9800548A1, WO2004026896A2, WO0116379A1, U.S. Pat. No. 5,861,297A, WO2004007512A2, WO2004003138A2, WO2002057287A2, WO2004009020A2, WO2004000858A2, WO2003105770A2, WO0114517A1, WO9805333A1, U.S. Pat. No. 6,280,728B1, EP1443116A1, US20040063911A1, WO2003076466A1, WO2002087500A2, WO0190121A2, WO2004016222A2, WO9839030A1, WO9846630A1, WO0123331A1, WO9824766A1, U.S. Pat. No. 6,168,942B1, WO0188113A2, WO2005018330A1, WO2005003147A2, WO9115596A1, WO9719103A1, WO9708194A1, WO2002055693A2, WO2005030796A1, WO2005021584A2, WO2004113295A1, WO2004113294A1, WO2004113272A1, WO2003062228A1, WO0248172A2, WO0208198A2, WO0181325A2, WO0177113A2, WO0158929A1, WO9928482A2, WO9743310A1, WO9636702A2, WO9635806A1, WO9635717A2, U.S. Pat. Nos. 6,326,137B1, 6,251,583B1, 5,990,276A, 5,759,795A, 5,714,371A, 6,524,589B1, WO0208256A2, WO0208187A1, WO2003062265A2, U.S. Pat. No. 7,012,066B2, JP07184648A, JP06315377A, WO2002100851A2, WO2002100846A1, WO0039348A1, JP06319583A, JP11292840A, JP08205893A, WO0075338A2, WO0075337A1, WO2003059384A1, WO2002063035A2, WO2002070752A1, U.S. Pat. No. 6,190,920B1, WO2002068933A2, WO0122984A1, JP04320693A, JP2003064094A, WO179849A2, WO0006710A1, WO0001718A2, WO0238799A2, WO2005037860A2, WO2005035525A2, WO2005025517A2, WO2005007681A2, WO2003035060A1, WO2003006490A1, WO0174768A2, WO0107027A2, WO0024725A1, WO0012727A1, WO9950230A1, WO9909148A1, WO9817679A1, WO9811134A1, WO9634976A1, WO2003087092A2, WO2005028502A1, U.S. Pat. No. 5,837,464A, DE20201549U1, WO2003090674A2, WO9727334A1, WO0034308A2, U.S. Pat. No. 6,127,116A, US20030054000A1, JP2001019699A, U.S. Pat. Nos. 6,596,545B1, 6,329,209B1, IT1299179, CA2370400, KR2002007244, KR165708, KR2000074387, KR2000033010, KR2000033011, KR2001107178, KR2001107179, ES2143918, KR2002014283, KR149198, KR2001068676.

DETAILED DESCRIPTION OF THE INVENTION

Figure 1:
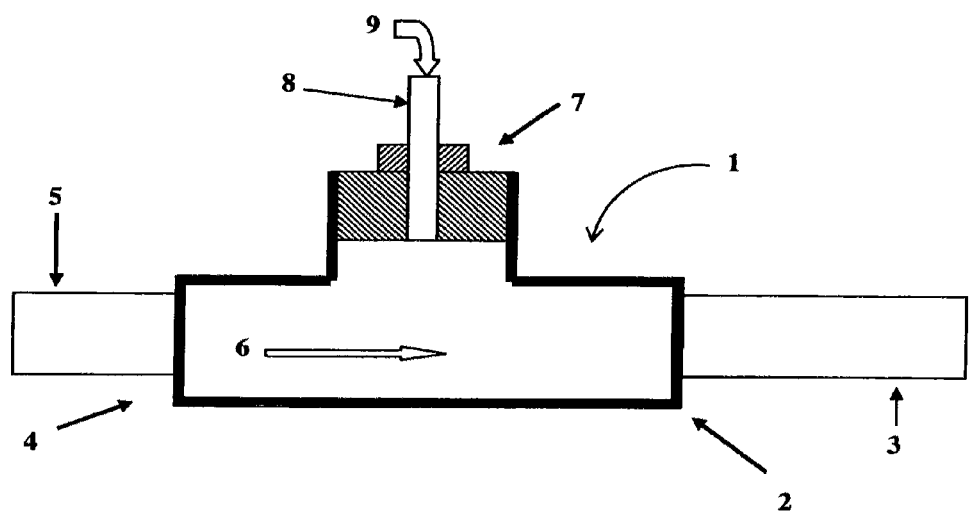
FIG. 1 presents a cross-sectional schematic view of a Tee-fitting apparatus useful for combining solution and anti-solvent streams in accordance with the present invention.

A method of making the compound of Formula B is described in U.S. Pat. No. 7,012,066 to Saskena, et al. (the '066 patent). In particular the '066 patent specifically describes the preparation of the compound of Formula B at col. 113, Example XXIV (cols. 448 to 451) and col. 1259. These sections in particular, and the entirety of the '066 patent are incorporated by reference herein. Improved processes for synthesizing the compound of Formula B are described in U.S. patent application Ser. No. 11/598,528, filed Nov. 13, 2006 (the '528 application) and International patent application no. 2006/048613 (the '613 application), filed Dec. 20, 2006. The '528 describes, on pages 10 through 13 and examples 1 to 2, improvements on the process described in the '066 patent for the preparation of the compound of Formula B, which pages, along with the entirety of the '528 application, are incorporated herein by reference. The '613 application describes, on pages 19 through 39, improvements in the improvements on the process described in the '066 patent for the preparation of the compound of Formula B, which pages, along with the entirety of the '613 application, are incorporated herein by reference.

The term "anti-solvent" as used herein is a liquid which reduces the solubility of a compound of interest when the anti-solvent is mixed into a solution comprising a solvent and the compound of interest. Accordingly, a sufficient quantity of an anti-solvent mixed with a solution comprising a compound of interest causes the compound of interest to come out of solution and precipitate as a particulate material.

The term "chord length" used herein refers to the length of a theoretical cord required to traverse one particle. Therefore, each particle has a chord length distribution characteristic of its size and shape.

As used herein "primary particle" is the initially formed particles nucleated by combining a solution and anti-solvent. "Primary particle size" refers to the size of a primary particle and is determined by Scanning Electron Microscopy (SEM).

As used herein, the term "precipitated particle" refers to a particle formed in a slurry by aggregation of primary particles. As used herein the term "agglomerated particulate" refers to an agglomeration of precipitated particles. As the terms are used herein "particle" and "particulate" pertains to material formed by precipitation processes and "granulate" refers to an agglomeration or aggregation of particles or an aggregation or agglomeration of a mixture of constituents, for example, a "granulate" prepared by agglomerating a powdered mixture of solids with a granulation fluid.

As used herein "median precipitated particle size" "median aggregate particle size" and "particulate size distribution" are determined by Laser Diffraction (LC) measurements.

As used herein, unless specified otherwise, the abbreviation "nm" means nanometers.

As used herein, the abbreviation "M" means molar unless specified otherwise

The term "Reynolds Number" (Re) as used herein is the conventional definition arising from fluid dynamics, a dimensionless parameter defined as:

$$Re = \rho UL/\mu = UL/\nu$$

wherein
$\rho$=fluid density
$\mu$=viscosity coefficient
$\nu$=kinematic viscosity
U=characteristic velocity
L=characteristic length scale As is known, Reynolds Number reflects whether a fluid is flowing under a condition of laminar or turbulent flow. In general, laminar flow conditions exist at Reynolds numbers of less than about Re=2100. Above about Re=2100 the flow begins to become turbulent, and above about Re=10,000 the flow becomes chaotic.

When precipitating material to provide an active pharmaceutical ingredient (API) for inclusion in a medicament it is necessary to tightly control the average primary particle size and the primary particle size range distribution, the average size (chord length) of agglomerates of primary particles (precipitated particles), and the size range distribution of the agglomerated particulate material (as these terms are defined above). It is also necessary to tightly control the bulk surface area and bulk density of the agglomerated particulate material, and the amount of solvent included in both primary and precipitated particles as well as the agglomerates particulate material. These parameters affect the physical properties of the particulate material produced, for example, softening point, bulk density and handling characteristics important to medicament formulation. Also affected are the pharmacological properties of the API, for example, dissolution rate, stability, and bioavailability, and the parameters employed in additional processing steps that the particulate may be subjected to in finishing the agglomerated particulate material, for example, the drying time and the maximum drying temperature which will be tolerated by the particulate material isolated from the precipitation slurry.

As discussed above, the solution/anti-solvent method for precipitation of the compound of Formula B requires the use of solutions having a high concentration of Formula B dissolved therein to minimize the anti-solvent volume used to precipitate the compound and to minimize the amount of unrecovered Formula B. When state of the art batch crystallizers are employed to carry out the precipitation of the compound of Formula B, large gradients in concentration of the solvent as it is mixed with the anti-solvent yield precipitated material having a large particle size range, and undesirably large average primary particle size and undesirably large average agglomerate particulate size. Moreover the precipitate product lacks batch to batch consistency both with regard to particulate average size and the amount of included solvent. In addition, it is inconvenient and inefficient to carry out batch operations for isolating and purifying the active compound on a commercial scale.

One aspect of the present invention is a process for precipitating an amorphous compound by a solution/anti-solvent technique, wherein the precipitate has a controlled narrow size range (microns) and a controlled narrow range in bulk surface area ($m^2/g$). Optionally, the present invention process further comprises subjecting the precipitated compound to controlled agglomeration by distilling off some of the supernatant liquid from the slurry initially prepared in the precipitation process (initial slurry) to provide a granulate material having a narrow size range and narrow range of bulk surface area. Each of these aspects of the process are discussed in turn.

The present invention provides, surprisingly, a precipitation process consistently yielding solids having a narrow size range and narrow range of cord-length. The inventive process comprises combining a stream of anti-solvent and a stream of a solution containing the compound to be precipitated, where the streams are combined with the solution stream perpendicular to the flow of the anti-solvent stream at an angle (measured relative to the direction of the anti-solvent stream flow) of substantially 90 degrees, and wherein the conditions for providing the anti-solvent stream are selected to give a Reynolds number of at least about 9000 and the conditions for providing the solution stream are selected to give a Reynolds number which is at least sufficient to produce turbulent flow, for example, an Re=to about 2000. Preferably, the antisolvent is supplied under conditions selected to provide an Re=at least about 9,000, more preferably at least about 20,000 and the solution is supplied under conditions yielding a Reynolds number of Re=at least about 5500.

Accordingly, the inventors have surprisingly found that an amorphous, solid form of the compound of Formula B having controlled primary particle size in the range of from about 200 nm to about 300 nm, with a bulk surface area of from about 25 $m^2/g$ to about 32 $m^2/g$ can be provided using the process of the present invention. Moreover, when the optional, subsequent agglomeration step (described below) is carried out the inventors have surprisingly found that the process of the present invention provides a particulate having desirable agglomerate chord length with a bulk surface area of from about 5 $m^2/g$ to about 8 $m^2/g$, and a bulk density of from about 0.15 g/ml to about 0.19 g/ml.

With reference to FIG. 1, precipitation of the compound of Formula B in accordance with the process of the present invention can be carried out on a continuous basis by using a simple apparatus having a mixing chamber comprising a mixing Tee (1), and optionally connected to the outlet leg (2) of the Tee run, static mixer (3), wherein a stream of anti-solvent is passed through the straight run inlet (4) via anti-solvent inlet line (5) in the direction of Arrow (6), and a stream of a solution comprising the compound of Formula B is passed into the branch run (7) via solution inlet line (8) in the direction of arrow (9). In one example, Tee (1) is a standard ⅜" steel Tee fitted with a ½" inlet line (5), a ⅜" static mixer (3), and a ⅛" solution inlet line (8). Using this apparatus, the precipitation process of the invention is carried out by providing the solution stream to the apparatus at a rate yielding a Reynolds number of at least about 5,500 and providing an amount of the anti-solvent at a rate to achieve a Reynolds number of at least about 9,000. In some embodiments using an apparatus having such relative dimensions it is preferred to establish conditions to provide one stream, for example, the solution stream, yielding the desired Reynolds number and maintain a volumetric ratio of the volume of the anti-solvent to the volume of solution of from about 3:1 anti-solvent:solution to about 15:1 anti-solvent:solution. Preferably, the ratio of the volume of anti-solvent to solution is supplied to the mixing Tee at a ratio of about 4:1 antisolvent:solution. Using the simple mixing apparatus described the inventors have found that conveniently these desired volumetric ratios are achieved when the solution is provided to the mixing Tee at a rate yielding a Reynolds number of at least about 5,500, preferably at least about 10,000, and the anti-solvent is provided to the mixing Tee at a rate yielding a Reynolds number of at least about 9,000, preferably at least about 15,000 and more preferably at least about 20,000. In some embodiments it is preferred to supply the anti-solvent under conditions yielding a Reynolds number of at least 25,000.

Using the compound of Formula B, the inventors have surprisingly found that when the solution and anti-solvent are combined under the above-described conditions in a simple apparatus there is achieved sufficiently rapid mixing of the anti-solvent and solution in the Tee to provide consistently a particulate amorphous solid of the compound of Formula B which has a narrow primary particle size range, facilitating the provision of a granular agglomerate having desirable physical properties suitable for use as an active pharmaceutical ingredient (API) in the provision of a medicament.

Using as an example an apparatus having a mixing chamber constructed from a plumbing Tee fitting with a nominal outside diameter run of ⅜" (fitted with ⅜" inlet and outlet tubing) and a nominal outside diameter branch leg of ¼" (fitted with ⅛" supply tubing), the desired flow conditions are realized by supplying an n-heptane anti-solvent flow rate of from about 3300 ml/min to about 4200 ml/min through the mixing Tee run, and a solution flow rate of from about 380 ml./min. to about 880 ml./min. through the mixing Tee branch leg, where the solution comprises MTBE and has dissolved therein from about 80 mg/ml to about 250 mg/ml of the compound of Formula B. It will be appreciated that other diameters and configurations of mixing chambers can be employed by varying the supply rate of the anti-solvent and solution to achieve the minimum desirable Reynolds number and provide the desired volumetric ratio of anti-solvent and solution.

Conveniently, a suitable mixing chamber for use in the process of the present invention can be provided by a standard, commercially available 90 degree Tee fitting, for example, a conventional plumbing Tee fitting, a compression Tee fitting, and a Swagelok™ Tee fitting. While a strict 90 degree relationship between anti-solvent and solution streams is not required, it is preferably to utilize a plumbing fitting which to a substantial degree does not supply the solution of the compound of Formula B to the anti-solvent stream with (from the anti-solvent frame of reference) any co-current component. To the degree that a fitting is used having inlets which impart some concurrent character, it will be appreciated that adjustments should be made to increase the Reynolds numbers of the combining anti-solvent and solution streams, providing a more turbulent mixing environment to compensate for the co-current component of the combination.

Thus, for example, if the mixing chamber had the configuration of a Y-fitting having input legs less than 120 degrees apart (thus they form an angle of greater than 120 degrees with the common leg), the two narrow angle legs could be utilized for solution and anti-solvent input with a selection of conditions leading to a concomitant increase in the Reynolds number of the inlet streams to offset the co-current component of the combining streams. Conversely, if such a Tee were used with the common leg and one narrow-angle leg employed as the inlet legs, and thus the streams are combined with an impinging component, a selection of conditions leading to a concomitant decrease in the Reynolds number of the input streams could be employed taking advantage of the degree to which the streams combined with an impinging component that improves the mixing of the combining streams. Accordingly, fittings having leg configurations other than a Tee-configuration may be employed in the process of the present invention with suitable alteration of conditions to provide the necessary Reynolds number for configurations having an orientation imparting a substantial co-current or impinging component to the combining streams.

Optionally a conventional static mixer can be employed on the outlet leg of the mixing chamber, for example a Model 1-TU-3L-12-1 static mixer from KoFlo Corporation (Cary, Ill.) providing additional control of the physical properties of the particulate produced by increasing the mixing time and intensity of the solution and anti-solvent after the streams are combined.

Different solvent and anti-solvent combinations may be employed depending upon the compound to be precipitated. For the compound of Formula B, preferably the anti-solvent is selected from the group consisting of linear or branched hydrocarbons having from about 5 carbon atoms to about 12 carbon atoms, preferably from about 5 carbon atoms to about 8 carbon atoms, more preferably linear hydrocarbons having from about 5 to about 8 carbon atoms, more preferably n-heptane. For the compound of Formula B, preferably the solvent used to provide a solution of the compound of Formula B is selected from acetone, methyl-tertiarybutyl-ether (MTBE), and mixtures of ethyl acetate and MTBE, more preferably the solvent is MTBE. When acetone is selected as a solvent it is preferred to use water as an antisolvent. When MTBE or mixtures of MTBE and ethyl acetate are selected as a solvent it is preferable to use n-heptane as an anti-solvent. In precipitating the compound of Formula B in accordance with the present invention method it is preferred to use MTBE as a solvent and n-heptane as an antisolvent.

In some embodiments when it is not desirable to carry out a subsequent optional step of distilling off supernatant liquid from the collected initially formed slurry (described herein), preferably the solution and anti-solvent are dried rigorously prior to combining the streams and forming the precipitate, thus substantially eliminating water from the initially formed slurry. Examples of drying methods which may be employed include filtration through a medium that absorbs water, for example, CUNO filtration, distillation methods, and contacting the solution or anti-solvent with a drying agent, for example, molecular sieves.

The precipitation process of the present invention is preferably run with a highly concentrated solution of the compound to be precipitated. In some embodiments it is preferred for the solution of the compound of Formula B to contain from about 80 g of the compound of Formula B/ml of solution (0.15 M) to about 250 mg of the compound of Formula B/ml of solution (0.48 M). In some embodiments it is preferred to use a solution comprising about 166 mg of the compound of Formula B/ml of solution (0.32 M). In some embodiments utilizing these concentrations it is preferred to maintain the solution at a temperature of from about −20° C. to about +25° C., preferably at a temperature of from about −10° C. to about +20° C., and more preferably the solution is maintained at 0° C. In some embodiments of the precipitation process of the invention, when the compound to be precipitated is the compound of Formula B, it is preferred to maintain both the anti-solvent and the solution of the compound of Formula B at a temperature of from about −25° C. to about +25° C., preferably from about −25° C. to about +20° C. In some embodiments it is preferred to use a solution comprising about 166 mg of the compound of Formula B/ml of solution (0.32 M) and to maintain the solution at a temperature of about 0° C.

The present invention precipitation process can be carried out in an apparatus that includes thermally controlled supply lines, mixing chamber (for example, a cooling line-traced mixing Tee) and conduits to maintain any desired temperature. In some embodiments it is preferred to maintain the supply lines and mixing chamber at ambient temperature, typically about 25° C., and supply the mixing chamber with anti-solvent and solution of the compound of Formula B which has been maintained at a desired temperature, such that upon combining the streams the slurry produced is permitted to warm to the ambient temperature as it passes through the system. In some embodiments of the precipitation process the supply of solution and anti-solvent are preferably maintained at a temperature of from about −25° C. to about +20° C. In some embodiments of the precipitation process it is preferred to maintain the supply of the solution of the compound of Formula B at a temperature of from about −10° C. to about 20° C.

In some embodiments it is preferred to trace the supply conduit for the solution of the compound of Formula B up to the mixing chamber with a cooling line, and thereby maintain the solution entering the mixing chamber at a temperature of about 0° C. In some embodiments it is preferred to trace the anti-solvent supply conduit up to the mixing chamber with a cooling line to maintain the anti-solvent supply at a temperature of about −20° C. When a solution of the compound of Formula B is supplied to the mixing chamber at 0° C. and the anti-solvent is supplied to the mixing chamber at −20° C. it is typically found that the slurry produced has a temperature of about −15° C.

Figure 2:
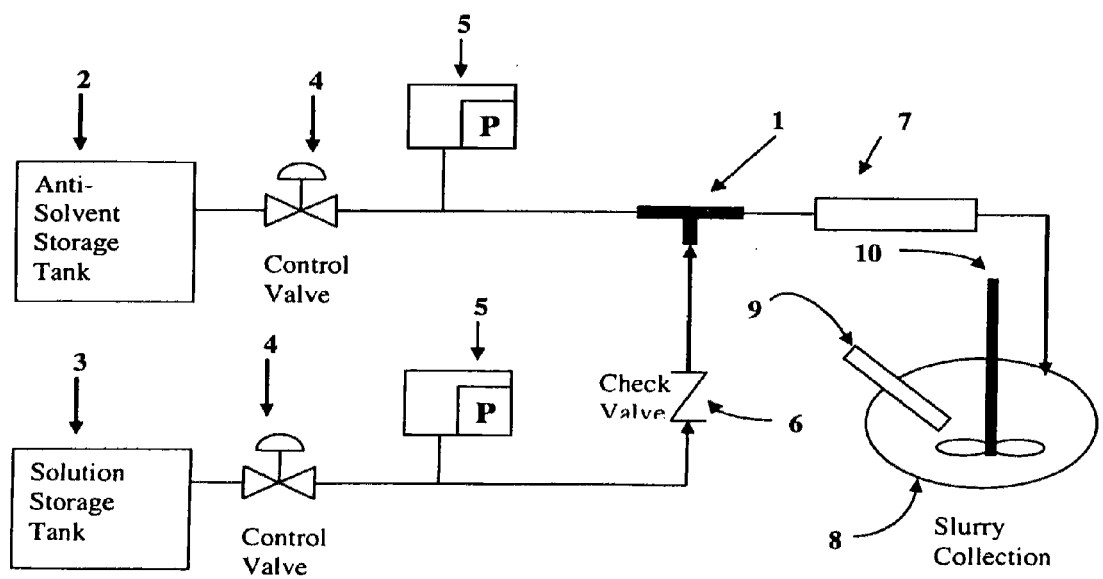
FIG. 2 presents a schematic flow diagram of an apparatus which includes a mixing Tee for producing a precipitate in accordance with the present invention.

The present invention process used to precipitate the compound of Formula B can be employed as part of a continuous precipitation process. For example with reference to FIG. 2, as shown schematically in FIG. 2, inlet run leg of mixing tee (1) can be supplied from storage tank (2), with anti-solvent and the branch leg inlet of mixing tee (1) can be supplied with a solution of the compound of Formula B from storage tank (3) through check valve (6). The combined solution and anti-solvent (which produces a slurry as the compound of Formula B precipitates) can be conducted from the mixing Tee (1) outlet, optionally through a static mixer (7), to holding tank (8). Accordingly in this manner the compound can be precipitated in the mixing Tee continuously. With further reference to FIG. 2, if the slurry formed in the mixing tee is conducted through a conduit having an output which can be directed to one of several to holding tanks (8), as each tank reaches capacity, the collected slurry can be further processed while the precipitation process carried out in the mixing tee continues to run with the outlet of the mixing tee conducted to a fresh holding tank. Alternatively the output of the mixing Tee and optional static mixer can be conducted directly to a device for separating the precipitate from the liquids, for example, a vacuum filtration device, a centrifuge, or a settling tank for decantation of the combined solvent and anti-solvent.

With reference to FIG. 2, when the mixing device is supplied by storage tank (2) of anti-solvent and storage tank (3) of a solution of the compound of Formula B, the flow of anti-solvent and solution through the mixing Tee can be controlled by any means, for example, control valves (4), selected, for example from a throttling valve, a needle valve, a metering pump, a flow meter, and a mass flow controller. It will be appreciated that other means for regulating the flow of liquids can also be employed. Optionally, as depicted in FIG. 2, pressure gauges (5) and other process monitoring devices may be installed a various points in the system to aid in controlling the process.

As mentioned above, and indicated in FIG. 2, in some embodiments of the process of the present development, the slurry produced in the mixing Tee is directed to a holding tank (8) equipped with stirrer (10). Optionally, after a quantity of the slurry has been collected, some of the supernatant liquid of the collected slurry is distilled off from the tank under a partial vacuum, thereby concentrating the slurry and agglomerating the precipitated particles to provide an agglomerated particulate of desirable bulk surface area and bulk density. During agglomeration, the high bulk surface area precipitated particles are agglomerated to give a granular material having a reduced bulk surface area, preferably a surface area of from about 5 $m^2/g$ to about 8 $m^2/g$, and correspondingly changes the bulk density of the agglomerated particulate material from a bulk density ranging from about 0.25 g/ml to about 0.35 g/ml for the precipitated particle material to a bulk density of from about 0.15 g/ml to about 0.2 g/ml for the agglomerated particulate material. Changes in bulk surface area can be monitored during distillation by PSD measuring probe (9), as described herein.

Another benefit of employing the optional distillation step is reducing the amount of volatile constituents retained in the precipitated particles and agglomerated particulate. Examples of volatile constituents which may be retained in precipitated materials include MTBE, acetic acid, and water, the presence of each of which arises from the preparation and processing of the compound of Formula B before or during the precipitation process. Additional advantages of the optional distillation step include a reduction in the volume of liquid which must be handled to separate the precipitated particulates from the slurry, and a reduction in the amount of the compound of Formula B which is retained in the supernatant liquid of the slurry. During the optional distillation step the temperature and pressure of the distillation must be carefully controlled to maintain a narrow distribution of agglomerated particulate chord size in the isolated solid product.

Figure 3:
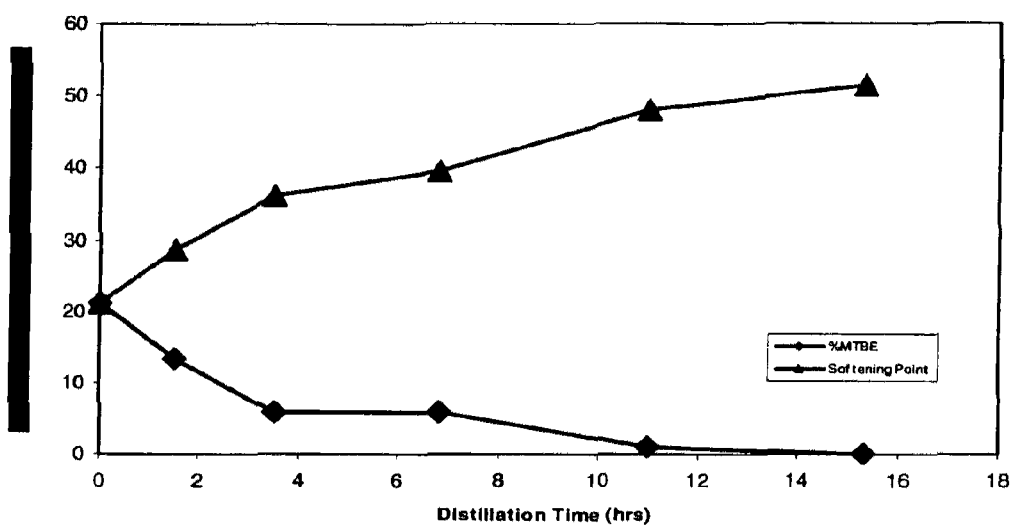
FIG. 3 presents a graphic representation of the effects of distillation on softening point of precipitate produced.
Figure 4:
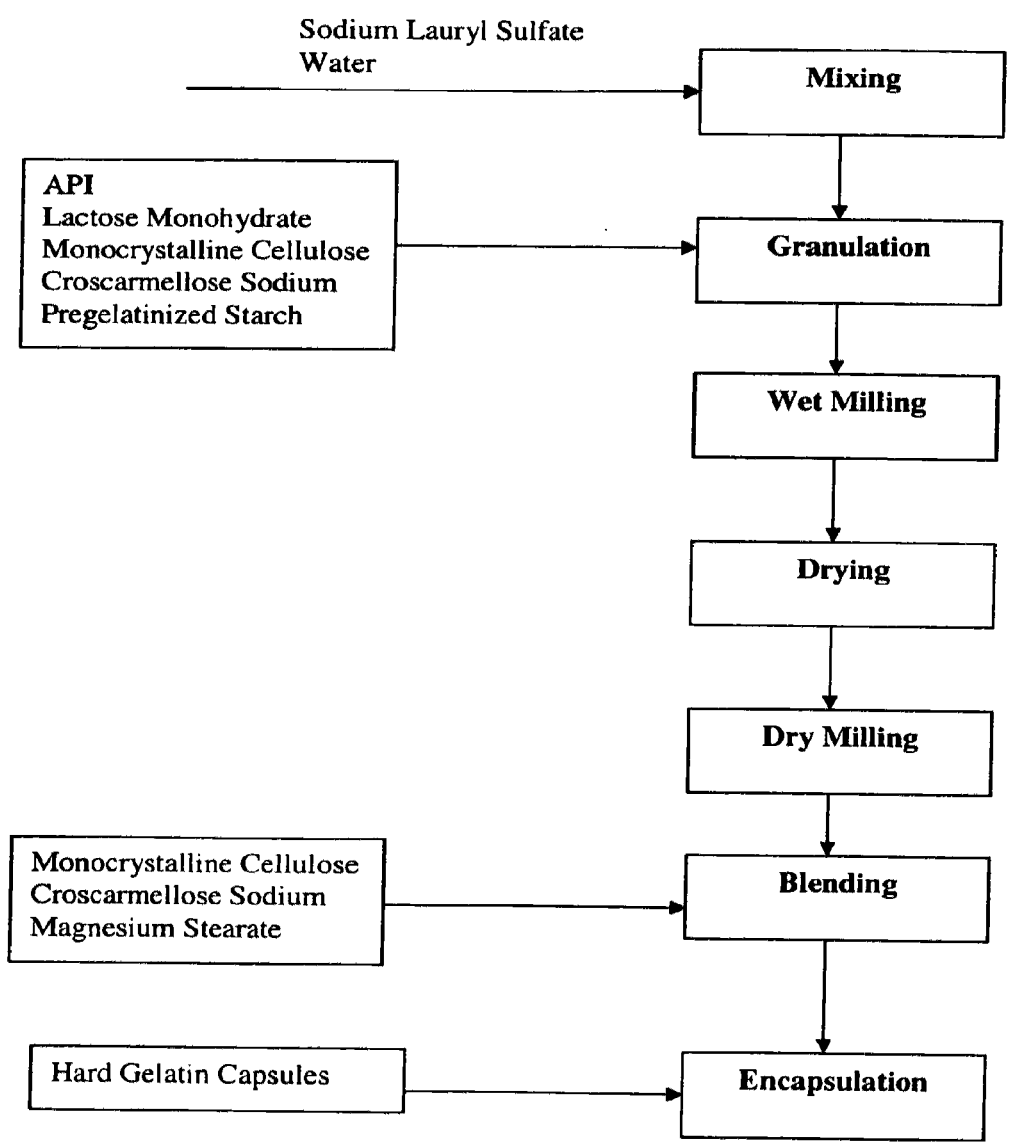
FIG. 4 presents a schematic diagram of a manufacturing process.
Figure 5:
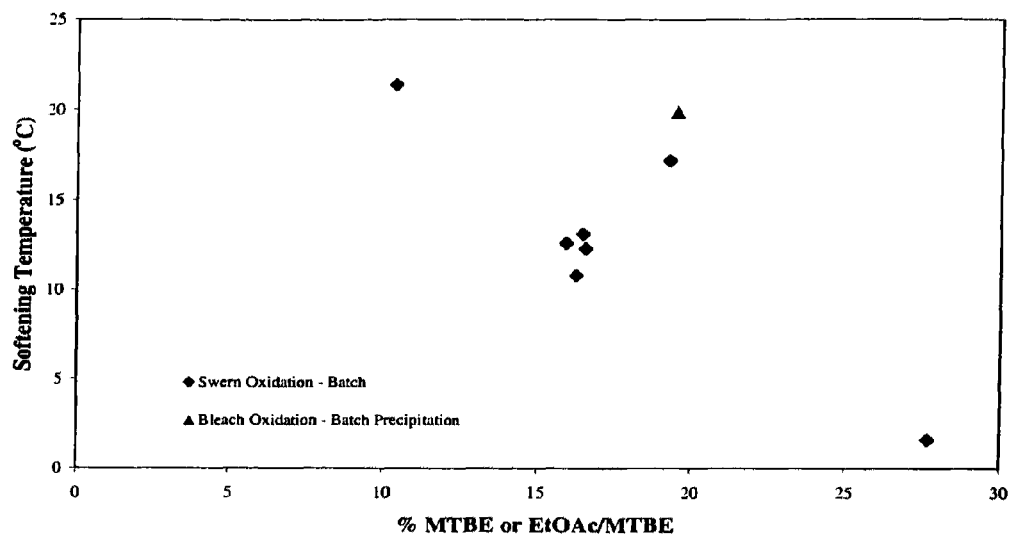
FIG. 5 presents a graphic representation of the softening point of comparative particulate materials prepared using a stirred batch process.

Without wanting to be bound by theory, it is believed that a reduction in the amount of volatile constituents, for example, MTBE, water, and mixtures of MTBE and water, retained in the precipitated solids raises the softening point of the solids, and thereby reduces the potential for the precipitated solids to attain a "gummy" consistency while permitting higher drying temperatures of the collected precipitate. With reference to FIG. 3, it can be seen that as the percent of MTBE is reduced in the slurry the softening temperature of the particulate in the slurry rises. A similar relationship exists between the softening temperature of the precipitated material and the amount of water present in the slurry. The inventors have discovered also that the combination of water and MTBE has a synergistic effect on lowering the softening point of the precipitated material compared to either water or MTBE alone. Accordingly it is desirable to remove water to the lowest amount possible when MTBE has been employed as a solvent in the precipitation process of the present invention.

The optional vacuum distillation step is carried out while the slurry is agitated, for example, by a mechanical stirrer. Preferably the distillation step is carried out with the supernatant liquid of the collected slurry at a temperature below the softening point of the precipitated solids in the slurry. In some embodiments it is preferred to maintain the temperature of the supernatant below about 25° C. until at least 10 vol % of the collected supernatant liquid has been distilled off. In some embodiments the temperature of the collected slurry is maintained at about 20° C. or less until at least about 2 vol % of the collected slurry has been distilled off, and then it is heated in 1° C. increments from 20° C. to 26° C. as each additional 2 vol % of the initially collected slurry that is distilled off. In some embodiments, after distilling off 13 vol % of the initially collected slurry, the temperature is maintained at 32° C. or less until the volume of the slurry is about one third the volume of the initially collected slurry. In some embodiments it is preferred to distill off supernatant liquid from the slurry until the amount of water present in the remaining supernatant liquid of the slurry is about 0.003 wt. % or less. In some embodiments the distillation is continued until the amount of MTBE present in the supernatant liquid of the slurry is less than about 0.2 wt. %, preferably from about 0.12 wt. % to about 0.2 wt. %. In some embodiments it is preferred to reduce the volume of the concentrated slurry to about one third of the volume of slurry initially collected.

It will be appreciated that as the type and amounts of volatile constituents present in the solution varies from that discussed above in the initially collected slurry, the distillation and agglomeration step will require conditions that depart from the distillation scheme previously described. The temperature/pressure requirements for agglomerating a given batch of precipitate can be selected, guided by sampling the batch and determining the softening temperature of the precipitate in the slurry sample, then carrying out the distillation of the slurry at each stage at a suitable temperature to avoid softening the precipitate therein, and adjusting the applied vacuum as needed to progress the distillation and agglomeration and to maintain a satisfactory rate and a desired range of agglomerate particulate size.

It will be appreciated that by eliminating volatile constituents from the solution prior to conducting the precipitation process of the invention, particularly water, the precipitation process can be carried out utilizing low ratios of anti-solvent: solution in the precipitation step, for example ratios of 2:1 anti-solvent: solution, preferably 3:1 anti-solvent: solution can be employed under these conditions. When such ratios are employed with solution which is substantially free of water it is expected that the parameters of the precipitation process can be adjusted to provide a precipitate of desirable particle size and bulk surface area while retaining the narrow particle size distribution offered by the precipitation process of the present invention.

It will be appreciated from the foregoing discussion that the process of the present invention can be applied to other mixing-controlled precipitation process yielding precipitated particulate materials having narrow and controlled particle size, chord length, bulk surface area and bulk density. Examples of other compounds include the compounds of Formula A and the compounds of the Formulae of Structures I to XXVIII, whether crystalline or amorphous.

Next will be described pharmaceutical formulation prepared from the precipitated particulate material provided by the present invention.

Pharmaceutical Formulations

In some embodiments of the invention, the above-described precipitated material is incorporated into a formulation for the provision of a medicament useful in treating HCV infections, preferably wherein the precipitated material comprises the compound of Formula B. In some embodiments it is preferred to prepare a medicament from a precipitated form of the compound of Formula B having a primary particle size of less than about 1.0 micron, preferably a primary particle size of from about 200 nm to about 300 nm, a median precipitated particle size (aggregation of primary particles) of from about 1 micron to about 2.5 microns, preferably about 1.5 microns, a precipitated particle size distribution of from about 1 micron to about 50 microns and a level of included solvent of less than about 1 wt. %. In some embodiments, it is preferred to employ agglomerated particulate (agglomeration of the precipitated particles) comprising the compound of Formula B having a bulk surface area range of from about 5 $m^2/g$ to about 12 $m^2/g$ in the provision of a pharmaceutical formulation. More preferred is agglomerated particulate having a median bulk surface area of about 7 $m^2/g$, and a bulk density of from about 0.15 g/ml to about 0.19 g/ml for example, an agglomerated particulate prepared by subjecting initially precipitated slurry containing precipitated particles having a bulk surface area of from about 16 $m^2/g$ to about 33 $m^2/g$, preferably from about 25 $m^2/g$ to about 32.5 $m^2/g$ to a condensation step at a temperature below the softening point of the solids initially precipitated, as discussed infra. In some embodiments it is preferred to prepare a pharmaceutical formulation providing the agglomerated particulate material comprising the compound of Formula B in a granular form suitable for use as a capsule fill. In some embodiments the formulation comprises a granulate comprising up to 58 wt. % of the compound of Formula B API, up to 6 wt. % microcrystalline cellulose, up to 18 wt. % pregelatinized starch, up to 4 wt. % croscarmellose sodium, up to 16 wt. % lactose monohydrate, and up to 6 wt. % sodium lauryl sulfate. In some embodiments it is preferred for the granulate to have a bulk density of from about 0.4 g/ml to about 0.6 g/ml, more preferably a bulk density of about 0.468 g/ml.

As the phrase is used herein, "weight of API" refers to the amount of Active Pharmaceutical Ingredient (by weight) contained in a material supplying the API. Accordingly, if a material comprises 80% active pharmaceutical ingredient, 100 grams of the material must be employed to supply 80 grams of API. Thus, the weight of API used in a formulation refers to the theoretical weight of 100% API present in the mass of material used to supply the API to the composition, and the actual weight of the material used to supply that weight of API is adjusted accordingly.

In some embodiments it is preferred to incorporate an aliquot of precipitated particulate material provided by the present invention into a granulate suitable for use in the provision of a pharmaceutical formulation using a process comprising:

(a) providing a dry-blended mixture by blending an amount of the precipitated particulate material (API) prepared in accordance with the process of the invention sufficient to provide up to 58 wt % of the granulate, preferably 55.6 wt. %, an amount of microcrystalline cellulose sufficient to provide up to 6.0 wt. %, preferably 5.6 wt. % of the granulate, an amount of pregelatinized starch sufficient to provide up to 18 wt. %, preferably 16.6 wt. % of the granulate, an amount of croscarmellose sodium sufficient to provide up to 4 wt. %, preferably 3.3 wt. % of the granulate, and an amount of lactose monohydrate sufficient to provide up to 16 wt. %, preferably 15.6 wt % of the granulate;

(b) granulating the dry-blended mixture from step "a" using a granulating fluid comprising an amount of sodium lauryl sulfate (SLS) sufficient to provide up to 6.6 wt % preferably 3.3 wt. % of the granulate dissolved in a weight of water equal to from about 12 times to about 13 times the weight of SLS employed;

(c) wet-milling the granulate from step "b" to provide a uniform granulate size;

(d) drying the wet granulate prepared in step (b) until the granulate displays a loss on drying (LOD) of less than 2.5 wt. %, preferably from about 1.5 wt. % to about 2.5 wt. %; and (e) milling the dried first granulate through a screen to provide a classified granulate.

In some embodiments it is preferred to employ a low or high shear mixer to dry-blend the materials in step "a", preferably a high shear mixer/granulator is employed, which, conveniently, is also employed in subsequent step "b" to granulate the dry-blended mixture. In some embodiments it is preferred to wet-mill the granulate from step "b" in a wet mill equipped with a screen having 0.375 inch holes. In some embodiments it is preferred to dry the wet granulate in a apparatus selected from an oven and a fluid bed dryer, more preferably a fluid bed dryer is used. In some embodiments it is preferred to use a dry mill equipped with a screen having 0.040 inch holes to carry out dry-milling step "e". It will be appreciated that other techniques may be employed to prepare the granulate, including employing low or high shear blender/granulator equipment, and employing manual or automated screening equipment for both wet and dry milling.

In some embodiments it is preferred to incorporate the classified granulate prepared above into a pharmaceutical composition comprising extragranular croscarmellose sodium, extragranular microcrystalline cellulose and extragranular magnesium stearate. In some embodiments the pharmaceutical composition is preferably 50 wt. % API (intragranular), 14 wt. % lactose monohydrate (intragranular), 5 wt. % intragranular microcrystalline cellulose, 5 wt. % extragranular microcrystalline cellulose, 3 wt % intragranular croscarmellose sodium, 3 wt. % extragranular croscarmellose sodium, 15 wt. % pregelatinized starch (intragranular), 3 wt. % sodium lauryl sulfate (intragranular), and 2 wt. % magnesium stearate (extragranular).

In some embodiments a granular pharmaceutical formulation containing the classified granulate is prepare by further blending the granulate containing the API with excipients to provide a granular pharmaceutical formulation product from which a dosage form is manufactured. In some embodiments this is accomplished by utilizing the above-described process to prepare a granulate with steps further comprising:

(a) dry-blending the classified granulate from step "e" of the above-described granulation process with an amount of microcrystalline cellulose equal to the amount of microcrystalline cellulose present in the classified granulate and an amount of croscarmellose sodium equal to the weight of the croscarmellose sodium present in the classified granulate to provide a homogeneous granular powder; and (b) dry-blending the homogeneous granular powder from dry-blending step "a" with and an amount of magnesium stearate sufficient to provide 2 wt. % of the dry-blended product, thereby providing a granular pharmaceutical formulation.

In some embodiments an amount of microcrystalline cellulose greater than the amount present in the granulate can be employed. In some embodiments an amount of croscarmellose sodium greater than the amount present in the granulate can be employed. In some embodiments it is preferred to carry out blending steps "a" and "b" described above using a blending method selected from a tumble blender and a bin blender, more preferably a bin blender, although it will be appreciated that homogeneous blends can be provided by employing any suitable means of dry-blending particulate materials.

In some embodiments it is preferred to provide a medicament in capsule dosage form by filling capsules with an amount of the granular pharmaceutical formulation prepared in accordance with the above-described process sufficient to provide a therapeutic serum level of the API contained in the granular pharmaceutical formulation.

In some embodiments It is preferred to form granulate for use in a pharmaceutical formulation by granulating a dry-blended mixture made by dry-blending 40 Kg of the compound of Formula B (API), prepared in accordance with the above-described precipitation method and used as prepared, 4.0 Kg of microcrystalline cellulose, 11.2 Kg of lactose monohydrate, 12.0 Kg of pregelatinized starch, and 2.4 Kg of croscarmellose sodium. In some embodiments it is preferred to provide a granulating fluid comprising 2.4 Kg of sodium lauryl sulfate dissolved in 48 Kg of water and to granulate the dry blended mixture until no free-flowing powder is observed. In some embodiments it is preferred to dry the granulate in a fluid bed dryer until it demonstrates a loss on drying of less than about 2.5 wt %. In some embodiments it is preferred to mill the dried granulate in a screen mill equipped with a 0.032 inch screen to provide a granular material having an average 32 mesh size. In some embodiments it is preferred to blend the dried, milled granulate with 4.0 Kg additional of microcrystalline cellulose and 2.4 Kg additional of croscarmellose sodium to provide a second dry-blended mixture, then blend 1.6 Kg of magnesium stearate with the second dry-blended mixture to provide the granulate product.

For use in the granulate of the invention it is preferred to employ microcrystalline cellulose equivalent to Avicel PH102, it is preferred to use impalpable grade lactose monohydrate, it is preferred to employ pregelatinized starch 1500 equivalent to that from Colorcon, it is preferred to use NF grade croscarmellose sodium; and it is preferred to use sodium lauryl sulfate equivalent to NF grade from Stepan and magnesium stearate NF grade derived from vegetable base steric acid. Suitable materials are available commercially, for example, Avicel PH102 microcrystalline cellulose from FMC, impalpable grade lactose monohydrate from Foremost Farms, pregelatinized starch 1500 from Colorcon, croscarmellose sodium NF grade from FMC, sodium lauryl sulfate Stepanol WA-100 NF from Stepan, and vegetable grade magnesium stearate from Greven.

In some embodiments, optionally, aliquots of the homogeneous powder are charged into gelatin capsules to provide a dosage form having the component weights shown in the table below (each dose having approximately 200 mg of API.

| Constituent | Function | Concentration (mg/capsule) |
| --- | --- | --- |
| Precipitate of Compound of Formula B[c] | Drug Substance | 200 |
| Microcrystalline Cellulose | Binder/Filler | 40 |
| Lactose Monohydrate | Filler | 56 |
| Croscarmellose Sodium | Disintegrant | 24 |
| Pregelatinized Starch | Binder | 60 |
| Sodium Lauryl Sulfate | Surfactant | 12 |
| Magnesium Stearate | Lubricant | 8 |
| Purified Water[a] | Processing Aid | (—)[a] |
| Capsule Net Fill Weight | | 400 |
| Hard Gelatin Capsule[b] | Contain Capsule Fill | 1 each |

[a]Added for processing; evaporates during the manufacturing process,
[b]No. 0, blue, opaque, preservative-free, two-piece hard gelatin capsules,
[c]Weight assumes 100% activity for precipitate - adjusted upwards for API source material having lower activity It will be appreciated that each excipient may function in more that one role, for example a binder may also participate as a disintegrant. Accordingly, the designations of function are meant to be indicative of a primary, but not exclusive, role performed by a given excipient in the table above.

Alternative Embodiments

In some embodiments it is preferred to provide a pharmaceutical formulation in accordance with the above-described process that contains as API one or more of the compounds selected from the compounds of Formulae I-XXVIII as described herein. Such formulations can be useful for inhibiting HCV protease and/or capthesin activity and have good dissolution characteristics to facilitate absorption of the compounds of Formulae I-XXVIII.

In some embodiments, it is preferred to select at least one HCV protease inhibitor from the group of HCV protease inhibitors referred to in the following documents (which are incorporated by reference herein): US20040048802A1, US20040043949A1, US20040001853A1, US20030008828A1, US20020182227A1, US20020177725A1, US20020150947A1, US20050267018A1, US20020034732A1, US20010034019A1, US20050153877A1, US20050074465A1, US20050053921A1, US20040253577A1, US20040229936A1, US20040229840A1, US20040077551A1, EP1408031A1, WO9837180A2, U.S. Pat. No. 6,696,281B1, JP11137252A, WO00111089A1, U.S. Pat. No. 6,280,940B1, EP1106702A1, US20050118603A1, JP2000007645A, WO0053740A1, WO0020400A1, WO2004013349A2, WO2005027871A2, WO2002100900A2, WO155703A1, US20030125541A1, US20040039187A1, U.S. Pat. No. 6,608,027B1, US20030224977A1, WO2003010141A2, WO2003007945A1, WO2002052015A2, WO0248375A2, WO0066623A2, WO0009543A2, WO9907734A2, U.S. Pat. No. 6,767,991B1, US20030187018A1, US20030186895A1, WO2004087741A1, WO2004039970A1, WO2004039833A1, WO2004037855A1, WO2004030670A1, US20040229818A1, US20040224900A1, WO2005028501A1, WO2004103996A1, WO2004065367A1, WO2004064925A1, WO2004093915A1, WO2004009121A1, WO2003066103A1, WO2005034850A2, WO2004094452A2, WO2004015131A2, WO2003099316A1, WO2003099274A1, WO2003053349A2, WO2002060926A2, WO0040745A1, U.S. Pat. No. 6,586,615B1, WO2002061048A2, WO0248157A2, WO0248116A2, WO2005017125A2, WO0022160A1, US20060051745A1, WO2004021871A2, WO2004011647A1, WO9816657A1, U.S. Pat. No. 5,371,017A, WO9849190A2, U.S. Pat. No. 5,807,829A, WO0005243A2, WO0208251A2, WO2005067437A2, WO9918856A1, WO0004914A1, WO0212543A2, WO9845040A1, WO0140262A1, WO0102424A2, WO0196540A2, WO0164678A2, U.S. Pat. No. 5,512,391A, WO0218369A2, WO9846597A1, WO2005010029A1, WO2004113365A2, WO2004093798A2, WO2004072243A2, WO9822496A2, WO2004046159A1, JP11199509A, WO2005012288A1, WO2004108687A2, WO9740168A1, US20060110755A1, WO2002093519A2, U.S. Pat. No. 6,187,905B1, WO2003077729A2, WO9524414A1, WO2005009418A2, WO2004003000A2, US20050037018A1, WO9963998A1, WO0063444A2, WO9938888A2, WO9964442A1, WO0031129A1, WO0168818A2, WO9812308A1, WO9522985A1, WO0132691A1, WO9708304A2, WO2002079234A1, JP10298151A, JP09206076A, JP09009961A, JP2001103993A, JP11127861A, JP11124400A, JP11124398A, WO2003051910A2, WO2004021861A2, WO9800548A1, WO2004026896A2, WO0116379A1, U.S. Pat. No. 5,861,297A, WO2004007512A2, WO2004003138A2, WO2002057287A2, WO2004009020A2, WO2004000858A2, WO2003105770A2, WO0114517A1, WO9805333A1, U.S. Pat. No. 6,280,728B1, EP1443116A1, US20040063911A1, WO2003076466A1, WO2002087500A2, WO0190121A2, WO2004016222A2, WO9839030A1, WO9846630A1, WO0123331A1, WO9824766A1, U.S. Pat. No. 6,168,942B1, WO0188113A2, WO2005018330A1, WO2005003147A2, WO9115596A1, WO9719103A1, WO9708194A1, WO2002055693A2, WO2005030796A1, WO2005021584A2, WO2004113295A1, WO2004113294A1, WO2004113272A1, WO2003062228A1, WO0248172A2, WO0208198A2, WO0181325A2, WO0177113A2, WO0158929A1, WO9928482A2, WO9743310A1, WO9636702A2, WO9635806A1, WO9635717A2, U.S. Pat. Nos. 6,326,137B1, 6,251,583B1, 5,990,276A, 5,759,795A, 5,714,371A, 6,524,589B1, WO0208256A2, WO0208187A1, WO2003062265A2, U.S. Pat. No. 7,012,066B2, JP07184648A, JP06315377A, WO2002100851A2, WO2002100846A2, WO0039348A1, JP06319583A, JP11292840A, JP08205893A, WO0075338A2, WO0075337A1, WO2003059384A1, WO2002063035A2, WO2002070752A1, U.S. Pat. No. 6,190,920B1, WO2002068933A2, WO0122984A1, JP04320693A, JP2003064094A, WO0179849A2, WO0006710A1, WO0001718A2, WO0238799A2, WO2005037860A2, WO2005035525A2, WO2005025517A2, WO2005007681A2, WO2003035060A1, WO2003006490A1, WO0174768A2, WO0107027A2, WO0024725A1, WO0012727A1, WO9950230A1, WO9909148A1, WO9817679A1, WO9811134A1, WO9634976A1, WO2003087092A2, WO2005028502A1, U.S. Pat. No. 5,837,464A, DE20201549U1, WO2003090674A2, WO9727334A1, WO0034308A2, U.S. Pat. No. 6,127,116A, US20030054000A1, JP2001019699A, U.S. Pat. Nos. 6,596,545B1, 6,329,209B1, IT1299179, CA2370400, KR2002007244, KR165708, KR2000074387, KR2000033010, KR2000033011, KR2001107178, KR2001107179, ES2143918, KR2002014283, KR149198, KR2001068676.

Preferably, an amount of the formulation is provided to a patient in need thereof which provides the HCV protease inhibitor at a dosage range of about 100 to about 4000 mg per day (e.g., 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, 2100 mg, 2150 mg, 2200 mg, 2250 mg, 2300 mg, 2350 mg, 2400 mg, 2450 mg, 2500 mg, 2550 mg, 2600 mg, 2650 mg, 2700 mg, 2750 mg, 2800 mg, 2850 mg, 2900 mg, 2950 mg, 3000 mg, 3050 mg, 3100 mg, 3150 mg, 3200 mg, 3250 mg, 3300 mg, 3350 mg, 3400 mg, 3450 mg, 3500 mg, 3550 mg, 3600 mg, 3650 mg, 3700 mg, 3750 mg, 3800 mg, 3850 mg, 3900 mg, 3950 mg, 4000 mg per day). In one preferred embodiment, the HCV protease inhibitor is administered at a dosage range of about 400 mg to about 2500 mg per day. In another preferred embodiment, the HCV protease inhibitor is administered at a dosage range of about 1900 mg to about 4000 mg per day. In yet another preferred embodiment, the HCV protease inhibitor is administered at a dosage range of about 1050 mg to about 2850 mg per day.

In one embodiment, wherein the HCV protease inhibitor is the compound of Formula I, a pharmaceutically acceptable salt, solvate, or ester thereof, the HCV protease inhibitor is administered at a dosage range of about 1920 mg to about 4000 mg per day, preferably about 1920 mg to about 3000 mg per day or about 2560 mg to about 4000 mg per day.

In one embodiment, wherein the HCV protease inhibitor is the compound of Formula XXVII, a pharmaceutically acceptable salt, solvate, or ester thereof, the HCV protease inhibitor is administered at a dosage range of about 1080 mg to about 3125 mg per day, preferably about 1800 to about 2813 mg per day.

In one embodiment, wherein the HCV protease inhibitor is the compound of Formula XXVIII, a pharmaceutically acceptable salt, solvate, or ester thereof, the HCV protease inhibitor is administered at a dosage range of about 1080 mg to about 3125 mg per day, preferably about 1800 to about 2813 mg per day.

Note that the dosage of HCV protease inhibitor may be administered as a single dose (i.e., QD) or divided over 2-4 doses (i.e., BID, TID, or QID) per day. In one embodiment, the HCV protease inhibitor is administered at a dosage range of about 600 mg QID to about 800 mg QID. In one embodiment, wherein the HCV protease inhibitor is the compound of Formula I, a pharmaceutically acceptable salt, solvate, or ester thereof, the HCV protease inhibitor is administered at a dosage of 800 mg TID, 600 mg OID, or 800 mg QID. In another embodiment, wherein the HCV protease inhibitor is the compound of Formula XXVII, a pharmaceutically acceptable salt, solvate, or ester thereof, the HCV protease inhibitor is administered at a dosage of 750 mg TID. Likewise, in another embodiment, wherein the HCV protease inhibitor is the compound of Formula XXVIII, a pharmaceutically acceptable salt, solvate, or ester thereof, the HCV protease inhibitor is administered at a dosage of 750 mg TID.

Preferably, the HCV protease inhibitor is administered orally.

The structure of compounds of Formula I is disclosed in PCT International publication WO03/062265 published Jul. 31, 2003. Non-limiting examples of certain compounds disclosed in this publication include those listed at pages 48-75, incorporated herein by reference, or a pharmaceutically acceptable salt, solvate, or ester thereof.

In one embodiment, the API is selected from compounds of the formula Ia:

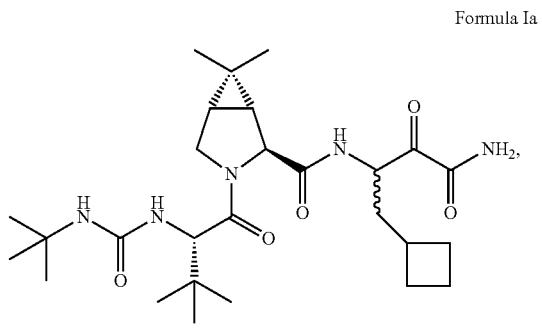

Formula Ia a pharmaceutically acceptable salt, solvate, or ester thereof.

The compound of Formula Ia has recently been separated into its isomer/diastereomers of Formula Ib and Ic, as disclosed in U.S. Patent Publication US2005/0249702 published Nov. 10, 2005. In one embodiment, at least one compound is Formula Ic (a potent inhibitor of HCV NS3 serine protease),

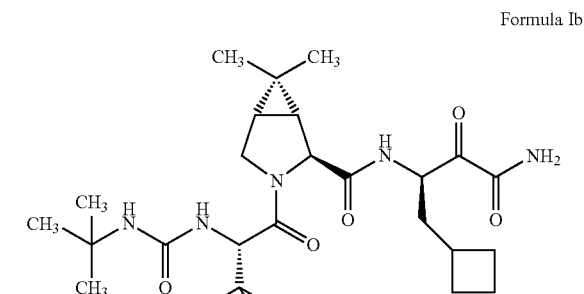

Formula Ib

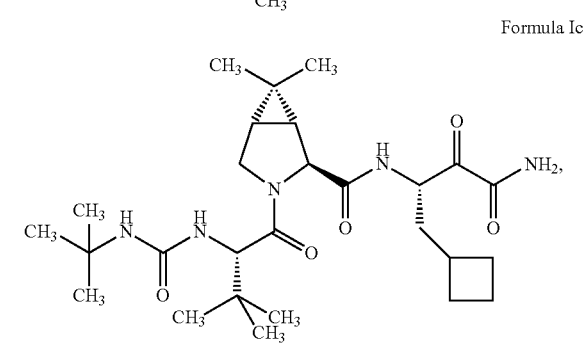

Formula Ic a pharmaceutically acceptable salt, solvate, or ester thereof. The chemical name of the compound of Formula Ic is (1R, 2S,5S)—N-[(1S)-3-amino-1-(cyclobutylmethyl)-2,3-dioxopropyl]-3-[(2S)-2-[[[(1,1-dimethylethyl)amino]-carbonyl]amino]-3,3-dimethyl-1-oxobutyl]-6,6-dimethyl-3-azabicyclo-[3.1.0]hexane-2-carboxamide.

Processes for making compounds of Formula I are disclosed in U.S. Patent Publication Nos. 2005/0059648, 2005/0020689 and 2005/0059800, incorporated by reference herein.

Non-limiting examples of suitable compounds of Formula II and methods of making the same are disclosed in WO02/08256 and in U.S. Pat. No. 6,800,434, at col. 5 through col. 247, incorporated herein by reference.

Non-limiting examples of suitable compounds of Formula III and methods of making the same are disclosed in International Patent Publication WO02/08187 and in U.S. Patent Publication 2002/0160962 at page 3, paragraph 22 through page 132, incorporated herein by reference.

Non-limiting examples of suitable compounds of Formula IV and methods of making the same are disclosed in International Patent Publication WO03/062228 and in U.S. Patent Publication 2003/0207861 at page 3, paragraph 25 through page 26, incorporated herein by reference.

Non-limiting examples of suitable compounds of Formula V and methods of making the same are disclosed in U.S. Patent Publication 2005/0119168 at page 3 paragraph [0024], through page 215, paragraph [0833], incorporated herein by reference.

Non-limiting examples of suitable compounds of Formula VI and methods of making the same are disclosed in U.S. Patent Publication Ser. No. 2005/0085425 at page 3, paragraph 0023 through page 139, incorporated herein by reference.

Non-limiting examples of suitable compounds of Formula VII, VIII, and IX as well as methods of making the same are disclosed in International Patent Publication WO 2005/051980 and in U.S. Patent Publication 2005/0164921 at page 3, paragraph [0026] through page 113, paragraph [0271], incorporated herein by reference.

Non-limiting examples of suitable compounds of Formula X and methods of making the same are disclosed in International Patent Publication WO2005/085275 and in U.S. Patent Publication 2005/0267043 at page 4, paragraph [0026] through page 519, paragraph [0444], incorporated herein by reference.

Non-limiting examples of suitable compounds of Formula XI and methods of making the same are disclosed in International Patent Publication WO2005/087721 and in U.S. Patent Publication 2005/0288233 at page 3, paragraph [0026] through page 280, paragraph [0508], incorporated herein by reference.

Non-limiting examples of suitable compounds of Formula XII and methods of making the same are disclosed in International Patent Publication WO2005/087725 and in U.S. Patent Publication 2005/0245458 at page 4, paragraph [0026] through page 194, paragraph [0374], incorporated herein by reference.

Non-limiting examples of suitable compounds of Formula XIII and methods of making the same are disclosed in International Patent Publication WO2005/085242 and in U.S. Patent Publication 2005/0222047 at page 3, paragraph [0026] through page 209, paragraph [0460], incorporated herein by reference.

Non-limiting examples of suitable compounds of Formula XIV and methods of making the same are disclosed in International Patent Publication WO2005/087731 at page 8, line 20 through page 683, line 6, incorporated herein by reference.

Non-limiting examples of suitable compounds of Formula XV and methods of making the same are disclosed in International Patent Publication WO2005/058821 and in U.S. Patent Publication 2005/0153900 at page 4, paragraph [0028] through page 83, paragraph [0279], incorporated herein by reference.

Non-limiting examples of suitable compounds of Formula XVI and methods of making the same are disclosed in International Patent Publication WO2005/087730 and in U.S. Patent Publication 2005/0197301 at page 3, paragraph [0026] through page 156, paragraph [0312], incorporated herein by reference.

Non-limiting examples of suitable compounds of Formula XVII and methods of making the same are disclosed in International Patent Publication WO2005/085197 and in U.S. Patent Publication 2005/0209164 at page 3, paragraph [0026] through page 87, paragraph [0354], incorporated herein by reference.

Non-limiting examples of suitable compounds of Formula XVIII and methods of making the same are disclosed in U.S. Patent Publication 2006/0046956 at page 4, paragraph [0024] through page 50, paragraph [0282], incorporated herein by reference.

Non-limiting examples of suitable compounds of Formula XIX and methods of making the same are disclosed in International Patent Publication WO2005/113581 and in U.S. Patent Publication 2005/0272663 at page 3, paragraph [0026] through page 76, incorporated herein by reference.

Non-limiting examples of suitable compounds of Formula XX and methods of making the same are disclosed in International Patent Publication WO2000/09558 at page 4, line 17 through page 85, incorporated herein by reference.

Non-limiting examples of suitable compounds of Formula XXI and methods of making the same are disclosed in International Patent Publication WO2000/09543 at page 4, line 14 through page 124, incorporated herein by reference.

Non-limiting examples of suitable compounds of Formula XXII and methods of making the same are disclosed in International Patent Publication WO2000/59929 and in U.S. Pat. No. 6,608,027, at col. 65, line 65 through col. 141, line 20, each incorporated herein by reference.

Non-limiting examples of suitable compounds of Formula XXIII and methods of making the same are disclosed in International Patent Publication WO02/18369 at page 4, line 4 through page 311, incorporated herein by reference.

Non-limiting examples of suitable compounds of Formula XXIV and methods of making the same are disclosed in U.S. Patent Publication No. 2002/0032175, 2004/0266731 and U.S. Pat. No. 6,265,380 at col. 3, line 35 through col. 121 and U.S. Pat. No. 6,617,309 at col. 3, line 40 through col. 121, each incorporated herein by reference.

Non-limiting examples of suitable compounds of Formula XXV and methods of making the same are disclosed in International Patent Publication WO1998/22496 at page 3 through page 122, incorporated herein by reference.

Non-limiting examples of suitable compounds of Formula XXVI and methods of making the same are disclosed in U.S. Pat. No. 6,143,715 at col. 3, line 6 through col. 62, line 20, incorporated herein by reference.

Non-limiting examples of suitable compounds of Formula XXVII and Formula XXVIII as well as methods of making the same are disclosed in International Patent Publication WO02/18369 at page 4, line 4 through page 311, incorporated herein by reference. More specifically, see International Patent Publication WO02/18369, Examples 17, 27, 86, and 126, incorporated herein by reference. In particular, for compound XXVII, see WO02/18369, Example 27 on pages 146-153 which details methods of making compound "CU" illustrated at page 90, and Example 126 which details methods of making the intermediate compound cxxxviii at page 225. Likewise, for compound XXVIIIa, see WO02/18369, Example 17 on pages 139-140 which details methods of making compound "BW" illustrated at page 52, and Example 86 which details methods of making the intermediate compound lxxxix at page 207.

For each of the above-listed alternative compounds, isomers of the various compounds (where they exist), including enantiomers, stereoisomers, rotamers, tautomers and racemates are also contemplated as being part of this invention, including mixtures of stereoisomers and racemic mixtures thereof.

There follows a description of the structure of the compounds of Formulae I to XXVIII.

The compound of structural Formula I has the structure

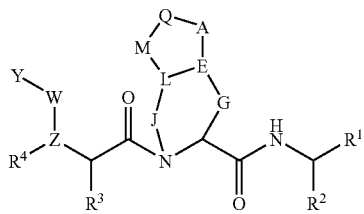

and includes pharmaceutically acceptable salts, solvates, or esters thereof;
wherein in Formula I:

Y is selected from the group consisting of the following moieties: alkyl, alkyl-aryl, heteroalkyl, heteroaryl, aryl-heteroaryl, alkyl-heteroaryl, cycloalkyl, alkyloxy, alkyl-aryloxy, aryloxy, heteroaryloxy, heterocycloalkyloxy, cycloalkyloxy, alkylamino, arylamino, alkyl-arylamino, arylamino, heteroarylamino, cycloalkylamino and heterocycloalkylamino, with the proviso that Y maybe optionally substituted with $X^{11}$ or $X^{12}$;

$X^{11}$ is alkyl, alkenyl, alkynyl, cycloalkyl, cycloalkyl-alkyl, heterocyclyl, heterocyclylalkyl, aryl, alkylaryl, arylalkyl, heteroaryl, alkylheteroaryl, or heteroarylalkyl, with the proviso that $X^{11}$ may be additionally optionally substituted with $X^{12}$;

$X^{12}$ is hydroxy, alkoxy, aryloxy, thio, alkylthio, arylthio, amino, alkylamino, arylamino, alkylsulfonyl, arylsulfonyl, alkylsulfonamido, arylsulfonamido, carboxy, carbalkoxy, carboxamido, alkoxycarbonylamino, alkoxycarbonyloxy, alkylureido, arylureido, halogen, cyano, or nitro, with the proviso that said alkyl, alkoxy, and aryl may be additionally optionally substituted with moieties independently selected from $X^{12}$;

$R^1$ is $COR^5$, wherein $R^5$ is $COR^7$ wherein $R^7$ is $NHR^9$, wherein $R^9$ is selected from the group consisting of H, alkyl, aryl, heteroalkyl, heteroaryl, cycloalkyl, cycloalkyl, arylalkyl, heteroarylalkyl, $[CH(R^{1\prime})]_pCOOR^{11}$,$[CH(R^{1\prime})]_pCONR^{12}R^{13}$,$[CH(R^{1\prime})]_pSO_2R^{11}$,$[CH(R^{1\prime})]_pCOR^{11}$,$[CH(R^{1\prime})]_pCH(OH)R^{11}$,$CH(R^{1\prime})CONHCH(R^{2\prime})COOR^{11}$,$CH(R^{1\prime})CONHCH(R^{2\prime})CON R^{12}R^{13}$,$CH(R^{1\prime})CONHCH(R^{2\prime})R^{\prime}$, $CH(R^{1\prime})CONHCH(R^{2\prime})CONHCH(R^{3\prime})COOR^{11}$,$CH(R^{1\prime})CONHCH(R^{2\prime})CONHCH(R^{3\prime})CONR^{12}R^{13}$,$CH(R^{1\prime})CONHCH(R^{2\prime})CONHCH(R^{3\prime})CONHCH(R^{4\prime})COOR^{11}$,$CH(R^{1\prime})CONHCH(R^{2\prime})CONHCH(R^{3\prime})CONHCH(R^{4\prime})CONR^{12}R^{13}$,$CH(R^{1\prime})CONHCH(R^{2\prime})CONHCH(R^{3\prime})CONHCH(R^{4\prime})CONHCH(R^{5\prime})COOR^{11}$ and $CH(R^{1\prime})CONHCH(R^{2\prime})CONHCH(R^{3\prime})CONHCH(R^{4\prime})CONHCH(R^{5\prime})CONR^{12}R^{13}$, wherein $R^{1\prime}$, $R^{2\prime}$, $R^{3\prime}$, $R^{4\prime}$, $R^{5\prime}$, $R^{11}$, $R^{12}$, $R^{13}$, and $R^{\prime}$ are independently selected from the group consisting of H, alkyl, aryl, heteroalkyl, heteroaryl, cycloalkyl, alkyl-aryl, alkyl-heteroaryl, aryl-alkyl and heteroaralkyl;

Z is selected from O, N, CH or CR;

W maybe present or absent, and if W is present, W is selected from C=O, C=S, C(=N—CN), or $SO_2$;

Q maybe present or absent, and when Q is present, Q is CH, N, P, $(CH_2)_p$, $(CHR)_p$, $(CRR')_p$, O, NR, S, or $SO_2$; and when 0 is absent, M may be present or absent; when 0 and M are absent, A is directly linked to L;

A is O, $CH_2$, (CHR) p, (CHR—CHR') p, (CRR') p, NR, S, $SO_2$ or a bond;

E is CH, N, CR, or a double bond towards A, L or G;

G may be present or absent, and when G is present, G is $(CH_2)_p$, (CHR) p, or $(CRR')_p$; and when G is absent, J is present and E is directly connected to the carbon atom in Formula I as G is linked to;

J maybe present or absent, and when J is present, J is $(CH_2)_p$, $(CHR)_p$, or $(CRR')_p$, $SO_2$, NH, NR or O; and when J is absent, G is present and E is directly linked to N shown in Formula I as linked to J;

L may be present or absent, and when L is present, L is CH, CR, O, S or NR; and when L is absent, then M may be present or absent; and if M is present with L being absent, then M is directly and independently linked to E, and J is directly and independently linked to E;

M may be present or absent, and when M is present, M is O, NR, S, $SO_2$, $(CH_2)_p$, $(CHR)_p(CHR—CHR')_p$, or $(CRR')_p$;

p is a number from 0 to 6; and

R, R', $R^2$, $R^3$ and $R^4$ are independently selected from the group consisting of H; $C_1$-$C_{10}$ alkyl; $C_2$-$C_{10}$ alkenyl; $C_3$-$C_8$ cycloalkyl; $C_3$-$C_8$ heterocycloalkyl, alkoxy, aryloxy, alkylthio, arylthio, amino, amido, ester, carboxylic acid, carbamate, urea, ketone, aldehyde, cyano, nitro, halogen; (cycloalkyl)alkyl and (heterocycloalkyl)alkyl, wherein said cycloalkyl is made of three to eight carbon atoms, and zero to six oxygen, nitrogen, sulfur, or phosphorus atoms, and said alkyl is of one to six carbon atoms; aryl; heteroaryl; alkyl-aryl; and alkyl-heteroaryl;

wherein said alkyl, heteroalkyl, alkenyl, heteroalkenyl, aryl, heteroaryl, cycloalkyl and heterocycloalkyl moieties may be optionally and chemically-suitably substituted, with said term "substituted" referring to optional and chemically-suitable substitution with one or more moieties selected from the group consisting of alkyl, alkenyl, alkynyl, aryl, aralkyl, cycloalkyl, heterocyclic, halogen, hydroxy, thio, alkoxy, aryloxy, alkylthio, arylthio, amino, amido, ester, carboxylic acid, carbamate, urea, ketone, aldehyde, cyano, nitro, sulfonamido, sulfoxide, sulfone, sulfonyl urea, hydrazide, and hydroxamate;

further wherein said unit N-C-G-E-L-J-N represents a five-membered or six-membered cyclic ring structure with the proviso that when said unit N-C-G-E-L-J-N represents a five-membered cyclic ring structure, or when the bicyclic ring structure in Formula I comprising N, C, G, E, L, J, N, A, Q, and M represents a five-membered cyclic ring structure, then said five-membered cyclic ring structure lacks a carbonyl group as part of the cyclic ring.

The compound of structural Formula II has the structure:

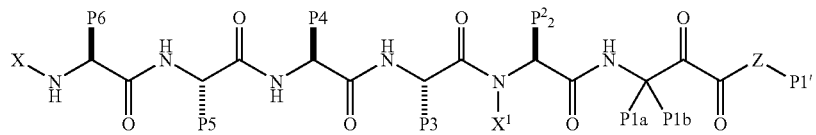

or a pharmaceutically acceptable salt, solvate, or ester thereof;
wherein in Formula II:
Z is NH;
X is alkylsulfonyl, heterocyclylsulfonyl, heterocyclylalkylsulfonyl, arylsulfonyl, heteroarylsulfonyl, alkylcarbonyl, heterocyclylcarbonyl, heterocyclylalkylcarbonyl, arylcarbonyl, heteroarylcarbonyl, alkoxycarbonyl, heterocyclyloxycarbonyl, aryloxycarbonyl, heteroaryloxycarbonyl, alkylaminocarbonyl, heterocyclylaminocarbonyl, arylaminocarbonyl, or heteroarylaminocarbonyl moiety, with the proviso that X may be additionally optionally substituted with $R^{12}$ or $R^{13}$;
$X^1$ is H; $C_1$-$C_4$ straight chain alkyl; $C_1$-$C_4$ branched alkyl or; $CH_2$-aryl (substituted or unsubstituted);
$R^{12}$ is alkyl, alkenyl, alkynyl, cycloalkyl, cycloalkyl-alkyl, heterocyclyl, heterocyclylalkyl, aryl, alkylaryl, arylalkyl, heteroaryl, alkylheteroaryl, or heteroarylalkyl moiety, with the proviso that $R^{12}$ may be additionally optionally substituted with $R^{13}$.
$R^{13}$ is hydroxy, alkoxy, aryloxy, thio, alkylthio, arylthio, amino, alkylamino, arylamino, alkylsulfonyl, arylsulfonyl, alkylsulfonamido, arylsulfonamido, carboxy, carbalkoxy, carboxamido, alkoxycarbonylamino, alkoxycarbonyloxy, alkylureido, arylureido, halogen, cyano, or nitro moiety, with the proviso that the alkyl, alkoxy, and aryl may be additionally optionally substituted with moieties independently selected from $R^{13}$.
P1a, P1b, P2, P3, P4, P5, and P6 are independently: H; C1-C10 straight or branched chain alkyl; C2-C10 straight or branched chain alkenyl; C3-C8 cycloalkyl, C3-C8 heterocyclic; (cycloalkyl)alkyl or (heterocyclyl)alkyl, wherein said cycloalkyl is made up of 3 to 8 carbon atoms, and zero to 6 oxygen, nitrogen, sulfur, or phosphorus atoms, and said alkyl is of 1 to 6 carbon atoms; aryl, heteroaryl, arylalkyl, or heteroarylalkyl, wherein said alkyl is of 1 to 6 carbon atoms;
wherein said alkyl, alkenyl, cycloalkyl, heterocyclyl; (cycloalkyl)alkyl and (heterocyclyl)alkyl moieties may be optionally substituted with $R^{13}$, and further wherein said P1a and P1b may optionally be joined to each other to form a spirocyclic or spiroheterocyclic ring, with said spirocyclic or spiroheterocyclic ring containing zero to six oxygen, nitrogen, sulfur, or phosphorus atoms, and may be additionally optionally substituted with $R^{13}$; and
P1' is H, alkyl, alkenyl, alkynyl, cycloalkyl, cycloalkyl-alkyl, heterocyclyl, heterocyclyl-alkyl, aryl, aryl-alkyl, heteroaryl, or heteroaryl-alkyl; with the proviso that said P1' may be additionally optionally substituted with $R^{13}$.
The compound of Structural Formula III has the structure:

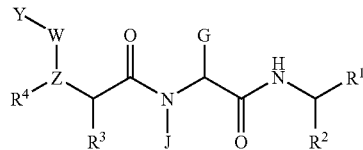

or a pharmaceutically acceptable salt, solvate, or ester thereof;
wherein in Formula III:
G is carbonyl;
J and Y may be the same or different and are independently selected from the group consisting of the moieties: H, alkyl, alkyl-aryl, heteroalkyl, heteroaryl, aryl-heteroaryl, alkyl-heteroaryl, cycloalkyl, alkyloxy, alkyl-aryloxy, aryloxy, heteroaryloxy, heterocycloalkyloxy, cycloalkyloxy, alkylamino, arylamino, alkyl-arylamino, arylamino, heteroarylamino, cycloalkylamino and heterocycloalkylamino, with the proviso that Y maybe additionally optionally substituted with $X^{11}$ or $X^{12}$;
$X^{11}$ is selected from the group consisting of alkyl, alkenyl, alkynyl, cycloalkyl, cycloalkyl-alkyl, heterocyclyl, heterocyclylalkyl, aryl, alkylaryl, arylalkyl, heteroaryl, alkylheteroaryl, or heteroarylalkyl moiety, with the proviso that $X^{11}$ may be additionally optionally substituted with $X^{12}$;
$X^{12}$ is hydroxy, alkoxy, aryloxy, thio, alkylthio, arylthio, amino, alkylamino, arylamino, alkylsulfonyl, arylsulfonyl, alkylsulfonamido, arylsulfonamido, carboxy, carbalkoxy, carboxamido, alkoxycarbonylamino, alkoxycarbonyloxy, alkylureido, arylureido, halogen, cyano, or nitro, with the proviso that said alkyl, alkoxy, and aryl may be additionally optionally substituted with moieties independently selected from $X^{12}$;
$R^1$ is $COR^5$ or $C(OR)_2$, wherein $R^5$ is selected from the group consisting of H, OH, $OR^8$, $NR^9R^{10}$, $CF_3$, $C_2F_5$, $C_3F_7$, $CF_2R^6$, $R^6$ and $COR^7$ wherein $R^7$ is selected from the group consisting of H, OH, $OR^8$, $CHR^9R^{10}$, and $NR^9R^{10}$, wherein $R^6$, $R^8$, $R^9$ and $R^{10}$ may be the same or different and are independently selected from the group consisting of H, alkyl, aryl, heteroalkyl, heteroaryl, cycloalkyl, cycloalkyl, arylalkyl, heteroarylalkyl, $CH(R^{1'})COOR^{11}$, $CH(R^{1'})CONR^2R^3$, $CH(R^{1'})CONHCH(R^{2'})COOR^{11}$, $CH(R^{1'})CONHCH(R^{2'})CONR^{12}R^{13}$, $CH(R^{1'})CONHCH(R^{2'})R'$, $CH(R^{1'})CONHCH(R^{2'})CONHCH(R^{3'})COOR^{11}$, $CH(R^{1'})CONHCH(R^{2'})CONHCH(R^{3'})CONR^{12}R^{13}$, $CH(R^{1'})CONHCH(R^{2'})CONHCH(R^{3'})CONHCH(R^{4'})COOR^{11}$, $CH(R^{1'})CONHCH(R^{2'})CONHCH(R^{3'})CONHCH(R^{4'})CONR^{12}R^{13}$, $CH(R^{1'})CONHCH(R^{2'})CONHCH(R^{3'})CONHCH(R^{4'})CONHCH(R^{5'})COOR^{11}$, and $CH(R^{1'})CONHCH(R^{2'})CONHCH(R^{3'})CONHCH(R^{4'})CONHCH(R^{5'})$ $CONR^{12}R^{13}$, wherein $R^{1'}$, $R^{2'}$, $R^{3'}$, $R^{4'}$, $R^{5'}$, $R^{11}$, $R^{12}$, $R^{13}$, and R' may be the same or different and are independently selected from a group consisting of H, alkyl, aryl, heteroalkyl, heteroaryl, cycloalkyl, alkyl-aryl, alkyl-heteroaryl, aryl-alkyl and heteroaralkyl;
Z is selected from O, N, or CH;
W maybe present or absent, and if W is present, W is selected from C=O, C=S, or $SO_2$; and
R, R', $R^2$, $R^3$ and $R^4$ are independently selected from the group consisting of H; C1-C10 alkyl; C2-C10 alkenyl; C3-C8 cycloalkyl; C3-C8 heterocycloalkyl, alkoxy, aryloxy, alkylthio, arylthio, amino, amido, ester, carboxylic acid, carbamate, urea, ketone, aldehyde, cyano, nitro; oxygen, nitrogen, sulfur, or phosphorus atoms (with said oxygen, nitrogen, sulfur, or phosphorus atoms numbering zero to six); (cycloalkyl)alkyl and (heterocycloalkyl)alkyl, wherein said cycloalkyl is made of three to eight carbon atoms, and zero to six oxygen, nitrogen, sulfur, or phosphorus atoms, and said alkyl is of one to six carbon atoms; aryl; heteroaryl; alkyl-aryl; and alkyl-heteroaryl;
wherein said alkyl, heteroalkyl, alkenyl, heteroalkenyl, aryl, heteroaryl, cycloalkyl and heterocycloalkyl moieties may be optionally substituted, with said term "substituted" referring to optional and chemically-suitable substitution with one or more moieties selected from the group consisting of alkyl, alkenyl, alkynyl, aryl, aralkyl, cycloalkyl, heterocyclic, halogen, hydroxy, thio, alkoxy, aryloxy, alkylthio, arylthio, amino, amido, ester, carboxylic acid, carbamate, urea, ketone, aldehyde, cyano, nitro, sulfonamide, sulfoxide, sulfone, sulfonylurea, hydrazide, and hydroxamate.

The compound of Structural Formula IV has the structure:

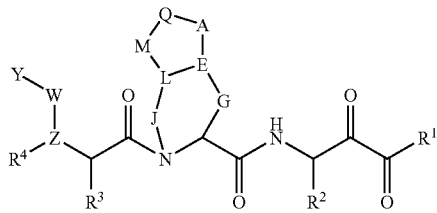

or a pharmaceutically acceptable salt, solvate, or ester thereof;

wherein in Formula IV:

Y is selected from the group consisting of the following moieties: alkyl, alkyl-aryl, heteroalkyl, heteroaryl, aryl-heteroaryl, alkyl-heteroaryl, cycloalkyl, alkyloxy, alkyl-aryloxy, aryloxy, heteroaryloxy, heterocycloalkyloxy, cycloalkyloxy, alkylamino, arylamino, alkyl-arylamino, arylamino, heteroarylamino, cycloalkylamino and heterocycloalkylamino, with the proviso that Y maybe optionally substituted with $X^{11}$ or $X^{12}$;

$X^{11}$ is alkyl, alkenyl, alkynyl, cycloalkyl, cycloalkyl-alkyl, heterocyclyl, heterocyclylalkyl, aryl, alkylaryl, arylalkyl, heteroaryl, alkylheteroaryl, or heteroarylalkyl, with the proviso that $X^{11}$ may be additionally optionally substituted with $X^{12}$;

$X^{12}$ is hydroxy, alkoxy, aryloxy, thio, alkylthio, arylthio, amino, alkylamino, arylamino, alkylsulfonyl, arylsulfonyl, alkylsulfonamido, arylsulfonamido, carboxyl, carbalkoxy, carboxamido, alkoxycarbonylamino, alkoxycarbonyloxy, alkylureido, arylureido, halogen, cyano, or nitro, with the proviso that said alkyl, alkoxy, and aryl may be additionally optionally substituted with moieties independently selected from $X^{12}$;

$R^1$ is selected from the following structures:

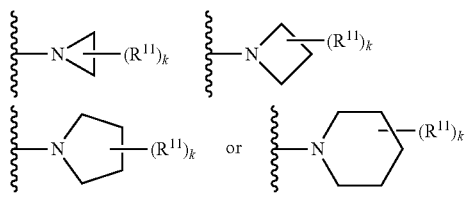

wherein k is a number from 0 to 5, which can be the same or different, $R^{11}$ denotes optional substituents, with each of said substituents being independently selected from the group consisting of alkyl, alkenyl, alkynyl, aryl, cycloalkyl, alkyl-aryl, heteroalkyl, heteroaryl, aryl-heteroaryl, alkyl-heteroaryl, alkyloxy, alkyl-aryloxy, aryloxy, heteroaryloxy, heterocycloalkyloxy, cycloalkyloxy, alkylamino, arylamino, alkyl-arylamino, arylamino, heteroarylamino, cycloalkylamino, heterocycloalkylamino, hydroxy, thio, alkylthio, arylthio, amino, alkylsulfonyl, arylsulfonyl, alkylsulfonamido, arylsulfonamido, carboxyl, carbalkoxy, carboxamido, alkoxycarbonylamino, alkoxycarbonyloxy, alkylureido, arylureido, halogen, cyano, and nitro, with the proviso that $R^{11}$ (when $R^{11} \neq H$) maybe optionally substituted with $X^{11}$ or $X^{12}$;

Z is selected from O, N, CH or CR;

W may be present or absent, and if W is present, W is selected from C=O, C=S, C(=N—CN), or $S(O_2)$;

Q may be present or absent, and when Q is present, Q is CH, N, P, $(CH_2)_p$, $(CHR)_p$, $(CRR')_p$, O, N(R), S, or $S(O_2)$; and when Q is absent, M may be present or absent; when Q and M are absent, A is directly linked to L;

A is O, $CH_2$, $(CHR)_p$, $(CHR-CHR')_p$, $(CRR')_p$, N(R), S, $S(O_2)$ or a bond;

E is CH, N, CR, or a double bond towards A, L or G;

G may be present or absent, and when G is present, G is $(CH_2)_p$, $(CHR)_p$, or $(CRR')_p$; and when G is absent, J is present and E is directly connected to the carbon atom in Formula I as G is linked to;

J may be present or absent, and when J is present, J is $(CH_2)_p$, $(CHR)_p$, or $(CRR')_p$, $S(O_2)$, NH, N(R) or O; and when J is absent, G is present and E is directly linked to N shown in Formula I as linked to J; L may be present or absent, and when L is present, L is CH, C(R), O, S or N(R); and when L is absent, then M may be present or absent; and if M is present with L being absent, then M is directly and independently linked to E, and J is directly and independently linked to E;

M may be present or absent, and when M is present, M is O, N(R), S, $S(O_2)$, $(CH_2)_p$, $(CHR)_p(CHR-CHR')_p$, or $(CRR')_p$;

p is a number from 0 to 6; and

R, R', $R^2$, $R^3$ and $R^4$ can be the same or different, each being independently selected from the group consisting of H; $C_1$-$C_{10}$ alkyl; $C_2$-$C_{10}$ alkenyl; $C_3$-$C_8$ cycloalkyl; $C_3$-$C_8$ heterocycloalkyl, alkoxy, aryloxy, alkylthio, arylthio, amino, amido, ester, carboxylic acid, carbamate, urea, ketone, aldehyde, cyano, nitro, halogen, (cycloalkyl)alkyl and (heterocycloalkyl)alkyl, wherein said cycloalkyl is made of three to eight carbon atoms, and zero to six oxygen, nitrogen, sulfur, or phosphorus atoms, and said alkyl is of one to six carbon atoms; aryl; heteroaryl; alkyl-aryl; and alkyl-heteroaryl;

wherein said alkyl, heteroalkyl, alkenyl, heteroalkenyl, aryl, heteroaryl, cycloalkyl and heterocycloalkyl moieties may be optionally substituted, with said term "substituted" referring to substitution with one or more moieties which can be the same or different, each being independently selected from the group consisting of alkyl, alkenyl, alkynyl, aryl, aralkyl, cycloalkyl, heterocyclic, halogen, hydroxy, thio, alkoxy, aryloxy, alkylthio, arylthio, amino, amido, ester, carboxylic acid, carbamate, urea, ketone, aldehyde, cyano, nitro, sulfonamido, sulfoxide, sulfone, sulfonyl urea, hydrazide, and hydroxamate;

further wherein said unit N-C-G-E-L-J-N represents a five-membered cyclic ring structure or six-membered cyclic ring structure with the proviso that when said unit N-C-G-E-L-J-N represents a five-membered cyclic ring structure, or when the bicyclic ring structure in Formula I comprising N, C, G, E, L, J, N, A, Q, and M represents a five-membered cyclic ring structure, then said five-membered cyclic ring structure lacks a carbonyl group as part of said five-membered cyclic ring.

The compound of Structural Formula V has the structure:

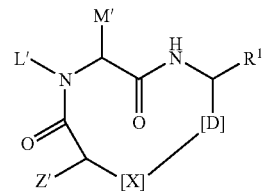

or a pharmaceutically acceptable salt, solvate, or ester thereof;

wherein in Formula V:

(1) $R^1$ is —C(O)$R^5$ or —B(OR)$_2$;

(2) $R^5$ is H, —OH, —OR$^8$, —NR$^9$R$^{10}$, —C(O)OR$^8$, —C(O)NR$^9$R$^{10}$, —CF$_3$, —C$_2$F$_5$, C$_3$F$_7$, —CF$_2$R$^6$, —R$^6$, —C(O)R$^7$ or NR$^7$SO$_2$R$^8$;

(3) $R^7$ is H, —OH, —OR$^8$, or —CHR$^9$R$^{10}$, (4) $R^6$, $R^8$, $R^9$ and $R^{10}$ are independently selected from the group consisting of H: alkyl, alkenyl, aryl, heteroalkyl, heteroaryl, cycloalkyl, arylalkyl, heteroarylalkyl, $R^{14}$, —CH(R$^{1'}$)CH(R$^{1'}$)C(O)OR$^{11}$,[CH(R$^{1'}$)]$_p$C(O)OR$^{11}$, —[CH(R$^{1'}$)]$_p$C(O)NR$^{12}$R$^{13}$, —[CH(R$^{1'}$)]$_p$S(O$_2$)R$^{11}$, —[CH(R$^{1'}$)]$_p$C(O)R$^{11}$, —[CH(R$^{1'}$)]$_p$S(O$_2$)NR$^{12}$R$^{13}$, CH(R$^{1'}$)C(O)N(H)CH(R$^{2'}$)(R'), CH(R$^{1'}$)CH(R$^{1'}$)C(O)NR$^{12}$R$^{13}$, —CH(R$^{1'}$)CH(R$^{1'}$)S(O$_2$)R$^{11}$, —CH(R$^{1'}$)CH(R$^{1'}$)S(O$_2$)NR$^{12}$R$^{13}$, —CH(R$^{1'}$)CH(R$^{1'}$)C(O)R$^{11}$, —[CH(R$^{1'}$)]$_p$CH(OH)R$^{11}$, —CH(R$^{1}$)C(O)N(H)CH(R$^{2'}$)C(O)OR$^{11}$, C(O)N(H)CH(R$^{2'}$)C(O)OR$^{11}$, —C(O)N(H)CH(R$^{2'}$)C(O)R$^{11}$,CH(R$^{1'}$)C(O)N(H)CH(R$^{2'}$)C(O)NR$^{12}$R$^{13}$, —CH(R$^{1'}$)C(O)N(H)CH(R$^{2'}$)R',CH(R$^{1'}$)C(O)N(H)CH(R$^{2'}$)C(O)N(H) CH(R$^{3'}$)C(O)OR$^{11}$,CH(R$^{1'}$)C(O)N(H)CH(R$^{2'}$)C(O)CH(R$^{3'}$)NR$^{12}$R$^{13}$,CH(R$^{1'}$)C(O) N(H)CH(R$^{2'}$)C(O)N(H)CH(R$^{3'}$)C(O)NR$^{12}$R$^{13}$,CH(R$^{1'}$)C(O)N(H)CH(R$^{2'}$)C(O)N(H) CH(R$^{3'}$)C(O)N(H)CH(R$^{4'}$)C(O)OR$^{11}$, H(R$^{1'}$)C(O)N(H)CH(R$^{2'}$)C(O)N(H)CH(R$^{3'}$)C(O)N(H)CH (R$^{4'}$)C(O)NR$^{12}$R$^{13}$, CH(R$^{1'}$)C(O)N(H)CH(R$^{2'}$)C(O)N(H) CH(R$^{3'}$)C(O)N(H)CH(R$^{4'}$)C(O)N(H)CH(R$^{5'}$)C(O)OR$^{11}$, and CH(R$^{1'}$)C(O)N(H)CH(R$^{2'}$)C(O)N(H)CH(R$^{3'}$)C(O)N (H)CH(R$^{4'}$)C(O)N(H)CH(R$^{5'}$)C(O)NR$^{12}$R$^{13}$;

wherein R$^{1'}$, R$^{2'}$, R$^{3'}$, R$^{4'}$, R$^{5'}$, R$^{11}$, R$^{12}$ and R$^{13}$ can be the same or different, each being independently selected from the group consisting of: H, halogen, alkyl, aryl, heteroalkyl, heteroaryl, cycloalkyl, alkoxy, aryloxy, alkenyl, alkynyl, alkyl-aryl, alkyl-heteroaryl, heterocycloalkyl, aryl-alkyl and heteroaralkyl; or R$^{12}$ and R$^{13}$ are linked together wherein the combination is cycloalkyl, heterocycloalkyl, ary or heteroaryl;

R$^{14}$ is present or not and if present is selected from the group consisting of: H, alkyl, aryl, heteroalkyl, heteroaryl, cycloalkyl, alkyl-aryl, allyl, alkyl-heteroaryl, alkoxy, aryl-alkyl, alkenyl, alkynyl and heteroaralkyl;

(5) R and R' are present or not and if present can be the same or different, each being independently selected from the group consisting of: H, OH, C$_1$-C$_{10}$ alkyl, C$_2$-C$_{10}$ alkenyl, C$_3$-C$_8$ cycloalkyl, C$_3$-C$_8$ heterocycloalkyl, alkoxy, aryloxy, alkylthio, arylthio, alkylamino, arylamino, amino, amido, arylthioamino, arylcarbonylamino, arylaminocarboxy, alkylaminocarboxy, heteroalkyl, alkenyl, alkynyl, (aryl) alkyl, heteroarylalkyl, ester, carboxylic acid, carbamate, urea, ketone, aldehyde, cyano, nitro, halogen, (cycloalkyl) alkyl, aryl, heteroaryl, (alkyl)aryl, alkylheteroaryl, alkyl-heteroaryl and (heterocycloalkyl)alkyl, wherein said cycloalkyl is made of three to eight carbon atoms, and zero to six oxygen, nitrogen, sulfur, or phosphorus atoms, and said alkyl is of one to six carbon atoms;

(6) L' is H, OH, alkyl, heteroalkyl, aryl, heteroaryl, cycloalkyl, or heterocyclyl;

(7) M' is H, alkyl, heteroalkyl, aryl, heteroaryl, cycloalkyl, arylalkyl, heterocyclyl or an amino acid side chain;

or L' and M' are linked together to form a ring structure wherein the portion of structural Formula 1 represented by:

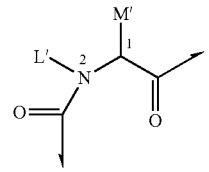

and wherein structural Formula 2 is represented by:

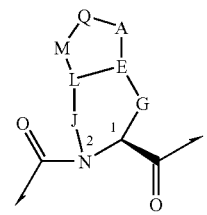

wherein in Formula 2:

E is present or absent and if present is C, CH, N or C(R);

J is present or absent, and when J is present, J is (CH$_2$)$_p$, (CHR—CHR')$_p$, (CHR)$_p$, (CRR')$_p$, S(O$_2$), N(H), N(R) or O; when J is absent and G is present, L is directly linked to the nitrogen atom marked position 2;

p is a number from 0 to 6;

L is present or absent, and when L is present, L is C(H) or C(R); when L is absent, M is present or absent; if M is present with L being absent, then M is directly and independently linked to E, and J is directly and independently linked to E;

G is present or absent, and when G is present, G is (CH$_2$)$_p$, (CHR)$_p$, (CHR—CHR')$_p$ or (CRR')$_p$; when G is absent, J is present and E is directly connected to the carbon atom marked position 1;

Q is present or absent, and when Q is present, Q is NR, PR, (CR═CR), (CH$_2$)$_p$, (CHR)$_p$, (CRR')$_p$, (CHR—CHR')$_p$, O, NR, S, SO, or SO$_2$; when Q is absent, M is (i) either directly linked to A or (ii) an independent substituent on L, said independent substituent being selected from —OR, —CH(R)(R'), S(O)$_{0-2}$R or —NRR' or (iii) absent; when both Q and M are absent, A is either directly linked to L, or A is an independent substituent on E, said independent substituent being selected from —OR, —CH(R)(R'), S(O)$_{0-2}$R or —NRR' or A is absent;

A is present or absent and if present A is O, O(R), (CH$_2$)$_p$, (CHR)$_p$, (CHR—CHR')$_p$, (CRR')$_p$, N(R), NRR', S, S(O$_2$), —OR, CH(R)(R') or NRR'; or A is linked to M to form an alicyclic, aliphatic or heteroalicyclic bridge;

M is present or absent, and when M is present, M is halogen, O, OR, N(R), S, S(O$_2$), (CH$_2$)$_p$, (CHR)$_p$ (CHR—CHR')$_p$, or (CRR')$_p$; or M is linked to A to form an alicyclic, aliphatic or heteroalicyclic bridge;

(8) Z' is represented by the structural Formula 3:

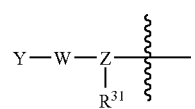

wherein in Formula 3:

Y is selected from the group consisting of: H, aryl, alkyl, alkyl-aryl, heteroalkyl, heteroaryl, aryl-heteroaryl, alkylheteroaryl, cycloalkyl, alkyloxy, alkyl-aryloxy, aryloxy, heteroaryloxy, heterocycloalkyloxy, heteroalkyl-heteroaryl, heteroalkyl-heterocycloalkyl, cycloalkyloxy, alkylamino, arylamino, alkyl-arylamino, arylamino, heteroarylamino, cycloalkylamino and heterocycloalkylamino, and Y is unsubstituted or optionally substituted with one or two substituents which are the same or different and are independently selected from $X^{11}$ or $X^{12}$;

$X^{11}$ is alkyl, alkenyl, alkynyl, cycloalkyl, cycloalkyl-alkyl, heterocyclyl, heterocyclylalkyl, aryl, alkylaryl, arylalkyl, heteroaryl, alkylheteroaryl, or heteroarylalkyl, and $X^{11}$ is unsubstituted or optionally substituted with one or more of $X^{12}$ moieties which are the same or different and are independently selected;

$X^{12}$ is hydroxy, alkoxy, alkyl, alkenyl, alkynyl, aryl, aryloxy, thio, alkylthio, arylthio, amino, alkylamino, arylamino, alkylsulfonyl, arylsulfonyl, alkylsulfonamido, arylsulfonamido, carboxy, carbalkoxy, carboxamido, alkylcarbonyl, arylcarbonyl, heteroalkylcarbonyl, heteroarylcarbonyl, sulfonylurea, cycloalkylsulfonamido, heteroarylcycloalkylsulfonamido, heteroaryl-sulfonamido, alkoxycarbonylamino, alkoxycarbonyloxy, alkylureido, arylureido, halogen, cyano, or nitro, and said alkyl, alkoxy, and aryl are unsubstituted or optionally independently substituted with one or more moieties which are the same or different and are independently selected from alkyl, alkenyl, alkynyl, cycloalkyl, cycloalkyl-alkyl, heterocyclyl, heterocyclylalkyl, aryl, alkylaryl, arylalkyl, heteroaryl, alkylheteroaryl, or heteroarylalkyl;

Z is O, N, C(H) or C(R);

$R^{31}$ is H, hydroxyl, aryl, alkyl, alkyl-aryl, heteroalkyl, heteroaryl, aryl-heteroaryl, alkyl-heteroaryl, cycloalkyl, alkyloxy, alkyl-aryloxy, aryloxy, heteroaryloxy, heterocycloalkyloxy, heteroalkyl-heteroaryl, cycloalkyloxy, alkylamino, arylamino, alkyl-arylamino, arylamino, heteroarylamino, cycloalkylamino or heterocycloalkylamino, and $R^{31}$ is unsubstituted or optionally substituted with one or two substituents which are the same or different and are independently selected from $X^{13}$ or $X^{14}$;

$X^{13}$ is alkyl, alkenyl, alkynyl, cycloalkyl, cycloalkyl-alkyl, heterocyclyl, heterocyclylalkyl, aryl, alkylaryl, arylalkyl, heteroaryl, alkylheteroaryl, or heteroarylalkyl, and $X^{13}$ is unsubstituted or optionally substituted with one or more of $X^{14}$ moieties which are the same or different and are independently selected;

$X^{14}$ is hydroxy, alkoxy, alkyl, alkenyl, alkynyl, aryl, aryloxy, thio, alkylthio, arylthio, amino, alkylamino, arylamino, alkylsulfonyl, arylsulfonyl, alkylsulfonamido, arylsulfonamido, carboxy, carbalkoxy, carboxamido, alkylcarbonyl, arylcarbonyl, heteroalkylcarbonyl, heteroarylcarbonyl, cycloalkylsulfonamido, heteroarylcycloalkylsulfonamido, heteroarylsulfonamido, alkoxycarbonylamino, alkoxycarbonyloxy, alkylureido, arylureido, halogen, cyano, or nitro, and said alkyl, alkoxy, and aryl are unsubstituted or optionally independently substituted with one or more moieties which are the same or different and are independently selected from alkyl, alkenyl, alkynyl, cycloalkyl, cycloalkyl-alkyl, heterocyclyl, heterocyclylalkyl, aryl, alkylaryl, arylalkyl, heteroaryl, alkylheteroaryl, or heteroarylalkyl;

W may be present or absent, and if W is present, W is C(=O), C(=S), C(=N—CN), or S(O$_2$);

(9) X is represented by structural Formula 4:

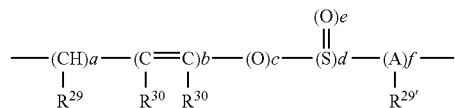

wherein in Formula 4:
a is 2, 3, 4, 5, 6, 7, 8 or 9;
b, c, d, e and f are 0, 1, 2, 3, 4 or 5;
A is C, N, S or O;
$R^{29}$ and $R^{29'}$ are independently present or absent and if present can be the same or different, each being independently one or two substituents independently selected from the group consisting of: H, halo, alkyl, aryl, cycloalkyl, cycloalkylamino, cycloalkylaminocarbonyl, cyano, hydroxy, alkoxy, alkylthio, amino, —NH(alkyl), —NH(cycloalkyl), —N(alkyl)$_2$, carboxyl, C(O)O-alkyl, heteroaryl, aralkyl, alkylaryl, aralkenyl, heteroaralkyl, alkylheteroaryl, heteroaralkenyl, hydroxyalkyl, aryloxy, aralkoxy, acyl, aroyl, nitro, aryloxycarbonyl, aralkoxycarbonyl, alkylsulfonyl, arylsulfonyl, heteroarylsulfonyl, alkylsulfinyl, arylsulfinyl, heteroarylsulfinyl, arylthio, heteroarylthio, aralkylthio, heteroaralkylthio, cycloalkenyl, heterocyclyl, heterocyclenyl, Y$_1$Y$_2$N-alkyl-, Y$_1$Y$_2$NC(O)— and Y$_1$Y$_2$NSO$_2$—, wherein Y$_1$ and Y$_2$ can be the same or different and are independently selected from the group consisting of hydrogen, alkyl, aryl, and aralkyl; or
$R^{29}$ and $R^{29'}$ are linked together such that the combination is an aliphatic or heteroaliphatic chain of 0 to 6 carbons;
$R^{30}$ is present or absent and if present is one or two substituents independently selected from the group consisting of: H, alkyl, aryl, heteroaryl and cylcoalkyl;

(10) D is represented by structural Formula 5:

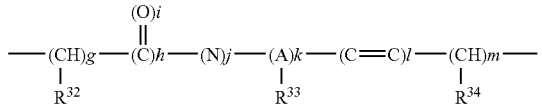

wherein in Formula 5:
$R^{32}$, $R^{33}$ and $R^{34}$ are present or absent and if present are independently one or two substituents independently selected from the group consisting of: H, halo, alkyl, aryl, cycloalkyl, cycloalkylamino, spiroalkyl, cycloalkylaminocarbonyl, cyano, hydroxy, alkoxy, alkylthio, amino, —NH(alkyl), —NH(cycloalkyl), —N(alkyl)$_2$, carboxyl, —C(O)O-alkyl, heteroaryl, aralkyl, alkylaryl, aralkenyl, heteroaralkyl, alkylheteroaryl, heteroaralkenyl, hydroxyalkyl, aryloxy, aralkoxy, acyl, aroyl, nitro, aryloxycarbonyl, aralkoxycarbonyl, alkylsulfonyl, arylsulfonyl, heteroarylsulfonyl, alkylsulfinyl, arylsulfinyl, heteroarylsulfinyl, arylthio, heteroarylthio, aralkylthio, heteroaralkylthio, cycloalkenyl, heterocyclyl, heterocyclenyl, Y$_1$Y$_2$N-alkyl-, Y$_1$Y$_2$NC(O)— and Y$_1$Y$_2$NSO$_2$—, wherein Y$_1$ and Y$_2$ can be the same or different and are independently selected from the group consisting of hydrogen, alkyl, aryl, and aralkyl; or
$R^{32}$ and $R^{34}$ are linked together such that the combination forms a portion of a cycloalkyl group;
g is 1, 2, 3, 4, 5, 6, 7, 8 or 9;
h, i, j, k, l and m are 0, 1, 2, 3, 4 or 5; and
A is C, N, S or O,

(11) provided that when structural Formula 2:

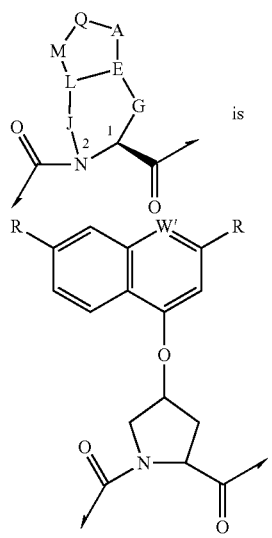

Formula 2 and

W' is CH or N, both the following conditional exclusions (i) and (ii) apply: conditional exclusion (i): Z' is not —NH—R$^{36}$, wherein R$^{36}$ is H, C$_{6 \text{ or } 10}$ aryl, heteroaryl, —C(O)—R$^{37}$, —C(O)—OR$^{37}$ or —C(O)—NHR$^{37}$, wherein R$^{37}$ is C$_{1-6}$ alkyl or C$_{3-6}$ cycloalkyl;

and conditional exclusion (ii): R$^1$ is not —C(O)OH, a pharmaceutically acceptable salt of —C(O)OH, an ester of —C(O)OH or —C(O)NHR$^{38}$ wherein R$^{38}$ is selected from the group consisting of C$_{1-8}$ alkyl, C$_{3-6}$ cycloalkyl, C$_{6 \text{ to } 10}$ aryl or C$_{7-16}$ aralkyl.

The compound of structural Formula VI has the structure,

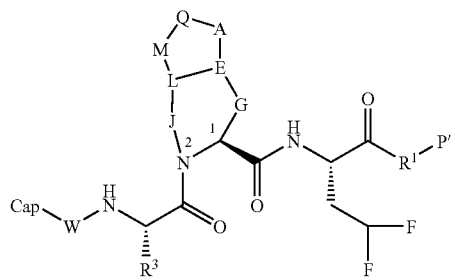

and includes pharmaceutically acceptable salts, solvates, or esters thereof;

wherein in Formula VI:

"Cap" is H, alkyl, alkyl-aryl, heteroalkyl, heteroaryl, arylheteroaryl, alkyl-heteroaryl, cycloalkyl, alkyloxy, alkylaryloxy, aryloxy, heteroaryloxy, heterocyclyloxy, cycloalkyloxy, amino, alkylamino, arylamino, alkyl-arylamino, arylamino, heteroarylamino, cycloalkylamino, carboxyalkylamino, arylalkyloxy or heterocyclylamino, wherein each of said alkyl, alkyl-aryl, heteroalkyl, heteroaryl, aryl-heteroaryl, alkyl-heteroaryl, cycloalkyl, alkyloxy, alkyl-aryloxy, aryloxy, heteroaryloxy, heterocyclyloxy, cycloalkyloxy, amino, alkylamino, arylamino, alkyl-arylamino, arylamino, heteroarylamino, cycloalkylamino, carboxyalkylamino, arylalkyloxy or heterocyclylamino can be unsubstituted or optionally independently substituted with one or two substituents which can be the same or different and are independently selected from X$^1$ and X$^2$;

P' is —NHR;

X$^1$ is alkyl, alkenyl, alkynyl, cycloalkyl, cycloalkyl-alkyl, heterocyclyl, heterocyclylalkyl, aryl, alkylaryl, arylalkyl, arylheteroaryl, heteroaryl, heterocyclylamino, alkylheteroaryl, or heteroarylalkyl, and X$^1$ can be unsubstituted or optionally independently substituted with one or more of X$^2$ moieties which can be the same or different and are independently selected;

X$^2$ is hydroxy, alkyl, aryl, alkoxy, aryloxy, thio, alkylthio, arylthio, amino, alkylamino, arylamino, alkylsulfonyl, arylsulfonyl, alkylsulfonamido, arylsulfonamido, carboxy, carbalkoxy, carboxamido, alkoxycarbonylamino, alkoxycarbonyloxy, alkylureido, arylureido, halogen, cyano, keto, ester or nitro, wherein each of said alkyl, alkoxy, and aryl can be unsubstituted or optionally independently substituted with one or more moieties which can be the same or different and are independently selected from alkyl, alkenyl, alkynyl, cycloalkyl, cycloalkyl-alkyl, heterocyclyl, heterocyclylalkyl, aryl, alkylaryl, arylalkyl, arylheteroaryl, heteroaryl, heterocyclylamino, alkylheteroaryl and heteroarylalkyl;

W may be present or absent, and when W is present W is C(=O), C(=S), C(=NH), C(=N—OH), C(=N—CN), S(O) or S(O$_2$);

Q maybe present or absent, and when Q is present, Q is N(R), P(R), CR=CR', (CH$_2$)$_p$, (CHR)$_p$, (CRR')$_p$, (CHR—CHR')$_p$, O, S, S(O) or S(O$_2$);

when Q is absent, M is (i) either directly linked to A or (ii) M is an independent substituent on L and A is an independent substituent on E, with said independent substituent being selected from —OR, —CH(R$^{1'}$), S(O)$_{0-2}$R or —NRR'; when both Q and M are absent, A is either directly linked to L, or A is an independent substituent on E, selected from —OR, CH(R)(R$^{1'}$), —S(O)$_{0-2}$R or —NRR';

A is present or absent and if present A is —O—, —O(R)CH$_2$—, —(CHR)$_p$—, —(CHR—CHR')$_p$—, (CRR')$_p$, N(R), NRR', S, or S(O$_2$), and when Q is absent, A is —OR, —CH(R)(R$^{1'}$) or —NRR'; and when A is absent, either Q and E are connected by a bond or Q is an independent substituent on M;

E is present or absent and if present E is CH, N, C(R);

G may be present or absent, and when G is present, G is (CH$_2$)$_p$, (CHR)$_p$, or (CRR')$_p$; when G is absent, J is present and E is directly connected to the carbon atom marked position 1;

J may be present or absent, and when J is present, J is (CH$_2$)$_p$, (CHR—CHR')$_p$, (CHR)$_p$, (CRR')$_p$, S(O$_2$), N(H), N(R) or O; when J is absent and G is present, L is directly linked to the nitrogen atom marked position 2;

L may be present or absent, and when L is present, L is CH, N, or CR; when L is absent, M is present or absent; if M is present with L being absent, then M is directly and independently linked to E, and J is directly and independently linked to E;

M may be present or absent, and when M is present, M is O, N(R), S, S(O$_2$), (CH$_2$)$_p$, (CHR)$_p$, (CHR—CHR')$_p$, or (CRR')$_p$;

p is a number from 0 to 6;

R, R' and R$^3$ can be the same or different, each being independently selected from the group consisting of: H, C$_1$-C$_{10}$ alkyl, C$_2$-C$_{10}$ alkenyl, C$_3$-C$_8$ cycloalkyl, C$_3$-C$_8$ heterocyclyl, alkoxy, aryloxy, alkylthio, arylthio, amino, amido, arylthioamino, arylcarbonylamino, arylaminocarboxy, alkylaminocarboxy, heteroalkyl, heteroalkenyl, alkenyl, alkynyl, aryl-alkyl, heteroarylalkyl, ester, carboxylic acid, carbamate, urea, ketone, aldehyde, cyano, nitro, halogen, (cycloalkyl)alkyl, aryl, heteroaryl, alkyl-aryl, alkylheteroaryl, alkyl-heteroaryl and (heterocyclyl)alkyl;

R and R' in (CRR') can be linked together such that the combination forms a cycloalkyl or heterocyclyl moiety; and R' is carbonyl.

The compound of Structural Formula VII has the structure:

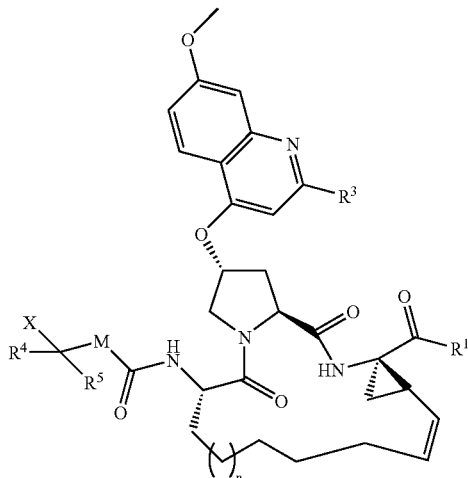

or a pharmaceutically acceptable salt, solvate, or ester thereof;
wherein in Formula VIII:
M is O, N(H), or $CH_2$;
n is 0-4;
$R^1$ is —$OR^6$, —$NR^6R^7$ or

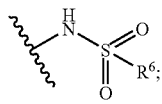

where $R^6$ and $R^7$ can be the same or different, each being independently selected from the group consisting of hydrogen, alkyl, alkenyl, alkynyl, heteroalkyl, cycloalkyl, cycloalkylalkyl, aryl, arylalkyl, heteroaryl, heteroarylalkyl, heterocyclyl, heterocyclylalkyl, hydroxyl, amino, arylamino and alkylamino;
$R^4$ and $R^5$ can be the same or different, each being independently selected from the group consisting of H, alkyl, aryl and cycloalkyl; or alternatively $R^4$ and $R^5$ together form part of a cyclic 5- to 7-membered ring such that the moiety

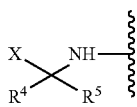

is represented by

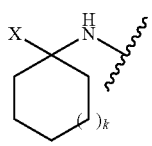

where k is 0 to 2;

X is selected from the group consisting of:

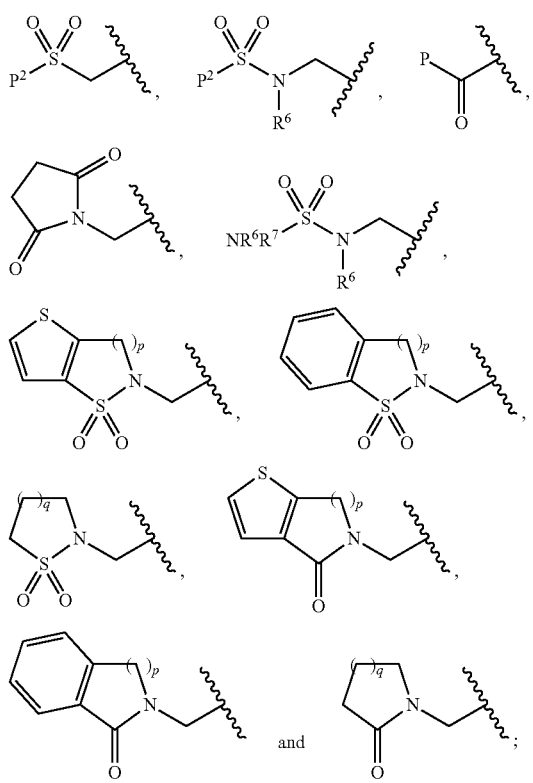

where p is 1 to 2, q is 1-3 and $P^2$ is alkyl, aryl, heteroaryl, heteroalkyl, cycloalkyl, dialkylamino, alkylamino, arylamino or cycloalkylamino; and $R^3$ is selected from the group consisting of: aryl, heterocyclyl, heteroaryl,

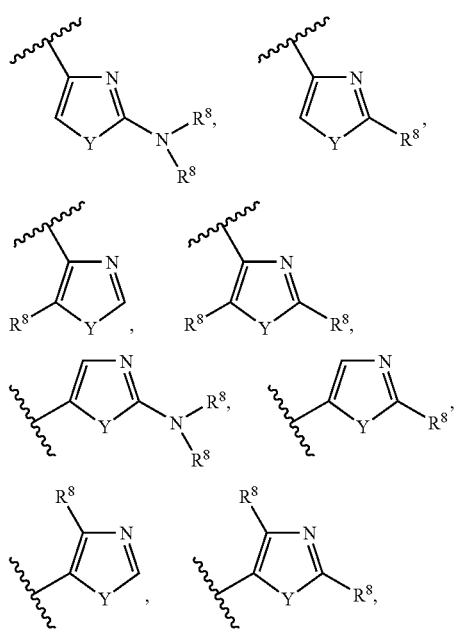

-continued

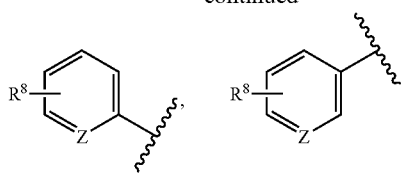 and 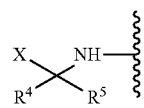

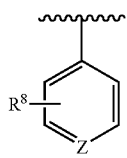

is represented by

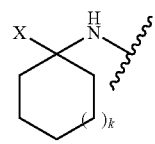

where k is 0 to 2;

where Y is O, S or NH, and Z is CH or N, and the $R^8$ moieties can be the same or different, each $R^8$ being independently selected from the group consisting of hydrogen, alkyl, heteroalkyl, cycloalkyl, aryl, heteroaryl, heterocyclyl, hydroxyl, amino, arylamino, alkylamino, dialkylamino, halo, alkylthio, arylthio and alkyloxy.

The compound of Structural Formula VIII has the structure:

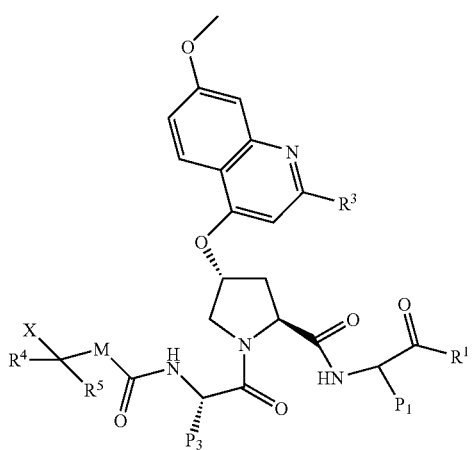

or a pharmaceutically acceptable salt, solvate, or ester thereof;

wherein in Formula VIII:

M is O, N(H), or $CH_2$;

$R^1$ is —C(O)$NHR^6$, where $R^6$ is hydrogen, alkyl, alkenyl, alkynyl, heteroalkyl, cycloalkyl, cycloalkylalkyl, aryl, arylalkyl, heteroaryl, heteroarylalkyl, heterocyclyl, heterocyclylalkyl, hydroxyl, amino, arylamino or alkylamino;

$P_1$ is selected from the group consisting of alkyl, alkenyl, alkynyl, cycloalkyl haloalkyl;

$P_3$ is selected from the group consisting of alkyl, cycloalkyl, aryl and cycloalkyl fused with aryl;

$R^4$ and $R^5$ can be the same or different, each being independently selected from the group consisting of H, alkyl, aryl and cycloalkyl; or alternatively $R^4$ and $R^5$ together form part of a cyclic 5- to 7-membered ring such that the moiety X is selected from the group consisting of:

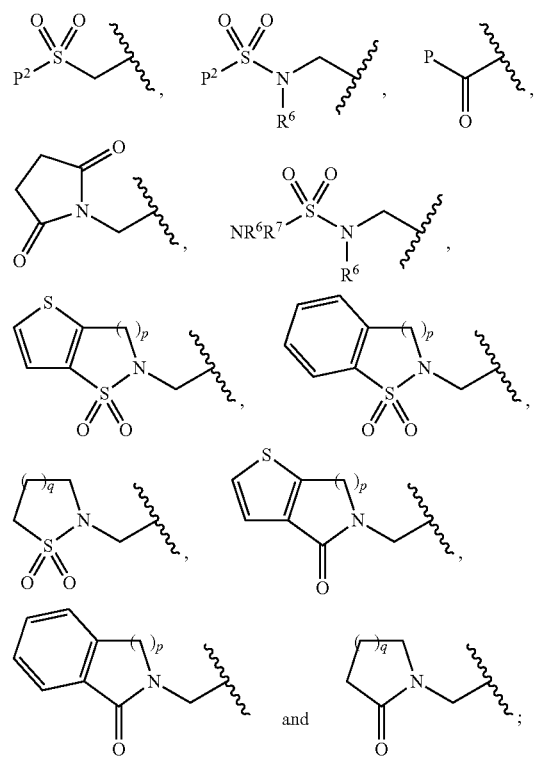

where p is 1 to 2, q is 1 to 3 and $P^2$ is alkyl, aryl, heteroaryl, heteroalkyl, cycloalkyl, dialkylamino, alkylamino, arylamino or cycloalkylamino; and $R^3$ is selected from the group consisting of: aryl, heterocyclyl, heteroaryl,

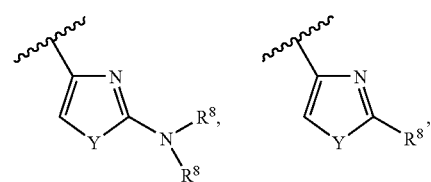

-continued

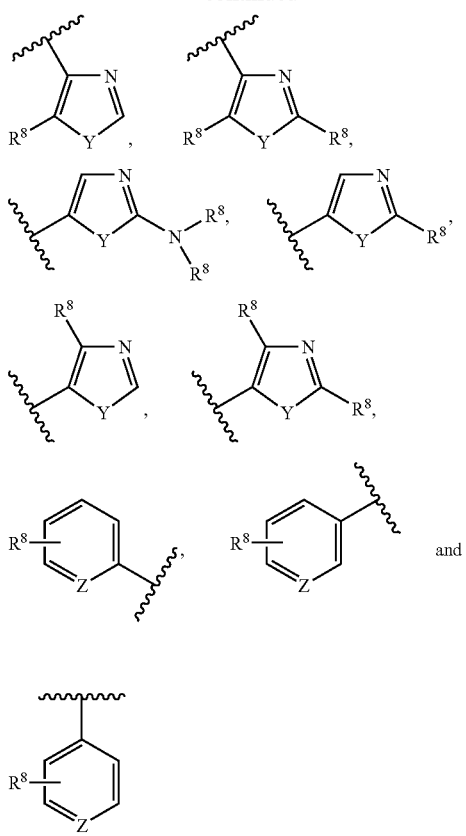

where Y is O, S or NH, and Z is CH or N, and the $R^8$ moieties can be the same or different, each $R^8$ being independently selected from the group consisting of hydrogen, alkyl, heteroalkyl, cycloalkyl, aryl, heteroaryl, heterocyclyl, hydroxyl, amino, arylamino, alkylamino, dialkylamino, halo, alkylthio, arylthio and alkyloxy.

The compound of Structural Formula IX has the structure:

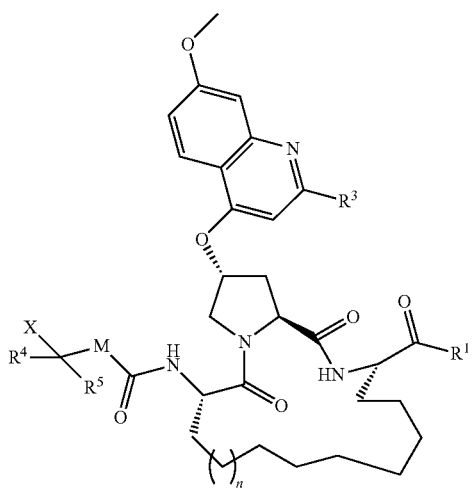

or a pharmaceutically acceptable salt, solvate, or ester thereof;

wherein in Formula IX:

M is O, N(H), or $CH_2$;

n is 0-4;

$R^1$ is $-OR^6$, $-NR^6R^7$ or

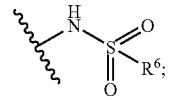

where $R^6$ and $R^7$ can be the same or different, each being independently selected from the group consisting of hydrogen, alkyl, alkenyl, alkynyl, heteroalkyl, cycloalkyl, cycloalkylalkyl, aryl, arylalkyl, heteroaryl, heteroarylalkyl, heterocyclyl, heterocyclylalkyl, hydroxyl, amino, arylamino and alkylamino;

$R^4$ and $R^5$ can be the same or different, each being independently selected from the group consisting of H, alkyl, aryl and cycloalkyl; or alternatively $R^4$ and $R^5$ together form part of a cyclic 5- to 7-membered ring such that the moiety

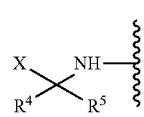

is represented by

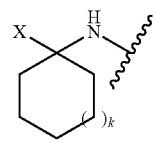

where k is 0 to 2;

X is selected from the group consisting of:

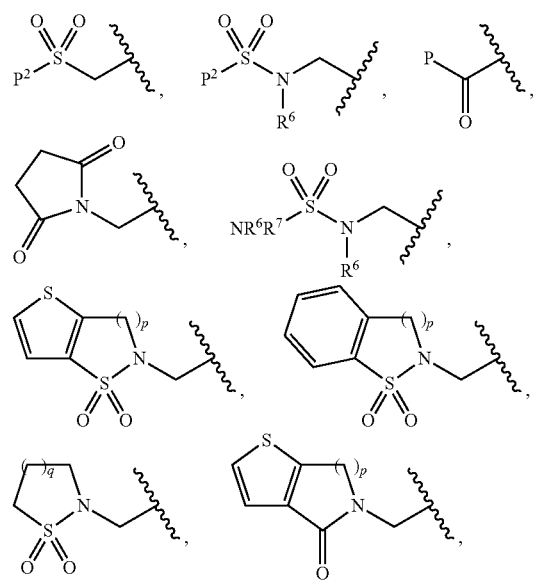

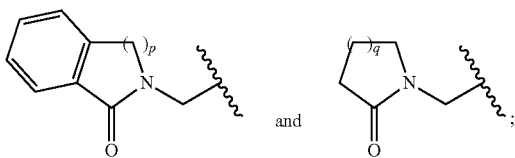

where p is 1 to 2, q is 1 to 3 and $P^2$ is alkyl, aryl, heteroaryl, heteroalkyl, cycloalkyl, dialkylamino, alkylamino, arylamino or cycloalkylamino; and $R^3$ is selected from the group consisting of: aryl, heterocyclyl, heteroaryl,

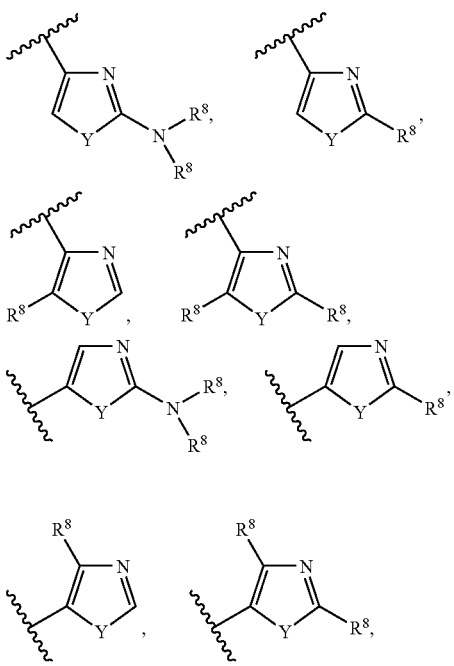

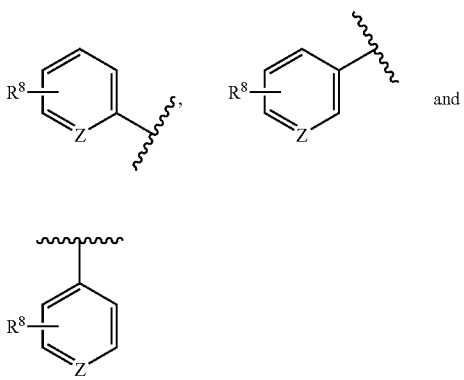

where Y is O, S or NH, and Z is CH or N, and the $R^8$ moieties can be the same or different, each $R^8$ being independently selected from the group consisting of hydrogen, alkyl, heteroalkyl, cycloalkyl, aryl, heteroaryl, heterocyclyl, hydroxyl, amino, arylamino, alkylamino, dialkylamino, halo, alkylthio, arylthio and alkyloxy.

The compound of Structural Formula X has the structure:

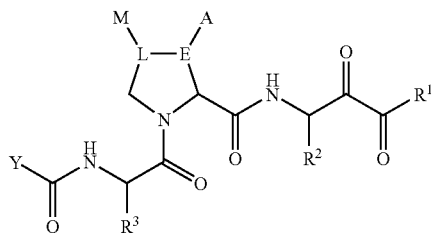

or a pharmaceutically acceptable salt, solvate, or ester thereof;
wherein in Formula X:

$R^1$ is $NHR^9$, wherein $R^9$ is H, alkyl-, alkenyl-, alkynyl-, aryl-, heteroalkyl-, heteroaryl-, cycloalkyl-, heterocyclyl-, arylalkyl-, or heteroarylalkyl;

A and M can be the same or different, each being independently selected from R, OR, NHR, NRR', SR, $SO_2R$, and halo; or A and M are connected to each other such that the moiety:

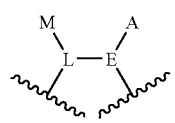

shown above in Formula I forms either a three, four, six, seven or eight-membered cycloalkyl, a four to eight-membered heterocyclyl, a six to ten-membered aryl, or a five to ten-membered heteroaryl;

E is C(H) or C(R);

L is C(H), C(R), $CH_2C(R)$, or $C(R)CH_2$;

R, R', $R^2$, and $R^3$ can be the same or different, each being independently selected from the group consisting of H, alkyl-, alkenyl-, alkynyl-, cycloalkyl-, heteroalkyl-, heterocyclyl-, aryl-, heteroaryl-, (cycloalkyl)alkyl-, (heterocyclyl)alkyl-, aryl-alkyl-, and heteroaryl-alkyl-; or alternately R and R' in NRR' are connected to each other such that NRR' forms a four to eight-membered heterocyclyl;

and Y is selected from the following moieties:

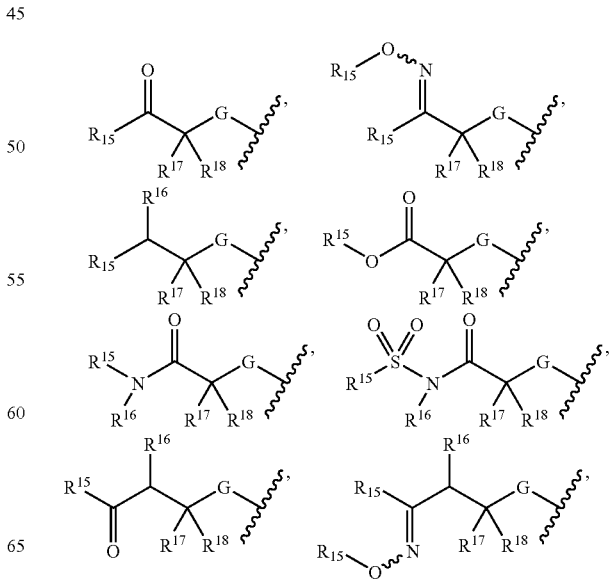

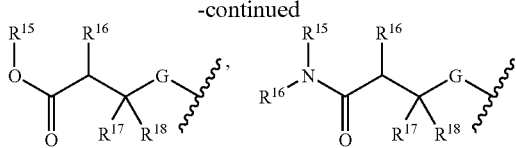

wherein G is NH or O; and $R^{15}$, $R^{16}$, $R^{17}$ and $R^{18}$ can be the same or different, each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl, or alternately, $R^{15}$ and $R^{16}$ are connected to each other to form a four to eight-membered cycloalkyl, heteroaryl or heterocyclyl structure, and likewise, independently $R^{17}$ and $R^{18}$ are connected to each other to form a three to eight-membered cycloalkyl or heterocyclyl;

wherein each of said alkyl, aryl, heteroaryl, cycloalkyl or heterocyclyl can be unsubstituted or optionally independently substituted with one or more moieties selected from the group consisting of: hydroxy, alkoxy, aryloxy, thio, alkylthio, arylthio, amino, amido, alkylamino, arylamino, alkylsulfonyl, arylsulfonyl, sulfonamido, alkyl, aryl, heteroaryl, alkylsulfonamido, arylsulfonamido, keto, carboxy, carbalkoxy, carboxamido, alkoxycarbonylamino, alkoxycarbonyloxy, alkylureido, arylureido, halo, cyano, and nitro.

In one embodiment, the "at least one compound" is a compound of structural Formula XI:

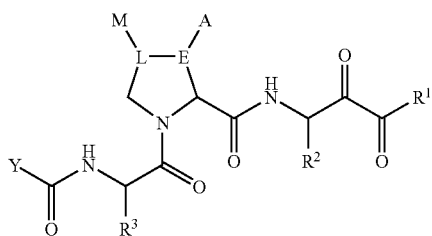

or a pharmaceutically acceptable salt, solvate, or ester thereof;

wherein in Formula XI:

$R^1$ is $NHR^9$, wherein $R^9$ is H, alkyl-, alkenyl-, alkynyl-, aryl-, heteroalkyl-, heteroaryl-, cycloalkyl-, heterocyclyl-, arylalkyl-, or heteroarylalkyl;

A and M can be the same or different, each being independently selected from R, $NR^9R^{10}$, SR, $SO_2R$, and halo; or A and M are connected to each other (in other words, A-E-L-M taken together) such that the moiety:

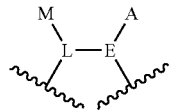

shown above in Formula I forms either a three, four, six, seven or eight-membered cycloalkyl, a four to eight-membered heterocyclyl, a six to ten-membered aryl, or a five to ten-membered heteroaryl;

E is C(H) or C(R);

L is C(H), C(R), $CH_2C(R)$, or $C(R)CH_2$;

R, R', $R^2$, and $R^3$ can be the same or different, each being independently selected from the group consisting of H, alkyl-, alkenyl-, alkynyl-, cycloalkyl-, heteroalkyl-, heterocyclyl-, aryl-, heteroaryl-, (cycloalkyl)alkyl-, (heterocyclyl)alkyl-, aryl-alkyl-, and heteroaryl-alkyl-; or alternately R and R' in NRR' are connected to each other such that $NR^9R^{10}$ forms a four to eight-membered heterocyclyl;

Y is selected from the following moieties:

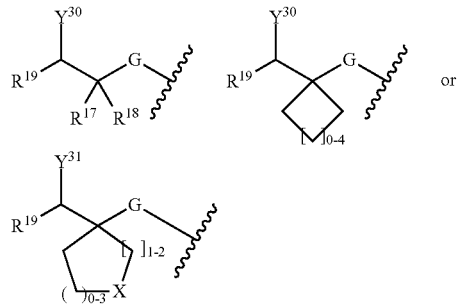

wherein $Y^{30}$ and $Y^{31}$ are selected from

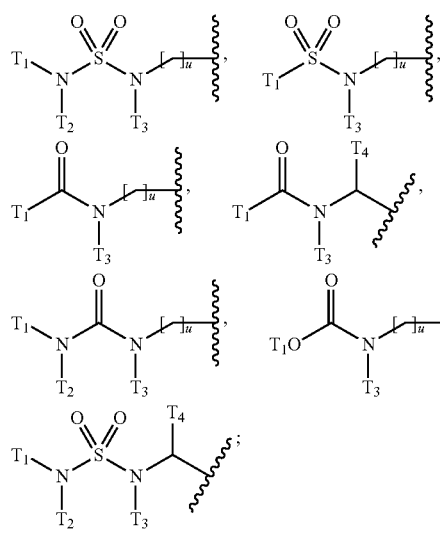

where $u$ is a number 0-6

X is selected from O, $NR^{15}$, $NC(O)R^{16}$, S, S(O) and $SO_2$;

G is NH or O; and $R^{15}$, $R^{16}$, $R^{17}$, $R^{18}$, $R^{19}$, $T_1$, $T_2$, $T_3$ and $T_4$ can be the same or different, each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl, or alternately, $R^{17}$ and $R^{18}$ are connected to each other to form a three to eight-membered cycloalkyl or heterocyclyl;

wherein each of said alkyl, aryl, heteroaryl, cycloalkyl or heterocyclyl can be unsubstituted or optionally independently substituted with one or more moieties selected from the group consisting of: hydroxy, alkoxy, aryloxy, thio, alkylthio, arylthio, amino, amido, alkylamino, arylamino, alkylsulfonyl, arylsulfonyl, sulfonamido, alkyl, aryl, heteroaryl, alkylsulfonamido, arylsulfonamido, keto, carboxy, carbalkoxy, carboxamido, alkoxycarbonylamino, alkoxycarbonyloxy, alkylureido, arylureido, halo, cyano, and nitro.

The compound of Structural Formula XII has the structure:

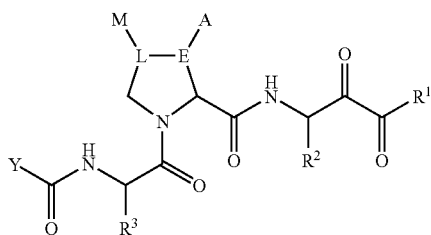

or a pharmaceutically acceptable salt, solvate, or ester thereof;
wherein in Formula XII:

$R^1$ is $NHR^9$, wherein $R^9$ is H, alkyl-, alkenyl-, alkynyl-, aryl-, heteroalkyl-, heteroaryl-, cycloalkyl-, heterocyclyl-, arylalkyl-, or heteroarylalkyl;

A and M can be the same or different, each being independently selected from R, OR, NHR, NRR', SR, $SO_2R$, and halo; or A and M are connected to each other such that the moiety:

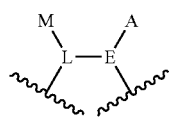

shown above in Formula I forms either a three, four, six, seven or eight-membered cycloalkyl, a four to eight-membered heterocyclyl, a six to ten-membered aryl, or a five to ten-membered heteroaryl;

E is C(H) or C(R);

L is C(H), C(R), $CH_2C(R)$, or $C(R)CH_2$;

R, R', $R^2$, and $R^3$ can be the same or different, each being independently selected from the group consisting of H, alkyl-, alkenyl-, alkynyl-, cycloalkyl-, heteroalkyl-, heterocyclyl-, aryl-, heteroaryl-, (cycloalkyl)alkyl-, (heterocyclyl)alkyl-, aryl-alkyl-, and heteroaryl-alkyl-; or alternately R and R' in NRR' are connected to each other such that NRR' forms a four to eight-membered heterocyclyl;

and Y is selected from the following moieties:

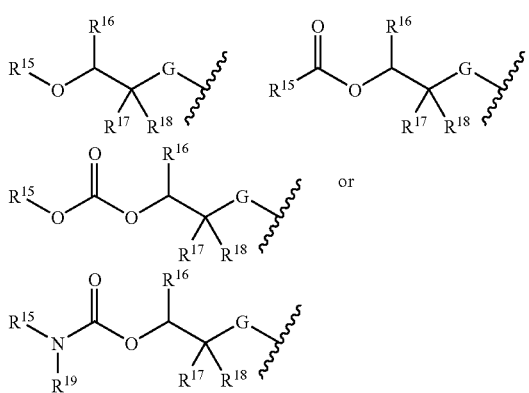

wherein G is NH or O; and $R^{15}$, $R^{16}$, $R^{17}$, $R^{18}$, and $R^{19}$ can be the same or different, each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl, or alternately, (i) either $R^{15}$ and $R^{16}$ are connected to each other to form a four to eight-membered cyclic structure, or $R^{15}$ and $R^{19}$ are connected to each other to form a four to eight-membered cyclic structure, and (ii) likewise, independently, $R^{17}$ and $R^{18}$ are connected to each other to form a three to eight-membered cycloalkyl or heterocyclyl;

wherein each of said alkyl, aryl, heteroaryl, cycloalkyl or heterocyclyl can be unsubstituted or optionally independently substituted with one or more moieties selected from the group consisting of: hydroxy, alkoxy, aryloxy, thio, alkylthio, arylthio, amino, amido, alkylamino, arylamino, alkylsulfonyl, arylsulfonyl, sulfonamido, alkylsulfonamido, arylsulfonamido, alkyl, aryl, heteroaryl, keto, carboxy, carbalkoxy, carboxamido, alkoxycarbonylamino, alkoxycarbonyloxy, alkylureido, arylureido, halo, cyano, and nitro.

The compound of Structural Formula XIII has the structure:

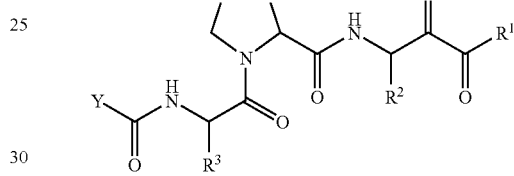

or a pharmaceutically acceptable salt, solvate, or ester thereof;
wherein in Formula XIII:

$R^1$ is $NHR^9$, wherein $R^9$ is H, alkyl-, alkenyl-, alkynyl-, aryl-, heteroalkyl-, heteroaryl-, cycloalkyl-, heterocyclyl-, arylalkyl-, or heteroarylalkyl;

A and M can be the same or different, each being independently selected from R, OR, NHR, NRR', SR, $SO_2R$, and halo; or A and M are connected to each other (in other words, A-E-L-M taken together) such that the moiety:

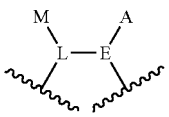

shown above in Formula I forms either a three, four, six, seven or eight-membered cycloalkyl, a four to eight-membered heterocyclyl, a six to ten-membered aryl, or a five to ten-membered heteroaryl;

E is C(H) or C(R);

L is C(H), C(R), $CH_2C(R)$, or $C(R)CH_2$;

R, R', $R^2$, and $R^3$ can be the same or different, each being independently selected from the group consisting of H, alkyl-, alkenyl-, alkynyl-, cycloalkyl-, heteroalkyl-, heterocyclyl-, aryl-, heteroaryl-, (cycloalkyl)alkyl-, (heterocyclyl)alkyl-, aryl-alkyl-, and heteroaryl-alkyl-; or alternately R and R' in NRR' are connected to each other such that NRR' forms a four to eight-membered heterocyclyl;

and Y is selected from the following moieties:

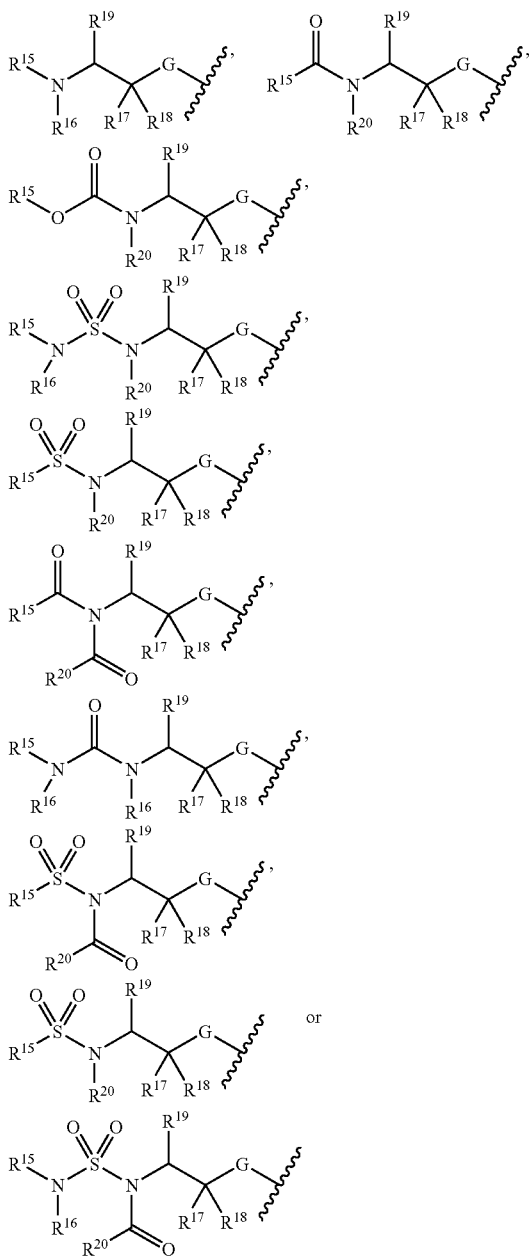

wherein G is NH or O, and $R^{15}$, $R^{16}$, $R^{17}$, $R^{18}$, $R^{19}$ and $R^{20}$ can be the same or different, each being independently selected from the group consisting of H, $C_1$-$C_{10}$ alkyl, $C_1$-$C_{10}$ heteroalkyl, $C_2$-$C_{10}$ alkenyl, $C_2$-$C_{10}$ heteroalkenyl, $C_2$-$C_{10}$ alkynyl, $C_2$-$C_{10}$ heteroalkynyl, $C_3$-$C_8$ cycloalkyl, $C_3$-$C_8$ heterocyclyl, aryl, heteroaryl, or alternately: (i) either $R^{15}$ and $R^{16}$ can be connected to each other to form a four to eight-membered cycloalkyl or heterocyclyl, or $R^{15}$ and $R^{19}$ are connected to each other to form a five to eight-membered cycloalkyl or heterocyclyl, or $R^{15}$ and $R^{20}$ are connected to each other to form a five to eight-membered cycloalkyl or heterocyclyl, and (ii) likewise, independently, $R^{17}$ and $R^{18}$ are connected to each other to form a three to eight-membered cycloalkyl or heterocyclyl, wherein each of said alkyl, aryl, heteroaryl, cycloalkyl or heterocyclyl can be unsubstituted or optionally independently substituted with one or more moieties selected from the group consisting of: hydroxy, alkoxy, aryloxy, thio, alkylthio, arylthio, amino, amido, alkylamino, arylamino, alkylsulfonyl, arylsulfonyl, sulfonamido, alkylsulfonamido, arylsulfonamido, keto, carboxy, carbalkoxy, carboxamido, alkoxycarbonylamino, alkoxycarbonyloxy, alkylureido, arylureido, halo, cyano, and nitro.

The compound of Structural Formula XIV has the structure:

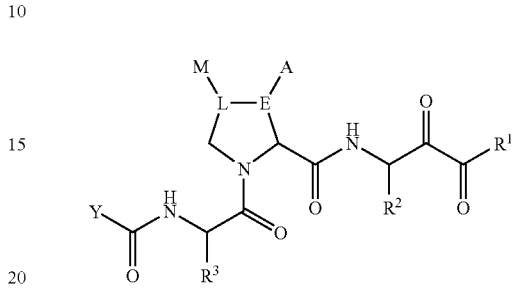

or a pharmaceutically acceptable salt, solvate, or ester thereof;

wherein in Formula XIV:

$R^1$ is $NHR^9$, wherein $R^9$ is H, alkyl-, alkenyl-, alkynyl-, aryl-, heteroalkyl-, heteroaryl-, cycloalkyl-, heterocyclyl-, arylalkyl-, or heteroarylalkyl;

A and M can be the same or different, each being independently selected from R, OR, NHR, NRR', SR, $SO_2R$, and halo;

or A and M are connected to each other such that the moiety:

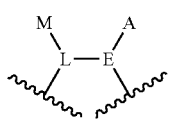

shown above in Formula I forms either a three, four, six, seven or eight-membered cycloalkyl, a four to eight-membered heterocyclyl, a six to ten-membered aryl, or a five to ten-membered heteroaryl;

E is C(H) or C=;

L is C(H), C=, $CH_2C$=, or C=$CH_2$;

R, R', $R^2$, and $R^3$ can be the same or different, each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl, or alternately R and R' in NRR' are connected to each other such that NRR' forms a four to eight-membered heterocyclyl;

and Y is selected from the following moieties:

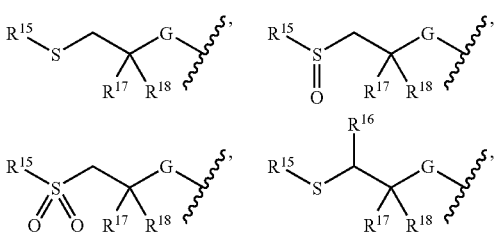

-continued

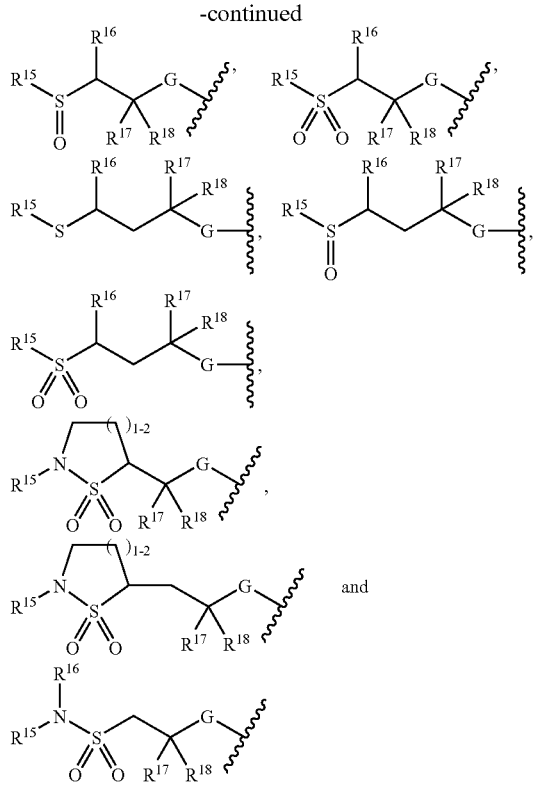

wherein G is NH or O; and $R^{15}$, $R^{16}$, $R^{17}$ and $R^{18}$ can be the same or different, each being independently selected from the group consisting of H, alkyl, heteroalkyl, alkenyl, heteroalkenyl, alkynyl, heteroalkynyl, cycloalkyl, heterocyclyl, aryl, and heteroaryl, or alternately, (i) $R^{15}$ and $R^{16}$ are connected to each other to form a four to eight-membered cyclic structure, and (ii) likewise, independently $R^{17}$ and $R^{18}$ are connected to each other to form a three to eight-membered cycloalkyl or heterocyclyl;

wherein each of said alkyl, aryl, heteroaryl, cycloalkyl or heterocyclyl can be unsubstituted or optionally independently substituted with one or more moieties selected from the group consisting of: hydroxy, alkoxy, aryloxy, thio, alkylthio, arylthio, amino, amido, alkylamino, arylamino, alkylsulfonyl, arylsulfonyl, sulfonamido, alkylsulfonamido, arylsulfonamido, alkyl, aryl, heteroaryl, keto, carboxy, carbalkoxy, carboxamido, alkoxycarbonylamino, alkoxycarbonyloxy, alkylureido, arylureido, halo, cyano, and nitro.

The compound of Structural Formula XV has the structure:

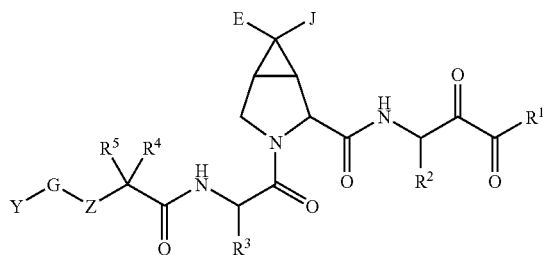

or a pharmaceutically acceptable salt, solvate, or ester thereof;

wherein in Formula XV:
$R^1$ is $NHR^9$, wherein $R^9$ is H, alkyl-, aryl-, heteroalkyl-, heteroaryl-, cycloalkyl-, cycloalkyl-, arylalkyl-, or heteroarylalkyl;

E and J can be the same or different, each being independently selected from the group consisting of R, OR, NHR, $NRR^7$, SR, halo, and $S(O_2)R$, or E and J can be directly connected to each other to form either a three to eight-membered cycloalkyl, or a three to eight-membered heterocyclyl moiety;

Z is N(H), N®, or O, with the proviso that when Z is O, G is present or absent and if G is present with Z being O, then G is C(=O);

G maybe present or absent, and if G is present, G is C(=O) or $S(O_2)$, and when G is absent, Z is directly connected to Y;

Y is selected from the group consisting of:

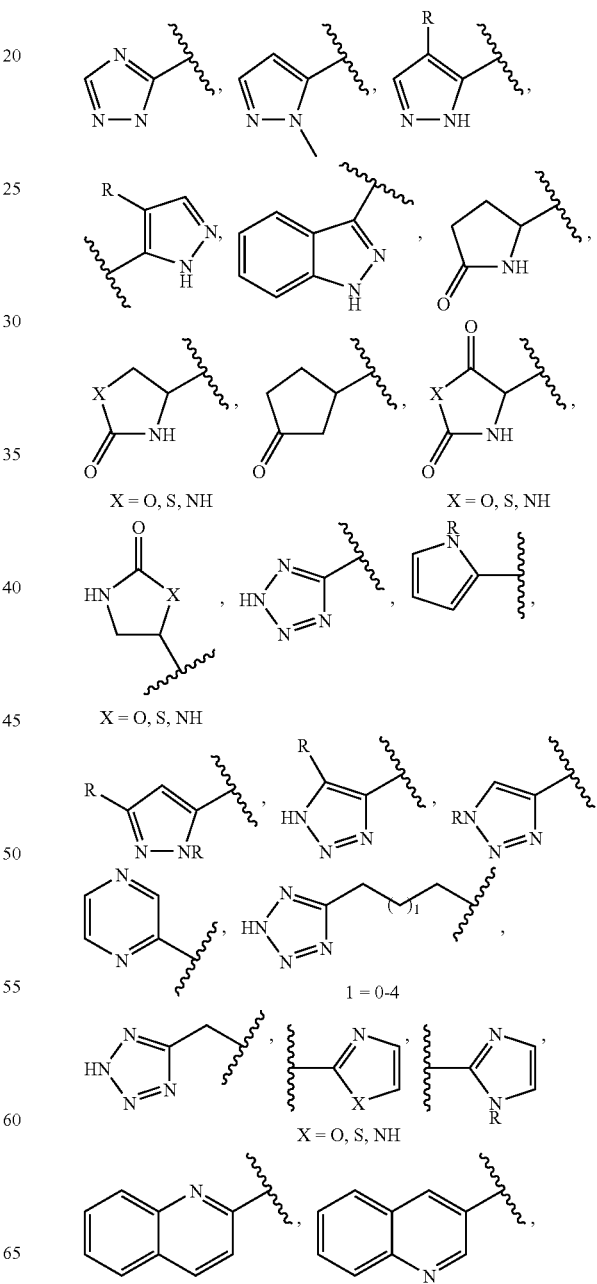

halo, hydroxy, thio, alkoxy, aryloxy, alkylthio, arylthio, amino, amido, ester, carboxylic acid, carbamate, urea, ketone, aldehyde, cyano, nitro, sulfonamido, sulfoxide, sulfone, sulfonyl urea, hydrazide, and hydroxamate.

The compound of Structural Formula XVI has the structure:

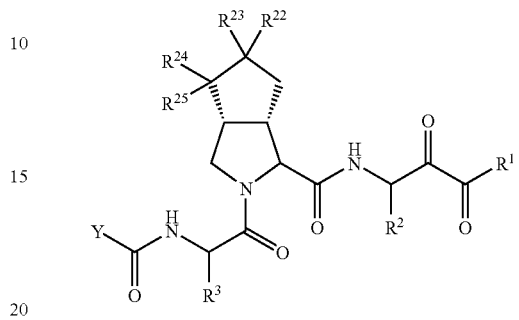

or a pharmaceutically acceptable salt, solvate, or ester thereof;

wherein in Formula XVI:

$R^1$ is $NHR^9$, wherein $R^9$ is H, alkyl-, alkenyl-, alkynyl-, aryl-, heteroalkyl-, heteroaryl-, cycloalkyl-, heterocyclyl-, arylalkyl-, or heteroarylalkyl;

$R^2$ and $R^3$ can be the same or different, each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl;

Y is selected from the following moieties:

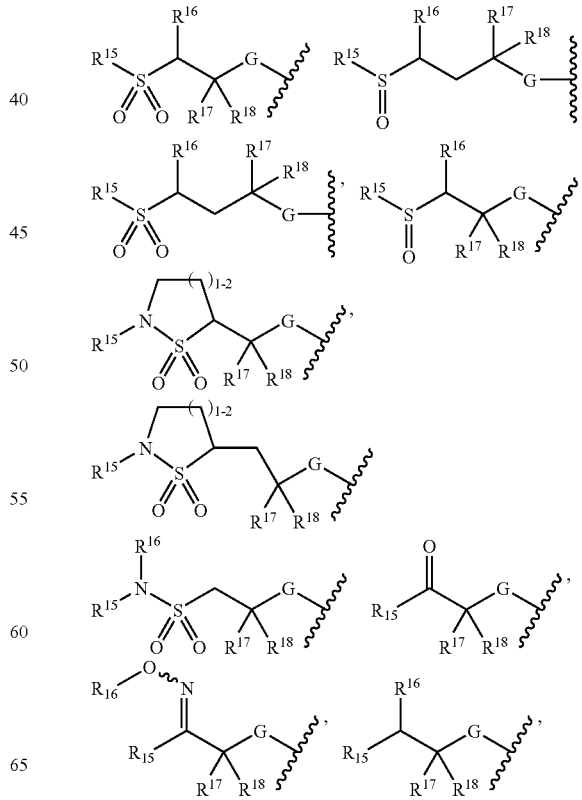

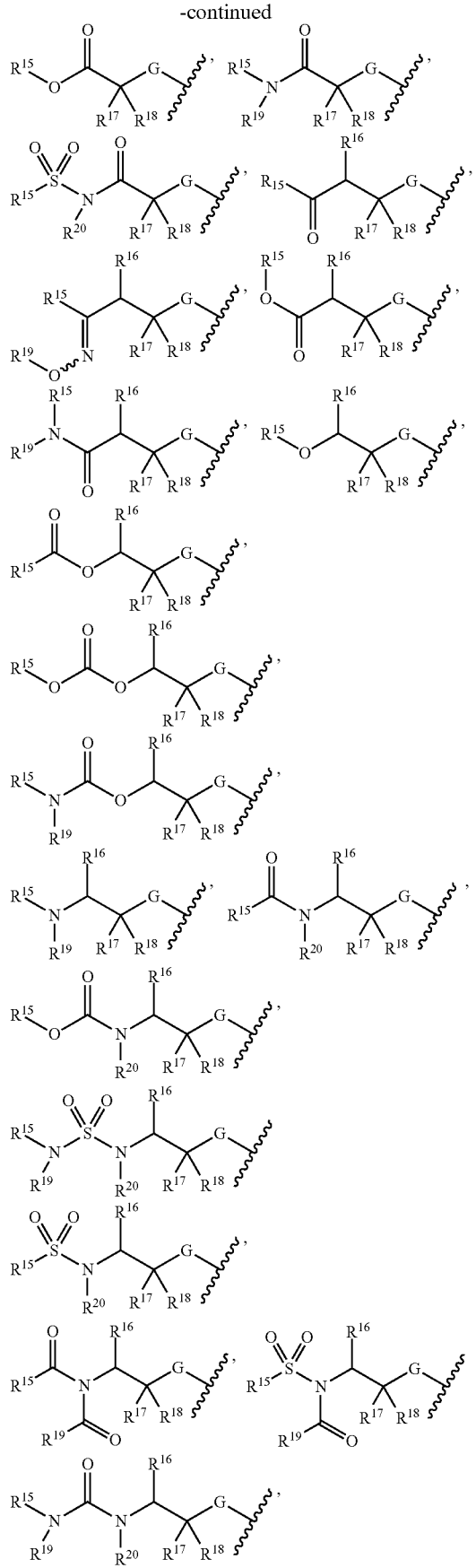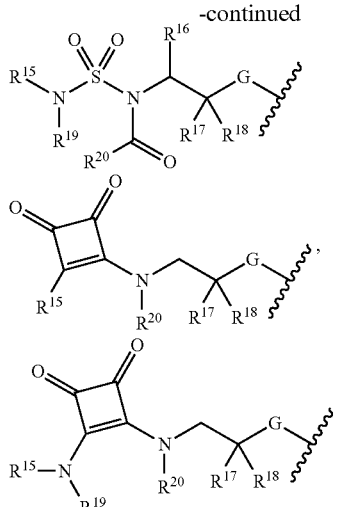

wherein G is NH or O; and $R^{15}$, $R^{16}$, $R^{17}$, $R^{18}$, $R^{19}$, $R^{20}$, $R^{21}$, $R^{22}$, $R^{23}$, $R^{24}$ and $R^{25}$ can be the same or different, each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl, or alternately (i) $R^{17}$ and $R^{18}$ are independently connected to each other to form a three to eight-membered cycloalkyl or heterocyclyl; (ii) likewise independently $R^{15}$ and $R^{19}$ are connected to each other to form a four to eight-membered heterocyclyl; (iii) likewise independently $R^{15}$ and $R^{16}$ are connected to each other to form a four to eight-membered heterocyclyl; (iv) likewise independently $R^{15}$ and $R^{20}$ are connected to each other to form a four to eight-membered heterocyclyl; (v) likewise independently $R^{22}$ and $R^{23}$ are connected to each other to form a three to eight-membered cycloalkyl or a four to eight-membered heterocyclyl; and (vi) likewise independently $R^{24}$ and $R^{25}$ are connected to each other to form a three to eight-membered cycloalkyl or a four to eight-membered heterocyclyl;

wherein each of said alkyl, aryl, heteroaryl, cycloalkyl or heterocyclyl can be unsubstituted or optionally independently substituted with one or more moieties selected from the group consisting of hydroxy, alkoxy, aryloxy, thio, alkylthio, arylthio, amino, amido, alkylamino, arylamino, alkylsulfonyl, arylsulfonyl, sulfonamido, alkyl, aryl, heteroaryl, alkylsulfonamido, arylsulfonamido, keto, carboxy, carbalkoxy, carboxamido, alkoxycarbonylamino, alkoxycarbonyloxy, alkylureido, arylureido, halo, cyano, and nitro.

The compound of Structural Formula XVII has the structure:

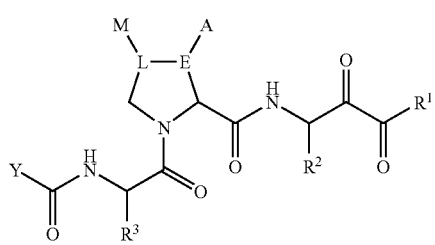

or a pharmaceutically acceptable salt, solvate, or ester thereof;

wherein in Formula XVII:

R$^1$ is NHR$^9$, wherein R$^9$ is H, alkyl-, alkenyl-, alkynyl-, aryl-, heteroalkyl-, heteroaryl-, cycloalkyl-, heterocyclyl-, arylalkyl-, or heteroarylalkyl;

A and M can be the same or different, each being independently selected from R, OR, NHR, NRR', SR, SO$_2$R, and halo; or A and M are connected to each other such that the moiety:

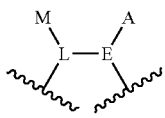

shown above in Formula I forms either a three, four, six, seven or eight-membered cycloalkyl, a four to eight-membered heterocyclyl, a six to ten-membered aryl, or a five to ten-membered heteroaryl;

E is C(H) or C=;

L is C(H), C=, CH$_2$C=, or C=CH$_2$;

R, R', R$^2$, and R$^3$ can be the same or different, each being independently selected from the group consisting of H, alkyl-, alkenyl-, alkynyl-, cycloalkyl-, heteroalkyl-, heterocyclyl-, aryl-, heteroaryl-, (cycloalkyl)alkyl-, (heterocyclyl)alkyl-, aryl-alkyl-, and heteroaryl-alkyl-; or alternately R and R' in NRR' are connected to each other such that NRR' forms a four to eight-membered heterocyclyl;

Y is selected from the following moieties:

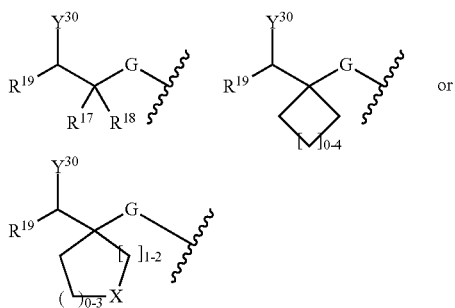

wherein Y$^{30}$ is selected from

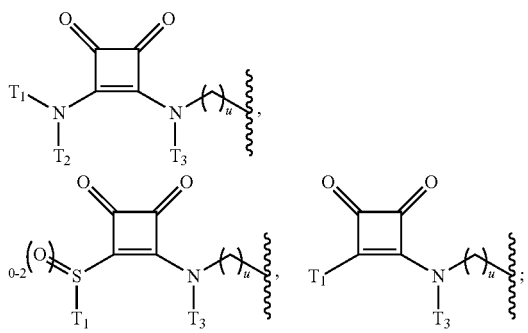

where $u$ is a number 0-1

X is selected from O, NR$^{15}$, NC(O)R$^6$, S, S(O) and SO$_2$;

G is NH or O; and

R$^{15}$, R$^{16}$, R$^{17}$, R$^{18}$, R$^{19}$, T$_1$, T$_2$, and T$_3$ can be the same or different, each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl, or alternately, R$^{17}$ and R$^{18}$ are connected to each other to form a three to eight-membered cycloalkyl or heterocyclyl;

wherein each of said alkyl, aryl, heteroaryl, cycloalkyl or heterocyclyl can be unsubstituted or optionally independently substituted with one or more moieties selected from the group consisting of: hydroxy, alkoxy, aryloxy, thio, alkylthio, arylthio, amino, amido, alkylamino, arylamino, alkylsulfonyl, arylsulfonyl, sulfonamido, alkyl, aryl, heteroaryl, alkylsulfonamido, arylsulfonamido, keto, carboxy, carbalkoxy, carboxamido, alkoxycarbonylamino, alkoxycarbonyloxy, alkylureido, arylureido, halo, cyano, and nitro.

The compound of Structural Formula XVIII has the structure:

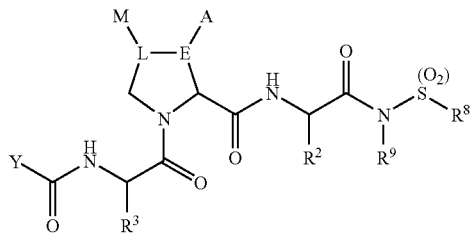

or a pharmaceutically acceptable salt, solvate, or ester thereof;

wherein in Formula XVIII:

R$^8$ is selected from the group consisting of alkyl-, aryl-, heteroalkyl-, heteroaryl-, cycloalkyl-, heterocyclyl-, arylalkyl-, heteroarylalkyl-, and heterocyclylalkyl;

R$^9$ is selected from the group consisting of H, alkyl, alkenyl, alkynyl, aryl and cycloalkyl;

A and M can be the same or different, each being independently selected from R, OR, N(H)R, N(RR'), SR, S(O$_2$)R, and halo; or A and M are connected to each other (in other words, A-E-L-M taken together) such that the moiety:

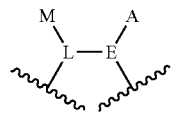

shown above in Formula I forms either a three, four, five, six, seven or eight-membered cycloalkyl, a four to eight-membered heterocyclyl, a six to ten-membered aryl, or a five to ten-membered heteroaryl;

E is C(H) or C(R);

L is C(H), C(R), CH$_2$C(R), or C(R)CH$_2$;

R and R' can be the same or different, each being independently selected from the group consisting of H, alkyl-, alkenyl-, alkynyl-, cycloalkyl-, heteroalkyl-, heterocyclyl-, aryl-, heteroaryl-, (cycloalkyl)alkyl-, (heterocyclyl)alkyl-, aryl-alkyl-, and heteroaryl-alkyl-; or alternately R and R' in N(RR') are connected to each other such that N(RR') forms a four to eight-membered heterocyclyl;

R$^2$ and R$^3$ can be the same or different, each being independently selected from the group consisting of H, alkyl, heteroalkyl, alkenyl, heteroalkenyl, alkynyl, heteroalkynyl, cycloalkyl, spiro-linked cycloalkyl, heterocyclyl, aryl, arylalkyl, heteroaryl, and heteroarylalkyl;

Y is selected from the following moieties:

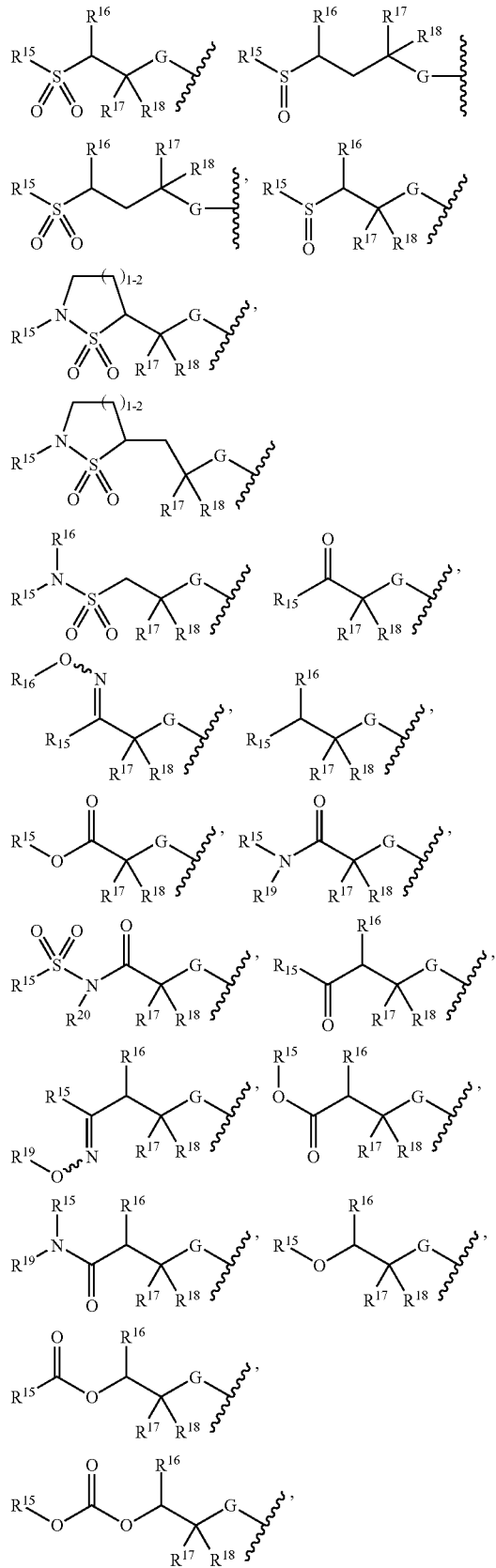

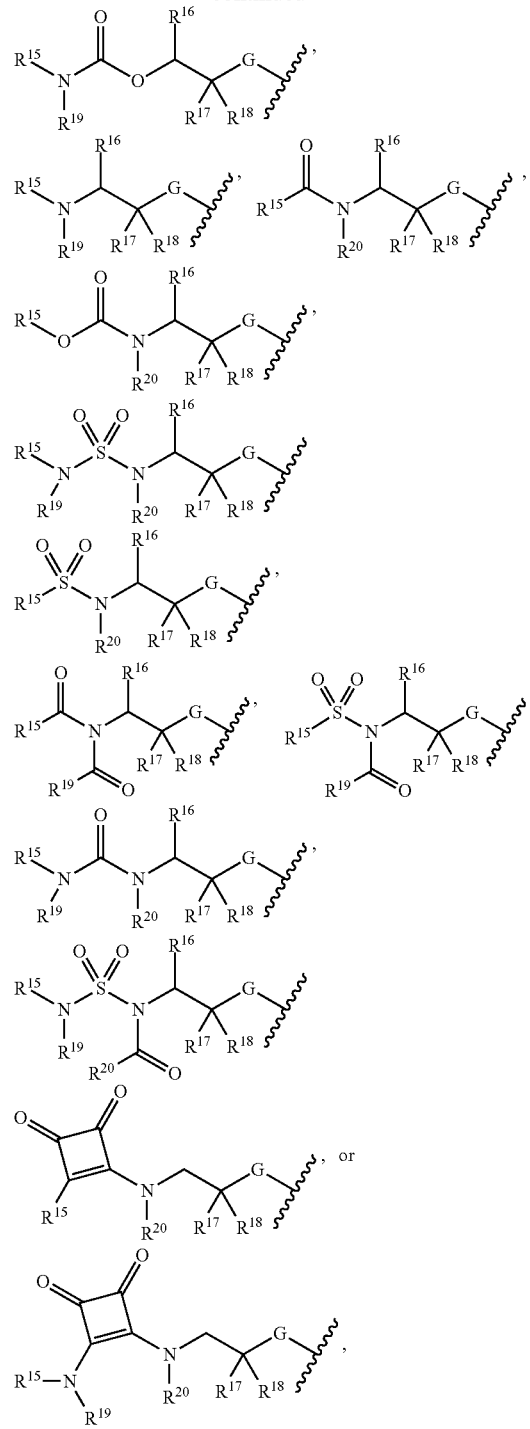

wherein G is NH or O; and $R^{15}$, $R^{16}$, $R^{17}$, $R^{18}$, $R^{19}$ and $R^{20}$ can be the same or different, each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl, or alternately (i) $R^{17}$ and $R^{18}$ are independently connected to each other to form a three to eight-membered cycloalkyl or heterocyclyl; (ii) likewise independently $R^{15}$ and $R^{19}$ are connected to each other to form a four to eight-membered heterocyclyl; (iii) likewise independently $R^{15}$ and $R^{16}$ are connected to each other to form a four to eight-membered heterocyclyl; and (iv) likewise independently $R^{15}$ and $R^{20}$ are connected to each other to form a four to eight-membered heterocyclyl;

wherein each of said alkyl, aryl, heteroaryl, cycloalkyl, spirolinked cycloalkyl, and heterocyclyl can be unsubstituted or optionally independently substituted with one or more moieties selected from the group consisting of hydroxy, alkoxy, aryloxy, thio, alkylthio, arylthio, amino, amido, alkylamino, arylamino, alkylsulfonyl, arylsulfonyl, sulfonamido, alkyl, alkenyl, aryl, heteroaryl, alkylsulfonamido, arylsulfonamido, keto, carboxy, carbalkoxy, carboxamido, alkoxycarbonylamino, alkoxycarbonyloxy, alkylureido, arylureido, halo, cyano, and nitro.

The compound of Structural Formula XIX has the structure:

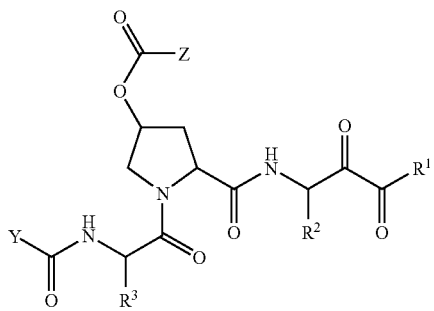

or a pharmaceutically acceptable salt, solvate, or ester thereof;

wherein in Formula XIX:

Z is selected from the group consisting of a heterocyclyl moiety, —N(H)(alkyl), —N(alkyl)$_2$, —N(H)(cycloalkyl), —N(cycloalkyl)$_2$, —N(H)(aryl, —N(aryl)$_2$, —N(H)(heterocyclyl), —N(heterocyclyl)$_2$, —N(H)(heteroaryl), and —N(heteroaryl)$_2$;

$R^1$ is NHR$^9$, wherein R$^9$ is H, alkyl-, alkenyl-, alkynyl-, aryl-, heteroalkyl-, heteroaryl-, cycloalkyl-, heterocyclyl-, arylalkyl-, or heteroarylalkyl;

$R^2$ and $R^3$ can be the same or different, each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl;

Y is selected from the following moieties:

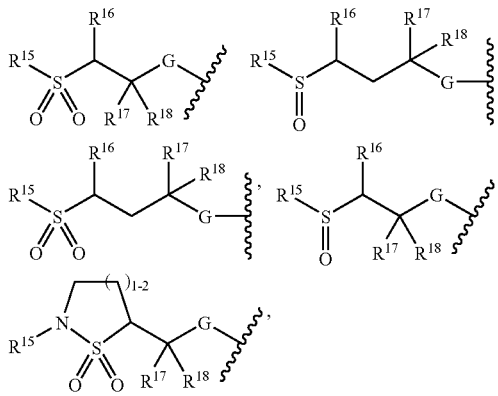

-continued

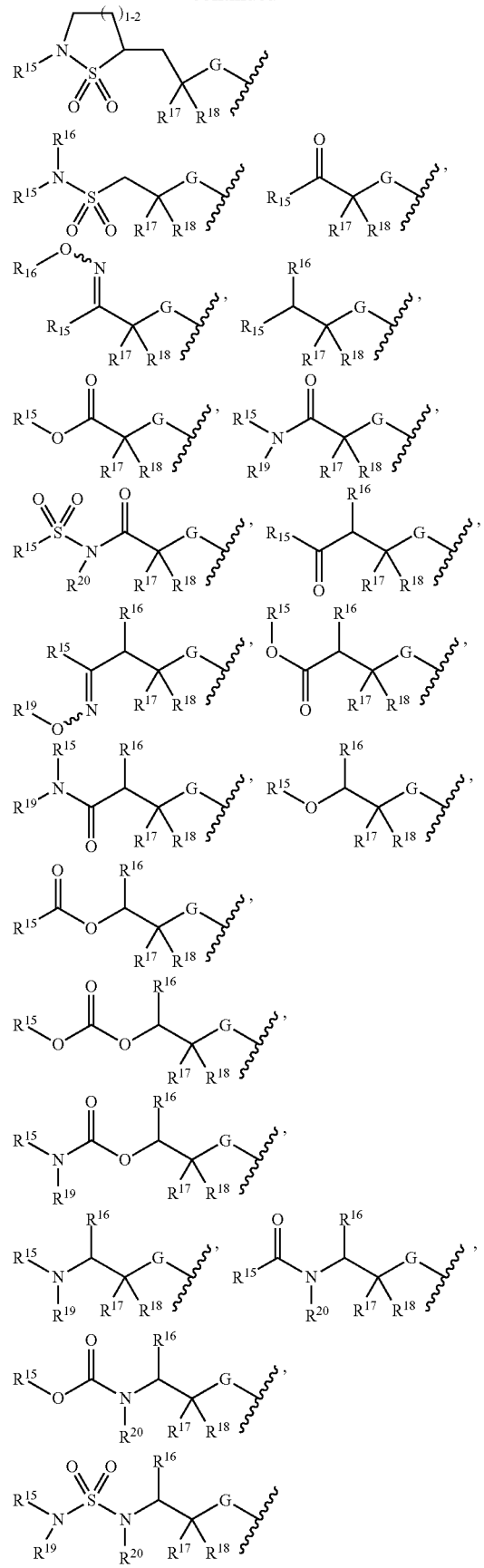

-continued

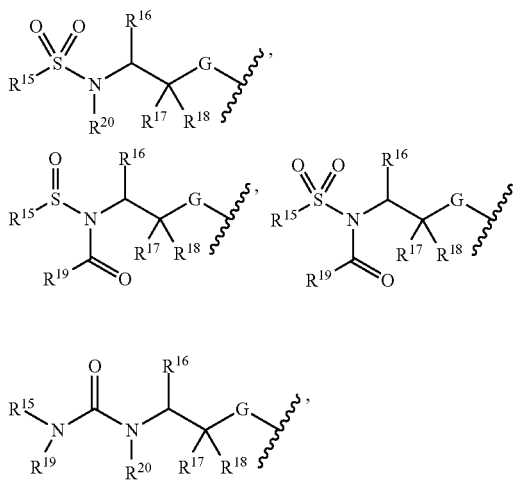

wherein G is NH or O; and $R^{15}$, $R^{16}$, $R^{17}$, $R^{18}$, $R^{19}$, $R^{20}$ and $R^{21}$ can be the same or different, each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl, or alternately (i) $R^{17}$ and $R^{18}$ are independently connected to each other to form a three to eight-membered cycloalkyl or heterocyclyl; (ii) likewise independently $R^{15}$ and $R^{19}$ are connected to each other to form a four to eight-membered heterocyclyl; (iii) likewise independently $R^{15}$ and $R^{16}$ are connected to each other to form a four to eight-membered heterocyclyl; and (iv) likewise independently $R^{15}$ and $R^{20}$ are connected to each other to form a four to eight-membered heterocyclyl;

wherein each of said alkyl, aryl, heteroaryl, cycloalkyl or heterocyclyl can be unsubstituted or optionally independently substituted with one or more moieties selected from the group consisting of hydroxy, alkoxy, aryloxy, thio, alkylthio, arylthio, amino, amido, alkylamino, arylamino, alkylsulfonyl, arylsulfonyl, sulfonamido, alkyl, aryl, heteroaryl, alkylsulfonamido, arylsulfonamido, keto, carboxy, carbalkoxy, carboxamido, alkoxycarbonylamino, alkoxycarbonyloxy, alkylureido, arylureido, halo, cyano, and nitro.

The compound of Structural Formula XX has the structure:

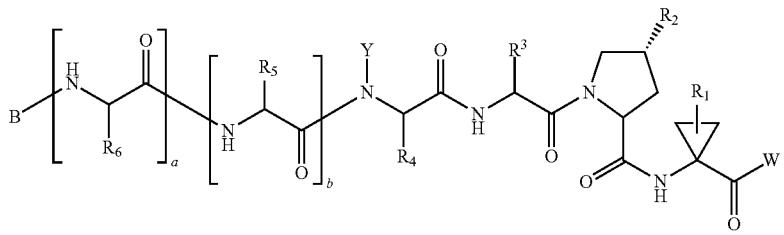

-continued

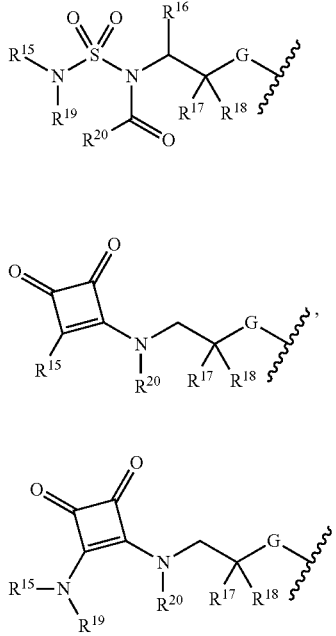

or a pharmaceutically acceptable salt, solvate, or ester thereof;

wherein in Formula XX:

a is 0 or 1; b is 0 or 1; Y is H or $C_{1-6}$alkyl;

B is H, an acyl derivative of formula $R_7$—C(O)— or a sulfonyl of formula $R_7$—SO2 wherein R7 is (i) $C_{1-10}$ alkyl optionally substituted with carboxyl, $C_{1-6}$ alkanoyloxy or $C_{1-6}$ alkoxy;
  (ii) $C_{3-7}$ cycloalkyl optionally substituted with carboxyl, ($C_{1-6}$ alkoxy)carbonyl or phenylmethoxycarbonyl;
  (iii) $C_6$ or $C_{10}$ aryl or $C_{7-16}$ aralkyl optionally substituted with $C_{1-6}$ alkyl, hydroxy, or amino optionally substituted with $C_{1-6}$ alkyl; or
  (iv) Het optionally substituted with $C_{1-6}$ alkyl, hydroxy, amino optionally substituted with $C_{1-6}$ alkyl, or amido optionally substituted with $C_{1-6}$ alkyl;

$R_6$, when present, is $C_{1-6}$ alkyl substituted with carboxyl;

$R_5$, when present, is $C_{1-6}$ alkyl optionally substituted with carboxyl;

$R_4$ is $C_{1-10}$alkyl, $C_{3-7}$ cycloalkyl or $C_{4-10}$ (alkylcycloalkyl);

$R_3$ is $C_{1-10}$ alkyl, $C_{3-7}$ cycloalkyl or $C_{4-10}$ (alkylcycloalkyl);

$R_2$ is $CH_2$—$R_{20}$, NH—$R_{20}$, 0-$R_{20}$ or S—$R_{20}$, wherein $R_{20}$ is a saturated or unsaturated $C_{3-7}$ cycloalkyl or $C_{4-10}$ (alkyl cycloalkyl) being optionally mono-, di- or tri-substituted with $R_{21}$, or $R_{20}$ is a $C_6$ or $C_{10}$ aryl or $C_{7-16}$ aralkyl optionally mono-, di- or tri-substituted with $R_{21}$, or $R_{20}$ is Het or (lower alkyl)-Het optionally mono-, di- or tri-substituted with $R_{21}$, wherein each $R_{21}$ is independently $C_{1-6}$ alkyl; $C_{1-6}$alkoxy; amino optionally mono- or di-substituted with $C_{1-6}$ alkyl; sulfonyl; $NO_2$; OH; SH; halo; haloalkyl; amido optionally mono-substituted with $C_{1-6}$ alkyl, $C_6$ or $C_{10}$ aryl, $C_{7-16}$ aralkyl, Het or (lower alkyl)-Het; carboxyl; carboxy(lower alkyl); $C_6$ or $C_{10}$ aryl, $C_{7-16}$ aralkyl or Het, said aryl, aralkyl or Het being optionally substituted with $R_{22}$;

wherein $R_{22}$ is $C_{1-6}$alkyl; $C_{1-6}$ alkoxy; amino optionally mono- or di-substituted with $C_{1-6}$ alkyl; sulfonyl; $NO_2$; OH; SH; halo; haloalkyl; carboxyl; amide or (lower alkyl) amide;

$R_1$ is $C_{1-6}$ alkyl or $C_{2-6}$ alkenyl optionally substituted with halogen; and W is hydroxy or a N-substituted amino.

In the above-shown structure of the compound of Formula XX, the terms P6, P5, P4, P3, P2 and P1 denote the respective amino acid moieties as is conventionally known to those skilled in the art.

The compound of Structural Formula XXI has the structure:

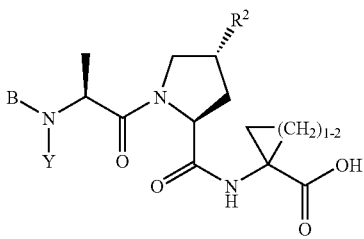

or a pharmaceutically acceptable salt, solvate, or ester thereof;

wherein in Formula XXI:

B is H, a $C_6$ or $C_{10}$ aryl, $C_{7-16}$ aralkyl; Het or (lower alkyl)-Het, all of which optionally substituted with $C_{1-6}$ alkyl; $C_{1-6}$ alkoxy; $C_{1-6}$ alkanoyl; hydroxy; hydroxyalkyl; halo; haloalkyl; nitro; cyano; cyanoalkyl; amino optionally substituted with $C_{1-6}$ alkyl; amido; or (lower alkyl)amide;

or B is an acyl derivative of formula $R_4$—C(O)—; a carboxyl of formula $R_4$—O—C(O)—; an amide of formula $R_4$—N($R_5$)—C(O)—; a thioamide of formula $R_4$—N($R_5$)—C(S)—; or a sulfonyl of formula $R_4$—SO2 wherein $R_4$ is (i) $C_{1-10}$ alkyl optionally substituted with carboxyl, $C_{1-6}$ alkanoyl, hydroxy, $C_{1-6}$ alkoxy, amino optionally mono- or di-substituted with $C_{1-6}$ alkyl, amido, or (lower alkyl) amide;

(ii) $C_{3-7}$ cycloalkyl, $C_{3-7}$ cycloalkoxy, or $C_{4-10}$ alkylcycloalkyl, all optionally substituted with hydroxy, carboxyl, ($C_{1-6}$ alkoxy)carbonyl, amino optionally mono- or di-substituted with $C_{1-6}$ alkyl, amido, or (lower alkyl) amide;

(iii) amino optionally mono- or di-substituted with $C_{1-6}$ alkyl; amido; or (lower alkyl)amide;

(iv) $C_6$ or $C_{10}$ aryl or $C_{7-16}$ aralkyl, all optionally substituted with $C_{1-6}$ alkyl, hydroxy, amido, (lower alkyl)amide, or amino optionally mono- or di-substituted with $C_{1-6}$ alkyl; or (v) Het or (lower alkyl)-Het, both optionally substituted with $C_{1-6}$ alkyl, hydroxy, amido, (lower alkyl) amide, or amino optionally mono- or di-substituted with $C_{1-6}$ alkyl;

$R_5$ is H or $C_{1-6}$ alkyl;

with the proviso that when $R_4$ is an amide or a thioamide, $R_4$ is not (ii) a cycloalkoxy;

Y is H or $C_{1-6}$alkyl;

$R_3$ is $C_{1-8}$ alkyl, $C_{3-7}$ cycloalkyl, or $C_{4-10}$ alkylcycloalkyl, all optionally substituted with hydroxy, $C_{1-6}$ alkoxy, $C_{1-6}$ thioalkyl, amido, (lower alkyl)amide, $C_6$ or $C_{10}$ aryl, or $C_{7-16}$ aralkyl;

$R_2$ is $CH_2$—$R_{20}$, NH—$R_{20}$, O—$R_{20}$ or S—$R_{20}$, wherein $R_{20}$ is a saturated or unsaturated $C_{3-7}$ cycloalkyl or $C_{4-10}$ (alkylcycloalkyl), all of which being optionally mono-, di- or tri-substituted with $R_{21}$, or $R_{20}$ is a $C_6$ or $C_{10}$ aryl or $C_{7-14}$ aralkyl, all optionally mono-, di- or tri-substituted with $R_{21}$, or $R_{20}$ is Het or (lower alkyl)-Het, both optionally mono-, di- or tri-substituted with $R_{21}$, wherein each $R_{21}$ is independently $C_{1-6}$ alkyl; $C_{1-6}$ alkoxy; lower thioalkyl; sulfonyl; $NO_2$; OH; SH; halo; haloalkyl; amino optionally mono- or di-substituted with $C_{1-6}$ alkyl, $C_6$ or $C_{10}$ aryl, $C_{7-14}$ aralkyl, Het or (lower alkyl)-Het; amido optionally mono-substituted with $C_{1-6}$ alkyl, $C_6$ or $C_{10}$ aryl, $C_{7-14}$ aralkyl, Het or (lower alkyl)-Het; carboxyl; carboxy (lower alkyl); $C_6$ or $C_{10}$ aryl, $C_{7-14}$ aralkyl or Het, said aryl, aralkyl or Het being optionally substituted with $R_{22}$;

wherein $R_{22}$ is $C_{1-6}$ alkyl; $C_{3-7}$ cycloalkyl; $C_{1-6}$ alkoxy; amino optionally mono- or di-substituted with $C_{1-6}$ alkyl; sulfonyl; (lower alkyl)sulfonyl; $NO_2$; OH; SH; halo; haloalkyl; carboxyl; amide; (lower alkyl)amide; or Het optionally substituted with $C_{1-6}$ alkyl;

R1 is H; $C_{1-6}$ alkyl, $C_{3-7}$ cycloalkyl, $C_{2-6}$ alkenyl, or $C_{2-6}$ alkynyl, all optionally substituted with halogen.

The compound of Structural Formula XXII has the structure:

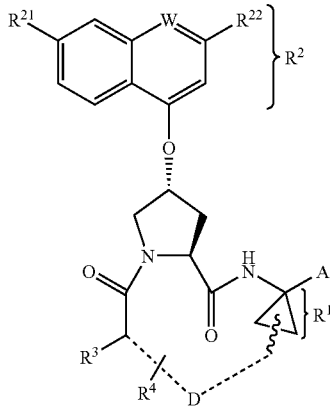

or a pharmaceutically acceptable salt, solvate, or ester thereof;

wherein in Formula XXII:

W is CH or N, $R^{21}$ is H, halo, $C_{1-6}$ alkyl, $C_{3-6}$ cycloalkyl, $C_{1-6}$ haloalkyl, $C_{1-6}$ alkoxy, $C_{3-6}$ cycloalkoxy, hydroxy, or $N(R^{23})_2$, wherein each $R^{23}$ is independently H, $C_{1-6}$ alkyl or $C_{3-6}$ cycloalkyl;

$R^{22}$ is H, halo, $C_{1-6}$ alkyl, $C_{3-6}$ cycloalkyl, $C_{1-6}$ haloalkyl, $C_{1-6}$ thioalkyl, $C_{1-6}$ alkoxy, $C_{3-6}$ cycloalkoxy, $C_{2-7}$ alkoxyalkyl, $C_{3-6}$ cycloalkyl, $C_6$ or $_{10}$ aryl or Het, wherein Het is a five-, six-, or seven-membered saturated or unsaturated heterocycle containing from one to four heteroatoms selected from nitrogen, oxygen and sulfur;

said cycloalkyl, aryl or Het being substituted with $R^{24}$, wherein $R^{24}$ is H, halo, $C_{1-6}$ alkyl, $C_{3-6}$ cycloalkyl, $C_{1-6}$ alkoxy, $C_{3-6}$ cycloalkoxy, $NO_2$, $N(R^{25})_2$, NH—C(O)—$R^{25}$ or NH—C(O)—NH—$R^{25}$, wherein each $R^{25}$ is independently: H, $C_{1-6}$ alkyl or $C_{3-6}$ cycloalkyl;

or $R^{24}$ is NH—C(O)—$OR^{26}$ wherein $R^{26}$ is $C_{1-6}$ alkyl or $C_{3-6}$ cycloalkyl;

$R^3$ is hydroxy, $NH_2$, or a group of formula —NH—$R^{31}$, wherein $R^{31}$ is $C_6$ or $_{10}$ aryl, heteroaryl, —C(O)—$R^{32}$, —C(O)—$NHR^{32}$ or —C(O)—$OR^{32}$, wherein $R^{32}$ is $C_{1-6}$ alkyl or $C_{3-6}$ cycloalkyl;

D is a 5 to 10-atom saturated or unsaturated alkylene chain optionally containing one to three heteroatoms independently selected from: O, S, or N—$R^{41}$, wherein $R^{41}$ is H, $C_{1-6}$ alkyl, $C_{3-6}$ cycloalkyl or —C(O)—$R^{42}$, wherein $R^{42}$ is $C_{1-6}$ alkyl, $C_{3-6}$ cycloalkyl or $C_6$ or $_{10}$ aryl; $R^4$ is H or from one to three substituents at any carbon atom of said chain D, said substituent independently selected from the group consisting of: $C_{1-6}$ alkyl, $C_{1-6}$ haloalkyl, $C_{1-6}$ alkoxy, hydroxy, halo, amino, oxo, thio and $C_{1-6}$ thioalkyl, and A is an amide of formula —C(O)—NH—$R^5$, wherein $R^5$ is selected from the group consisting of: $C_{1-8}$ alkyl, $C_{3-6}$ cycloalkyl, $C_6$ or $_{10}$ aryl and $C_{7-16}$ aralkyl; or A is a carboxylic acid.

The compound of Structural Formula XXIII has the structure:

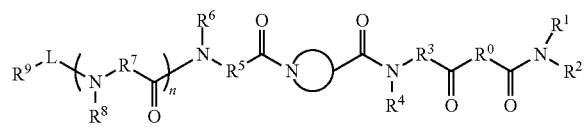

or a pharmaceutically acceptable salt, solvate, or ester thereof;

wherein in Formula XXIII:

$R^0$ is a bond or difluoromethylene;

$R^1$ is hydrogen;

$R^2$ and $R^9$ are each independently optionally substituted aliphatic group, optionally substituted cyclic group or optionally substituted aromatic group; R3, R5 and R7 are each independently:

optionally substituted (1,1- or 1,2-)cycloalkylene; or optionally substituted (1,1- or 1,2-) heterocyclylene; or methylene or ethylene), substituted with one substituent selected from the group consisting of an optionally substituted aliphatic group, an optionally substituted cyclic group or an optionally substituted aromatic group, and wherein the methylene or ethylene is further optionally substituted with an aliphatic group substituent; or;

R4, R6, R8 and $R^{10}$ are each independently hydrogen or optionally substituted aliphatic group;

is substituted monocyclic azaheterocyclyl or optionally substituted multicyclic azaheterocyclyl, or optionally substituted multicyclic azaheterocyclenyl wherein the unsaturatation is in the ring distal to the ring bearing the $R^9$-L-(N($R^8$)—$R^7$—C(O)—$)_n$N($R^6$)—$R^5$—C(O)—N moiety and to which the —C(O)—N($R^4$)—$R^3$—C(O)C(O)N$R^2R^1$ moiety is attached; L is —C(O)—, —OC(O)—, —$NR^{10}$C(O)—, —S(O)$_2$—, or —$NR^{10}$S(O)$_2$—; and n is 0 or 1, provided when

is substituted

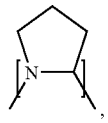

then L is —OC(O)— and $R^9$ is optionally substituted aliphatic; or at least one of $R^3$, $R^5$ and $R^7$ is ethylene, substituted with one substituent selected from the group consisting of an optionally substituted aliphatic group, an optionally substituted cyclic group or an optionally substituted aromatic group and wherein the ethylene is further optionally substituted with an aliphatic group substituent; or $R^4$ is optionally substituted aliphatic.

The compound of Structural Formula XXIV has the structure:

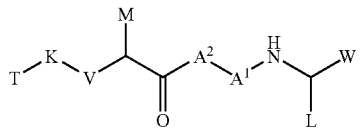

or a pharmaceutically acceptable salt, solvate, or ester thereof;

wherein in Formula XXIV:

W is:

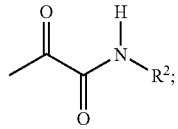

m is 0 or 1;

$R^2$ is hydrogen, alkyl, alkenyl, aryl, aralkyl, aralkenyl, cycloalkyl, cycloalkylalkyl, cycloalkenyl, cycloalkenylalkyl, heterocyclyl, heterocyclylalkyl, heterocyclylalkenyl, heteroaryl, or heteroaralkyl; wherein any $R^2$ carbon atom is optionally substituted with J;

J is alkyl, aryl, aralkyl, alkoxy, aryloxy, aralkoxy, cycloalkyl, cycloalkoxy, heterocyclyl, heterocyclyloxy, heterocyclylalkyl, keto, hydroxy, amino, alkylamino, alkanoylamino, arylamino, aralkanoylamino, carboxy, carboxyalkyl, carboxamidoalkyl, halo, cyano, nitro, formyl, acyl, sulfonyl, or sulfonamido and is optionally substituted with 1-3 $J^1$ groups;

$J^1$ is alkyl, aryl, aralkyl, alkoxy, aryloxy, heterocyclyl, heterocyclyloxy, keto, hydroxy, amino, alkanoylamino, arylamino, carboxy, carboxyalkyl, carboxamidoalkyl, halo, cyano, nitro, formyl, sulfonyl, or sulfonamido;

L is alkyl, alkenyl, or alkynyl, wherein any hydrogen is optionally substituted with halogen, and wherein any hydrogen or halogen atom bound to any terminal carbon atom is optionally substituted with sulfhydryl or hydroxy;

$A^1$ is a bond;

$R^4$ is alkyl, cycloalkyl, aryl, aralkyl, heterocyclyl, heterocyclylalkyl, heteroaryl, heteroaralkyl, carboxyalkyl, or carboxamidoalkyl, and is optionally substituted with 1-3 J groups;

$R^5$ and $R^6$ are independently hydrogen, alkyl, alkenyl, aryl, aralkyl, aralkenyl, cycloalkyl, cycloalkylalkyl, cycloalkenyl, heterocyclyl, heterocyclylalkyl, heteroaryl, or heteroaralkyl, and is optionally substituted with 1-3 J groups;

X is a bond, —C(H)(R7)-, —O—, —S—, or —N(R8)-;

$R^7$ is hydrogen, alkyl, alkenyl, aryl, aralkyl, heterocyclyl, heterocyclylalkyl, heteroaryl, or heteroaralkyl, and is optionally substituted with 1-3 J groups;

$R^8$ is hydrogen alkyl, aryl, aralkyl, heterocyclyl, heterocyclylalkyl, heteroaryl, heteroaralkyl, aralkanoyl, heterocyclanoyl, heteroaralkanoyl, —C(O)$R^{14}$, —SO$_2$$R^{14}$, or carboxamido, and is optionally substituted with 1-3 J groups; or $R^8$ and Z, together with the atoms to which they are bound, form a nitrogen containing mono- or bicyclic ring system optionally substituted with 1-3 J groups;

$R^{14}$ is alkyl, aryl, aralkyl, heterocyclyl, heterocyclylalkyl, heteroaryl, or heteroaralkyl;

Y is a bond, —CH$_2$—, —C(O)—, —C(O)C(O)—, —S(O)—, —S(O)$_2$—, or —S(O)(NR$^7$)—, wherein $R^7$ is as defined above;

Z is alkyl, aryl, aralkyl, cycloalkyl, cycloalkylalkyl, heterocyclyl, heterocyclylalkyl, heteroaryl, heteroaralkyl, —OR$^2$, or —N(R$^2$)$_2$, wherein any carbon atom is optionally substituted with J, wherein $R^2$ is as defined above;

$A^2$ is a bond or

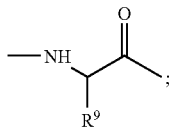

$R^9$ is alkyl, cycloalkyl, aryl, aralkyl, heterocyclyl, heterocyclylalkyl, heteroaryl, heteroaralkyl, carboxyalkyl, or carboxamidoalkyl, and is optionally substituted with 1-3 J groups;

M is alkyl, cycloalkyl, aryl, aralkyl, heterocyclyl, heterocyclylalkyl, heteroaryl, or heteroaralkyl, optionally substituted by 1-3 J groups, wherein any alkyl carbon atom may be replaced by a heteroatom;

V is a bond, —CH$_2$—, —C(H)(R$^{11}$)—, —O—, —S—, or —N(R$^{11}$)—;

$R^{11}$ is hydrogen or C$_{1-3}$alkyl;

K is a bond, —O—, —S—, —C(O)—, —S(O)—, —S(O)$_2$—, or —S(O)(NR$^{11}$)—, wherein R$^{11}$ is as defined above;

T is —R$^{12}$, -alkyl-R$^{12}$, -alkenyl-R$^{12}$, -alkynyl-R$^{12}$, —OR$^{12}$, —N(R$^{12}$)$_2$, —C(O)R$^2$, —C(=NOalkyl)R$^{12}$, or

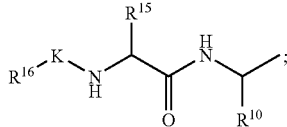

$R^{12}$ is hydrogen, aryl, heteroaryl, cycloalkyl, heterocyclyl, cycloalkyldienyl, or heterocycloalkylidenyl, and is optionally substituted with 1-3 J groups, or a first R$^{12}$ and a second R$^{12}$, together with the nitrogen to which they are bound, form a mono- or bicyclic ring system optionally substituted by 1-3 J groups;

$R^{10}$ is alkyl, cycloalkyl, aryl, aralkyl, heterocyclyl, heterocyclylalkyl, heteroaryl, heteroaralkyl, carboxyalkyl, or carboxamidoalkyl, and is optionally substituted with 1-3 hydrogens J groups;

$R^{15}$ is alkyl, cycloalkyl, aryl, aralkyl, heterocyclyl, heterocyclylalkyl, heteroaryl, heteroaralkyl, carboxyalkyl, or carboxamidoalkyl, and is optionally substituted with 1-3 J groups; and $R^{16}$ is hydrogen, alkyl, aryl, heteroaryl, cycloalkyl, or heterocyclyl.

The compound of Structural Formula XXV has the structure:

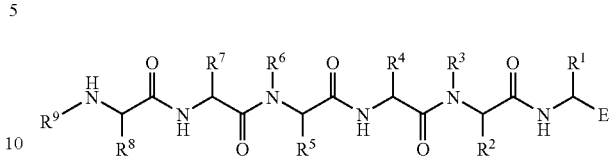

or a pharmaceutically acceptable salt, solvate, or ester thereof;

wherein in Formula XXV:

E represents CHO or B(OH)$_2$;

$R^1$ represents lower alkyl, halo-lower alkyl, cyano-lower alkyl, lower alkylthio-lower alkyl, aryl-lower alkylthio-lower alkyl, aryl-lower alkyl, heteroaryllower alkyl, lower alkenyl or lower alkynyl;

$R^2$ represents lower alkyl, hydroxy-lower alkyl, carboxy-lower alkyl, aryl-lower alkyl, aminocarbonyl-lower alkyl or lower cycloalkyl-lower alkyl; and $R^3$ represents hydrogen or lower alkyl;

or $R^2$ and $R^3$ together represent di- or trimethylene optionally substituted by hydroxy;

$R^4$ represents lower alkyl, hydroxy-lower alkyl, lower cycloalkyl-lower alkyl, carboxy-lower alkyl, aryllower alkyl, lower alkylthio-lower alkyl, cyano-lower alkylthio-lower alkyl, aryl-lower alkylthio-lower alkyl, lower alkenyl, aryl or lower cycloalkyl;

$R^5$ represents lower alkyl, hydroxy-lower alkyl, lower alkylthio-lower alkyl, aryl-lower alkyl, aryl-lower alkylthio-lower alkyl, cyano-lower alkylthio-lower alkyl or lower cycloalkyl;

$R^6$ represents hydrogen or lower alkyl;

$R^7$ represent lower alkyl, hydroxydower alkyl, carboxy-lower alkyl, aryl-iower alkyl, lower cycloalkyl-lower alkyl or lower cycloalkyl;

$R^8$ represents lower alkyl, hydroxy-lower alkyl, carboxy-lower alkyl or aryl-lower alkyl; and $R^9$ represents lower alkylcarbonyl, carboxy-lower alkylcarbonyl, arylcarbonyl, lower alkylsulphonyl, arylsulphonyl, lower alkoxycarbonyl or aryl-lower alkoxycarbonyl.

The compound of Structural Formula XXVI has the structure:

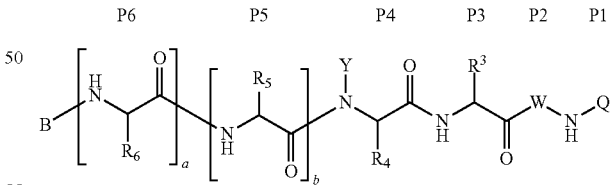

or a pharmaceutically acceptable salt, solvate, or ester thereof;

wherein in Formula XXVI:

B is an acyl derivative of formula R$_{11}$—C(O)— wherein R$_{11}$ is C1-10 alkyl optionally substituted with carboxyl; or R$_{11}$ is C$_6$ or C$_{10}$ aryl or C$_{7-16}$ aralkyl optionally substituted with a C$_{1-6}$ alkyl;

a is 0 or 1;

R$_6$, when present, is carboxy(lower)alkyl;

b is 0 or 1;

R$_5$, when present, is C$_{1-6}$ alkyl, or carboxy(lower)alkyl;

Y is H or $C_{1-6}$ alkyl;
$R_4$ is $C_{1-10}$ alkyl; $C_{3-10}$ cycloalkyl;
$R_3$ is $C_{1-10}$ alkyl; $C_{3-10}$ cycloalkyl;
W is a group of formula:

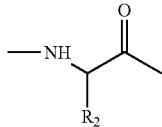

wherein $R_2$ is $C_{1-10}$ alkyl or $C_{3-7}$ cycloalkyl optionally substituted with carboxyl; $C_6$ or $C_{10}$ aryl; or $C_{7-16}$ aralkyl; or W is a group of formula:

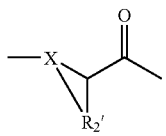

wherein X is CH or N; and
$R_2'$ is $C_{3-4}$ alkylene that joins X to form a 5- or 6-membered ring, said ring optionally substituted with OH; SH; NH2; carboxyl; $R_{12}$; $OR_{12}$, $SR_{12}$, $NHR_{12}$ or $NR_{12}R_{12}'$ wherein $R_{12}$ and $R_{12}'$ are independently:

cyclic $C_{3-16}$ alkyl or acyclic $C_{1-16}$ alkyl or cyclic $C_{3-16}$ alkenyl or acyclic $C_{2-16}$ alkenyl, said alkyl or alkenyl optionally substituted with $NH_2$, OH, SH, halo, or carboxyl; said alkyl or alkenyl optionally containing at least one heteroatom selected independently from the group consisting of: O, S, and N; or $R_{12}$ and $R_{12}'$ are independently $C_6$ or $C_{10}$ aryl or $C_{7-16}$ aralkyl optionally substituted with $C_{1-6}$ alkyl, $NH_2$, OH, SH, halo, carboxyl or carboxy(lower)alkyl; said aryl or aralkyl optionally containing at least one heteroatom selected independently from the group consisting of: O, S, and N;

said cyclic alkyl, cyclic alkenyl, aryl or aralkyl being optionally fused with a second 5-, 6-, or 7-membered ring to form a cyclic system or heterocycle, said second ring being optionally substituted with $NH_2$. OH, SH, halo, carboxyl or carboxy(lower)alkyl; $C_6$ or $C_{10}$ aryl, or heterocycle; said second ring optionally containing at least one heteroatom selected independently from the group consisting of: O, S, and N;

Q is a group of the formula:

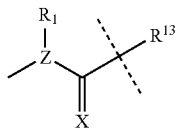

wherein Z is CH;
X is O or S;
$R_1$ is H, $C_{1-6}$ alkyl or $C_{1-6}$ alkenyl both optionally substituted with thio or halo;
and
$R_{13}$ is CO—NH—$R_{14}$ wherein $R_{14}$ is hydrogen, cyclic $C_{3-10}$ alkyl or acyclic $C_{1-10}$ alkyl or cyclic $C_{3-10}$ alkenyl or acyclic $C_{2-10}$ alkenyl, said alkyl or alkenyl optionally substituted with $NH_2$, OH, SH, halo or carboxyl; said alkyl or alkenyl optionally containing at least one heteroatom selected independently from the group consisting of: O, S, and N; or $R_{14}$ is $C_6$ or $C_{10}$ aryl or $C_{7-16}$ aralkyl optionally substituted with $C_{1-6}$ alkyl, $NH_2$, OH, SH, halo, carboxyl or carboxy (lower)alkyl or substituted with a further $C_{3-7}$ cycloalkyl, $C_6$ or $C_{10}$ aryl, or heterocycle; said aryl or aralkyl optionally containing at least one heteroatom selected independently from the group consisting of: O, S, and N;

said cyclic alkyl, cyclic alkenyl, aryl or aralkyl being optionally fused with a second 5-, 6-, or 7-membered ring to form a cyclic system or heterocycle, said second ring being optionally substituted with $NH_2$, OH, SH, halo, carboxyl or carboxy(lower)alkyl or substituted with a further $C_{3-7}$ cycloalkyl, $C_6$ or $C_{10}$ aryl, or heterocycle; said second ring optionally containing at least one heteroatom selected independently from the group consisting of: O, S, and N;

with the proviso that when Z is CH, then $R_{13}$ is not an α-amino acid or an ester thereof;

Q is a phosphonate group of the formula:

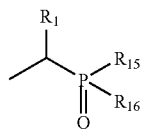

wherein $R_{15}$ and $R_{16}$ are independently $C_{6-20}$ aryloxy; and $R_1$ is as defined above.

In the above-shown structure of the compound of Formula XXVI, the terms P6, P5, P4, P3, P2 and P1 denote the respective amino acid moieties as is conventionally known to those skilled in the art. Thus, the actual structure of the compound of Formula XXVI is:

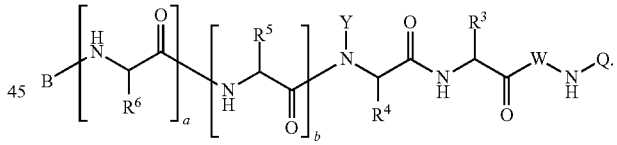

The compound of Structural Formula XXVII has the structure:

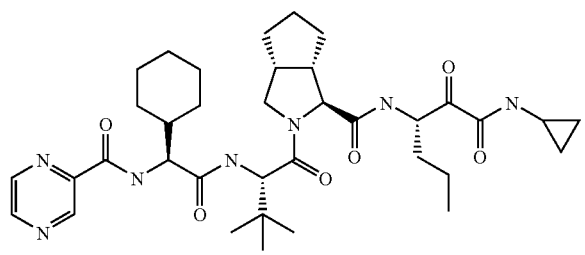 [SMILES: CCC[C@H](NC(=O)[C@@H]1[C@H]2CCC[C@H]2CN1C(=O)[C@@H](NC(=O)[C@@H](NC(=O)c1cnccn1)C1CCCCC1)C(C)(C)C)C(=O)C(=O)NC1CC1]

or a pharmaceutically acceptable salt, solvate, or ester thereof.

The compound of Structural Formula XXVIII has the structure:

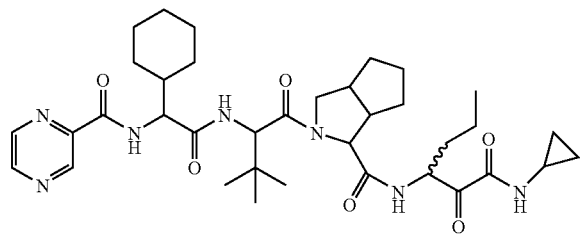 [SMILES: CCCC(NC(=O)C1C2CCCC2CN1C(=O)C(NC(=O)C(NC(=O)c1cnccn1)C1CCCCC1)C(C)(C)C)C(=O)C(=O)NC1CC1]

or a pharmaceutically acceptable salt, solvate, or ester thereof.

The present invention provides a pharmaceutical formulation comprising at least one active compound selected from Formula I to XXVIII wherein at least about 20% of at least one active compound initially contained in the formulation dissolves in 10 minutes. In select embodiments, at least about 60% of at least one active compound initially contained in the formulation dissolves in 10 minutes; at least about 50% of at least one active compound initially contained in the formulation dissolves in 20 minutes; at least about 80% of at least one active compound initially contained in the formulation dissolves in 20 minutes; at least about 65% of at least one active compound initially contained in the formulation dissolves in 30 minutes; at least about 90% of the active compound initially contained in the formulation dissolves in 30 minutes; at least about 80% of at least one active compound initially contained in the formulation dissolves in 45 minutes; at least about 95% of at least one active compound initially contained in the formulation dissolves in 45 minutes; at least about 85% of at least one active compound initially contained in the formulation dissolves in 60 minutes; at least about 98% of at least one active compound initially contained in the formulation dissolves in 60 minutes. In one embodiment, dissolution is tested at 37° C. in a USPII apparatus Paddle Stirrer filled with 900 mL of dissolution medium consisting of 0.5% sodium lauryl sulfate solution buffered with pH 6.8 sodium phosphate buffer.

EXAMPLES

There follows examples of the process of the present invention and a comparative example of particulate precipitated by a conventional stirred batch reactor. For each of the examples that follow, the compound of Formula B was prepared in accordance with the procedures detailed in published international. Patent Application No. WO 02/08244, which is incorporated by reference herein.

Unless noted to the contrary, all reagents are articles of commerce of USP or Food Grade purity and were used as received. Where noted, particle size information was obtained in accordance with the following procedure.

Figure 7:
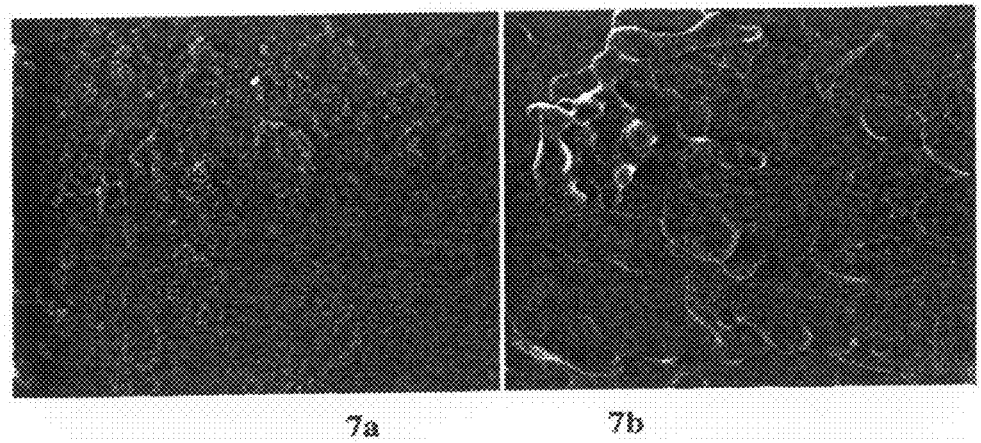
FIG. 7a presents an SEM 25× magnification photomicrograph showing granulate morphology before exposure to a temperature above its softening temperature.
FIG. 7b presents an SEM 25× magnification photomicrograph showing granulate morphology after exposure to a temperature above its softening temperature.

For the Examples which follow, particle size information was acquired by measuring the particulate material produced in the slurry using Focused Beam Reflectance Measurements (FBRM) performed with a Lasentec probe from Mettler Toledo in accordance with manufacturers directions for obtaining such measurements. Measurements were carried out on a sample of the slurry as obtained from the holding tank prior to vacuum distillation. The procedure and equipment can measure particulate materials over a size range of from 1 micron up to 1000 microns. Primary particle size was characterized qualitatively by Scanning Electron Microscopy (SEM). Changes in particle aggregation and aggregate morphology were observed by SEM under various conditions to determine softening point of the precipitated material. For SEM determination of softening point, a sample of the slurry was obtained periodically at each temperature interval as the slurry was heated. The solids in the sample were collected by filtration, dried under vacuum for 1 to 2 hours and the dried sample was examined using conventional SEM. With reference to FIG. 7a, photomicrographs of particulate material which had not undergone softening showed a nodular particle appearance under low magnification. With reference 7b, particles which had been exposed to temperatures above the softening point showed an absence of nodular particle appearance when examined at the same magnification. The softening point was inferred from the sampling temperature at which the precipitate began to show loss of nodular particle appearance when examined by SEM in this manner.

Verified by SEM observations, it was shown also that softening point could be determined from FBRM measurements (taken in accordance with manufactures instructions) made on a sample of the slurry undergoing controlled heating. Accordingly, a reactor containing the slurry was agitated at a rate of between 200 rpm and 300 rpm. The agitated slurry was heated from −20 C to above 150 C at a rate of 1 C/min. FBRM measurements were obtained continuously during the heating cycle and the softening point was determined to be the temperature corresponding to the maxima in the particle count curve over the heating regime.

Example I

A mixing tee was constructed from a stainless steel Tee fitting equipped with ⅜" compression fittings on the run legs and a ¼" NPT threaded branch leg by securing a length of ½" steel tubing connecting a pressure gauge (mechanical gauge obtained from Cole Parmer) and a metering flow control valve (1.5 gal/min. max, water, obtained from R.S. Crum & Company) to one run leg of the Tee to serve as an inlet for the anti-solvent. A ⅜" static tube mixer (Koflo Corporation sourced from Cole Parmer) was secured to the other run leg of the Tee, serving as an outlet. The branch leg of the Tee was fitted with a steel ¼" NPT X ⅛" compression fitting adapter (article of commerce) to serve as an inlet line for a solution of Formula B. A ⅛" 316 L stainless steel line fitted with a mechanical pressure gauge (Cole/Parmer) and a flow control metering valve (1.1 gal/min. max, water, obtained from R.S. Crum & Company) was connected to the compression adaptor fitted to the branch leg of the Tee fitting.

The control valve in the ⅜" inlet line (anti-solvent supply) was connected to a supply tank containing about 20 L of n-heptane. The control valve in the ⅛" inlet line (solution supply) was connected to a tank holding about 2.85 L of a 0.41 M solution of the compound of Formula B. The solution of Formula B was prepared by dissolving 608.5 g of the compound of Formula B into 2450 ml of methyl-tertiary-butyl-ether (MTBE).

The outlet of the static mixer of the mixing Tee was connected to a 5 L flask that was equipped with a mechanical stirrer, a Lasentec probe for determining particle size, and a heating jacket.

A precipitate slurry of the compound of Formula B was prepared by setting the flow control valves to supply 3400 ml/min. of n-heptane and 840 ml/min of the MTBE/compound of Formula B solution. The solution, anti-solvent, and mixing Tee were maintained at 20° C. When the temperature of the anti-solvent and solution had stabilized, the flow was commenced until 10.4 L of anti-solvent and 2.85 L of solution had passed through the mixing Tee and into the flask. FBRM measurements taken in the slurry in the flask indicated that the agglomerated particulate had an average chord length of 15.8 microns with a particulate chord length range of from about 1 micron to about 110 microns. An aliquot of the slurry thus produced was also evaluated to determine the softening point of the precipitate therein. Accordingly, the aliquot was heated at a rate of 1 C/min. in a stirred 3 L reactor while FBRM measurements were performed using the Lasentec® probe. In this manner the softening temperature was determined to be at 36.2 C.

The particulate prepared above was recovered by pressure filtration and vacuum dried under house vacuum (approximately 60 to 70 torr) for 2 hours at 25 C followed by 8 hours of house vacuum at 35 C. The product was finish-dried at 45 C under house vacuum for an additional 16 hours. The dried particulate was evaluated and found to have a primary particle size ranging from less than 1 micron up to about 2 microns. The specific surface area (BET absorption method) was determined to be about 19.11 m2/g. The bulk density of isolated material was determined by weighing a 25 ml (unpacked) sample. The bulk density was found to be 0.3 g/ml.

A second run was conducted in the above-described equipment using 3.7 L of a 0.24 M MTBE solution of the compound of Formula B prepared by dissolving 456 g of the compound of Formula B in 3600 ml of MTBE. The anti-solvent flow control valve was set to supply 3750 ml/min. of n-heptane and the solution control valve was set to supply 635 ml./min. of the solution of the compound of Formula B. The solution, anti-solvent, and mixing equipment were all maintained at 20° C. When the temperature had been stabilized, flow was commenced until 20.3 L of anti-solvent and 3.7 L of the solution had passed through the mixing Tee and into the holding tank.

A 2500 ml aliquot of the slurry passed into the holding tank was vacuum distilled at 32° C. under about 60 torr of vacuum until it was reduced to about 35% of its original volume, approximately 870 mL. The softening point of the precipitate in the slurry was determined using the above-described FBRM measurement, and found to be 51.6° C. The precipitate was recovered by vacuum filtration, washed with a single 1 L aliquot of n-heptane and evaluated for residual MTBE. The wet filter cake was found to contain less than 1 wt. % residual MTBE. The precipitate was vacuum dried under house vacuum for 8 hours at 35° C., and there after for an additional 16 hours at 45° C.

The isolated material was found to have a primary particle size of less than 1 micron and an agglomerated average particle size of 11 microns with a particle size range distribution of from about 2 microns to about 30 microns. BET surface area measurements indicated that the particulate has an average bulk surface area of about 10.3 m²/g, with samples ranging from about 5 m²/g to about 25 m²/g. The bulk density average of the isolated particulate was determined to be 0.191 g/m³, with bulk density ranging from about 15 g/cm³ to about 0.35 g/cm³.

Example II

A larger scale mixing Tee was fabricated utilizing a plumbing Tee having a ½" nominal OD run, each leg of which was terminated with a ½" compression fitting, and a 3/16" branch leg utilizing the same type of arrangement of flow meters and pressure gauges utilized in the smaller mixing Tee described in Example I. The outlet of the mixing tee was connected to a static mixer having an outside diameter of ½". A slurry was made by employing 2,900 ml/min of n-heptane held at a temperature of 5° C. (hence a Reynolds number of 9700) and 716 ml./min of a solution comprising 0.41 M MTBE solution of the compound of Formula B held at a temperature of 5° C. (hence a Reynolds number of 2700). The output of the mixing Tee was collected in a stirred holding tank. With the stirrer running the contents of the tank were placed under a vacuum of approximately 30 to 50 torr (house vacuum), and the supernatant liquid of the slurry was vacuum distilled from the holding tank at a temperature of from about 12° C. to about 17° C. Utilizing vacuum distillation the volume of the slurry was reduced to about 40% of the original volume, about 600 L. The precipitated material was recovered by centrifugation filtration. The filter cake was washed with about 240 L of n-heptane. The wet filter cake was vacuum dried under house vacuum (approximately 30 to 50 torr) for 4 hours at 25° C., followed by 10 hours at 35° C. and then for 12 additional hours at 45° C.

During the precipitation run, aliquots of the slurry in the holding tank were evaluated by placing a sample of from about 500 ml volume to about 700 ml volume in a vessel and heating while monitoring the particulate material in the slurry for its softening point using FBRM measurement. The results of this study are reported in FIG. 3. As shown in FIG. 3, with increasing concentration of the slurry by distilling off MTBE and water, the softening point of the particulate material produced is elevated. Analysis of the precipitate obtained from the slurry showed that it had a bulk surface area of 8.14 m²/g and a bulk density of 0.23 g/cm³, and a median particulate size of 1.57 microns.

Example III

A mixing chamber was fabricated using a plumbing Tee having a 1" nominal OD run, each leg of which was terminated with a 1" compression fitting, and a ¼" branch leg. The same configuration of flow meters and pressure gauges that was utilized in the apparatus described above in Example I was employed in this example. A slurry was made by employing 20,000 ml/min of n-heptane held at a temperature of −20° C. (hence a Reynolds number of 23,650) and 5,000 ml./min of a solution comprising 0.32 M MTBE solution of the compound of Formula B held at 0° C. (hence a Reynolds number of 10,650). The output of the mixing Tee was collected for about 5.5 hours in a stirred holding tank fitted with a temperature controlled jacket, a vacuum line and an agitating paddle. When the vessel was sealed the slurry was warmed from the temperature collected by running the jacket temperature at 15° C. When the slurry had attained a temperature of 12.1° C. the vessel was evacuated until a pressure of −0.800 bar gauge (barg) was attained and distillation began. During distillation the pressures and jacket temperatures shown in the table below were maintained until the slurry had attained a volume that was 33.33% of the initially collected slurry volume. Analysis of the precipitate isolated from the slurry showed that it had a bulk surface area of 7.2 m²/g, a bulk density of 0.18 g/cm³, a median particulate size of 1.46 microns, and a particulate size range of from 0.25 microns to 18 microns.

| HCV-Y Distillation Profile | | | |
|---|---|---|---|
| Pressure (barg) | Jacket Temperature (° C.) | % total batch volume distilled | Batch volume distilled (L) (X = 320 kg) |
| −0.800 | 15 | NA | 9600 L [1] |
| −0.905 | 20 | 0-2 | 0-190 |
| −0.905 | 21 | 2-4 | 190-380 |
| −0.905 | 22 | 4-6 | 380-580 |

-continued

HCV-Y Distillation Profile

| Pressure (barg) | Jacket Temperature (° C.) | % total batch volume distilled | Batch volume distilled (L) (X = 320 kg) |
|---|---|---|---|
| −0.905 | 23 | 6-8 | 580-770 |
| −0.905 | 25 | 8-10 | 770-960 |
| −0.905 | 26 | 10-13 | 960-1250 |
| −0.905 | 28 | 13-16 | 1250-1540 |
| −0.908 | 28 | 16-18 | 1540-1730 |
| −0.910 | 30 | 18-22 | 1730-2110 |
| −0.914 | 32 | 22-26 | 2110-2500 |
| −0.918 | 32 | 26-30 | 2500-2880 |
| −0.924 | 32 | 30-34 | 2880-3270 |
| −0.932 | 32 | 34-38 | 3270-3650 |
| −0.938 | 32 | 38-42 | 3650-4030 |
| −0.942 | 32 | 42-46 | 4030-4420 |
| −0.950 | 32 | 46-52 | 4420-4990 |
| −0.956 | 32 | 52-60 | 4990-5760 |
| −0.970 | 32 | 60-66.67 | 5760-6400 |

[1] initial slurry volume collected

Figure 8:
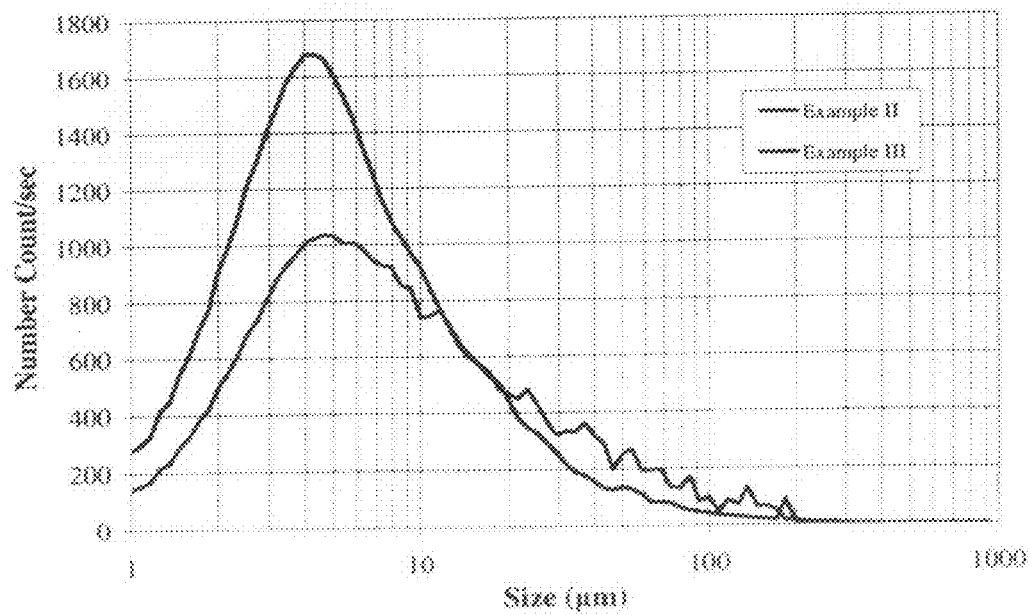
FIG. 8 presents a comparison of chord length in precipitated agglomerates as a function of the Reynolds numbers attained by the combining anti-solvent and solution streams.

The graph shown in FIG. 8 depicts a comparison in the chord length distribution of the precipitate produced in Examples II (Reynolds number for anti-solvent=9700, Reynolds number for the solution=2700) with that produced in Example III (Reynolds number for anti-solvent=23,650, Reynolds number for the solution=10,650). As can be seen from FIG. 8, the conditions used in Example III yielding higher Reynolds numbers resulted in higher nucleation rates, as evidenced by the increased particle count, and provided a narrower chord length distribution.

Additional runs were conducted as described in the table below. Each separate group of runs, denoted by group designated "A", "B", and "C", was carried out using the equipment described below the table with the resulting primary particle sizes and aggregated particulate prepared as shown in the table below.

| Example* | Concentration (M) MTBE solution of Formula B | Flow rate (ml/min) MTBE solution | Heptane Flow rate (ml/min) | Primary Particle size observed (microns) | Aggregated particle size (microns) | BET Surface area (m²/g) |
|---|---|---|---|---|---|---|
| A1 | 0.23 | 635 | 4100 | Submicron to 2 microns | 10-20 microns | 30.19 |
| A2 | 0.23 | 420 | 4125 | Submicron to 2 microns | 10-20 microns | 16.44 |
| A3 | 0.41 | 640 | 4115 | Submicron to 2 microns | 20-30 micros | 17.41 |
| B1 | 0.23 | 717 | 4200 | Submicron to 1 microns | 10-20 microns | 32.75 |
| B2 | 0.23 | 717 | 4200 | Submicron to 1 microns | 10-20 microns | 25.68 |
| B3 | 0.23 | 717 | 4200 | Submicron to 1 microns | 10-20 microns | 32.00 |
| B4 | 0.23 | 717 | 4200 | Submicron to 1 microns | — | 24.24 |
| C1 | 0.32 | 5000 | 20000 | Submicron to 2 microns | 0.25-25.5 microns | 24.85 |
| C2 | 0.32 | 5000 | 20000 | Submicron to 2 microns | 0.25-18 microns | 32.41 |
| C3 | 0.32 | 5000 | 20000 | Submicron to 2 microns | 10-20 microns | — |
| C4 | 0.32 | 5000 | 20000 | Submicron to 2 microns | 10-20 microns | — |

*Note:
Batches denoted by "A" were carried out using a mixing Tee having a ½" nominal run outside diameter and a nominal ³/₁₆" branch leg outside diameter, batches denoted "B" were carried out using a mixing Tee having a ½" nominal run outside diameter and a nominal ⅛" branch leg outside diameter, and batches denoted "C" were carried out using a mixing Tee having a 1" nominal run outside diameter and a ¼" nominal branch leg outside diameter.

Figure 9:
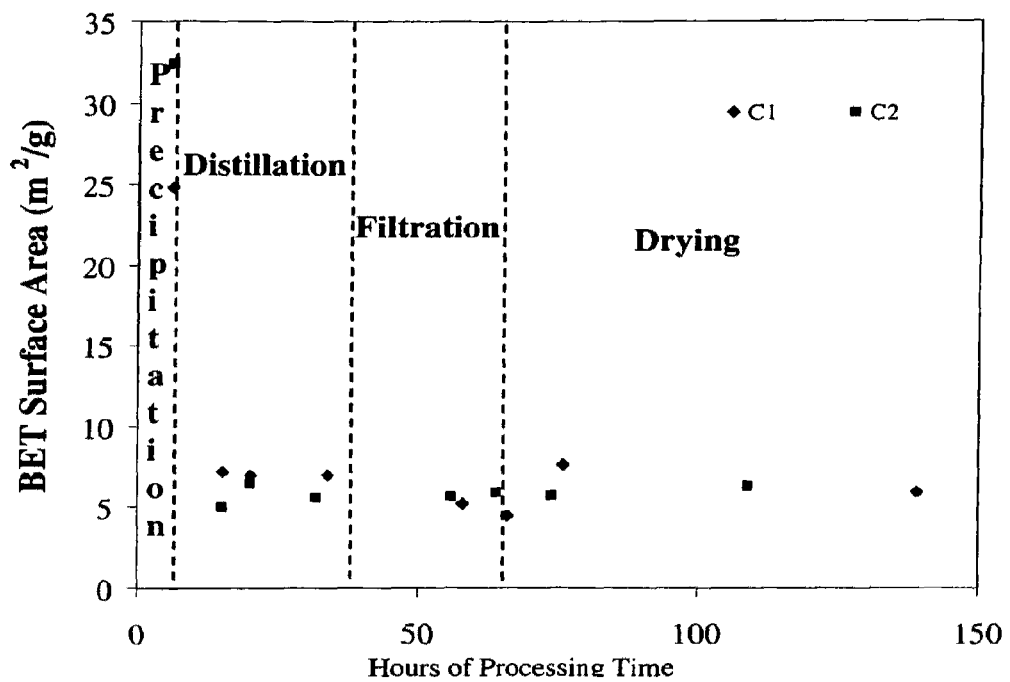
FIG. 9 presents a correlation between processing stage and bulk surface area in precipitated and agglomerated materials.

The slurry produced in each of Examples C1 and C2 was subjected to a distillation step. The bulk surface area of the precipitate produced in C1 was reduced from 24.85 m²/g to 6.13 m²/g, and the precipitate produced in C2 was reduced from 32.41 m²/g to 6.31 m²/g in the final granulate product. FIG. 9 indicates for these two runs that the bulk surface area is reduced in the distillation step and remains thereafter substantially the same throughout the remainder of the process.

Comparative Example I

A comparative example of a precipitate of the compound of Formula B was prepared utilizing a 3 L stirred dish bottom batch reactor equipped with a 90 mm retreat curve impeller containing 1780 ml of n-heptane maintained at −20° C. A 330 ml volume of MTBE solution containing 132 mg of the compound of Formula B per milliliter of solution was introduced, with stirring (550 rpm), over a period of 29 min into the anti-solvent. The resulting slurry was distilled under house vacuum (30-60 Torr) to a volume of 1600 ml. The precipitate was collected by pressure filtration, washed with 400 ml heptane and dried in an agitated filter dryer at a jacket temperature of 35° C. for 15.5 hours under full vacuum followed by 7.3 hrs at 50° C. The filtrate contained about 5% wt MTBE. The collected material had a bulk density of 0.16 g/ml, a BET surface area of only 1.76 m²/g indicating large primary particle size. SEM examination of the particulate showed that the particles were fused (melted). The softening point of the wet cake was determined to be below about 30° C.

In comparison to the batch precipitation material the precipitate prepared in accordance with the present invention is more uniform, and has an improved bulk density permitting smaller dosage forms for an equivalent active content. Moreover, the increased softening point of the isolated particulate material permits more aggressive drying conditions, shortening processing time.

There follows examples of using the precipitate prepared as shown above to prepare pharmaceutical formulations Pharmaceutical Formulations Example pharmaceutical formulations described below were prepared either in laboratory scale equipment (3 Kg scale) and comprised granulation in a low shear mixer, drying in an oven, blending in a Tumble blender and manual capsule filing, or in industrial scale equipment (40 Kg or larger) which included a Collette High Shear granulator, a Glatt Fluid bed dryer, a Bohle bin blender, a Quadro Comil screen mill (for both wet and dry milling), and a Bosch capsule filling machine. In all of the examples, operations were carried out in accordance with GMP standard pharmaceutical manufacturing processes and standards of the industry, including sieving, granulation, milling, fluid bed drying and powder mixing.

Unless noted to the contrary, all materials utilized in the formulations were articles of commerce meeting the current requirements of the United States Pharmacopeia/National Formulary (USP/NF). The active pharmaceutical ingredient used in the preparation of pharmaceutical formulations was prepared in accordance with that of Example II above. All API was used as prepared and had characteristic bulk surface area, average chord length, average particle size, bulk density and bulk surface area in accordance with the foregoing description of the precipitated particulate material.

Example IV

40 Kg Preparation of Pharmaceutical Formulation

A granular pharmaceutical formulation of the invention was prepared on the 40 Kg batch scale using the following procedure. Into a Collette granulator/high speed mixer equipped with a mixer blade and a chopper blade was placed 2.000 Kg of microcrystalline cellulose (Avicel PH102, FMC), 1.200 Kg of croscarmellose sodium (NF grade), 6.000 Kg of pregelatinized starch 1500 (Colorcon), 4.586 Kg of lactose monohydrate (NF, impalpable grade, Foremost Farms), and 21.014 Kg of the Compound of Formula B prepared in accordance with Example II above, having a median bulk surface area of 8.14 $m^2/g$ and a bulk density of 0.23 $g/cm^3$, and a median particulate size of 1.57 microns. The weight of API used reflects an adjustment in the mass from a theoretical 20 Kg to compensate for the activity of the API. Accordingly, 21.014 Kg of the API employed has an activity equivalent to 20 Kg of a theoretical material having 100% activity. The API and excipients present in the mixer were dry-blended by operating the high-shear mixer at 15.7 feet/sec. for 2 minutes to provide a homogeneous powder. The powder was wet-granulated using a solution comprising 1.200 Kg sodium lauryl sulfate (NF/USP, Stepan) dissolved in 17 Kg of purified water carried out by spraying 3 Kg of the solution/minute onto the homogeneous powder in the mixer/granulator with the mixer blade operating at 18.9 ft/sec. and the chopper blade operating at 2500 RPM. When all of the granulating fluid had been sprayed, the tank which contained the granulating fluid and lines feeding the granulating fluid to the spray apparatus were rinsed by spraying an additional 8.10 Kg of purified water into the granulator/mixer. Thereafter the granulator was operated with cooling water running through the granulator jacket to maintain the granulate at a temperature below 30° C. until the mixer power requirement rose to 11.1 kW. At the end of the granulation time the wet granulate thus prepared was discharged into a Quadro Comil equipped with a 0.375 inch square-hole screen and a round impeller bar. The entire amount of wet granulate was passed through the mill. The milled, wet granulate was transferred to a Glatt WSG60 fluid bed processor and dried at 55° C., 1000 CFM air flow until a sample showed a moisture weight loss on drying of 2.2 wt %.

The entire amount of dried granulate prepared was dry-milled/sieved using a Quadro Comil equipped with a 0.040 inch hole size greater screen and a round bar impeller. A second batch of granular material, prepared in substantially the same manner described above was also milled under the same conditions and combined with the first batch of milled material to give a combined weight of 69,560 g of milled material. This entire amount of milled material was transferred to a 400 L Bohle bin blender along with 3,864 g of microcrystalline cellulose (extragranular, Avicel PH102, a weight of microcrystalline cellulose equal to the intragranular microcrystalline cellulose present in the milled material) and 2,319 g croscarmellose sodium (extragranular, NF grade, a weight of croscarmellose sodium equal to the amount of intragranular croscarmellose sodium present in the milled material). The constituents of the bin blender were dry-blended at 8 RPM for about 30 minutes to yield a homogeneous particulate blend. Magnesium stearate (1,546 g, Greven,) was passed through a 30 mesh screen and added to the Bohle blender containing the particulate blend. The contents of the blender were dry blended for 9 minutes at 8.0 RPM, yielding a homogeneous granular pharmaceutical formulation having a bulk density of 0.468 g/ml and a tapped density of 0.642 g/ml comprising 50 wt. % of API (intragranular), and comprising 10 wt. % of microcrystalline cellulose (5 wt. % intragranular, 5 wt. % extragranular), 14 wt. % lactose monohydrate (intragranular), 6 wt. % croscarmellose sodium (3 wt. % intragranular, 3 wt. % extragranular) 15 wt. % pregelatinized starch (intragranular), 3 wt. % sodium lauryl sulfate (intragranular), and 2 wt. % magnesium stearate (extragranular).

PK Results of the Granular Pharmaceutical Formulation

A 0.400 g portion (average) of the granular pharmaceutical formulation prepared above was charged, into size 0 capsules using a Bosch capsule filler equipped with a 19 mm dosing disk, corresponding to 200 mg of active material/capsule.

Figure 10:
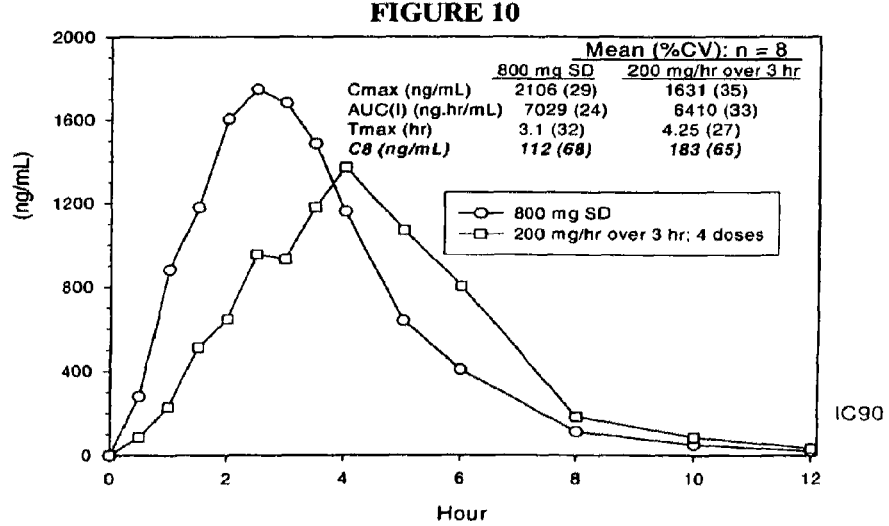
FIG. 10 presents a comparison in Cmax and AUC between 800 mg doses administered as a single dose and administered as multiple 200 mg doses over 3 hours (see Example V, infra, for details).

Samples of these capsules were administered to healthy volunteers, either 4 capsules at once or spaced at 1 hour dosing intervals over a three hour period. The results are shown in FIG. 10, which indicates a Cmax (single dose) at 3.1 hours of 2106 ng/ml and a Cmax (multiple dose) at 4.25 hours of 1631 ng/ml. The corresponding single dose AUC was found to be 7029 ng·hr/ml and the corresponding multiple dose AUC was found to be 6410 ng·ml/hr, indicating that the formulation can provide therapeutic levels of the HCV protease inhibitor API contained therein.

Example V

Pharmaceutical Formulations

Additional batches of the granular pharmaceutical formulation were prepared using the process described in Example IV, albeit utilizing appropriate scale equipment for larger (250 Kg) and smaller (3 Kg) batch sizes, as indicated in the table below. With reference to the table below, the weights of the constituents used in each batch are reported (half of the croscarmellose sodium and microcrystalline cellulose reported is present in the product granular pharmaceutical formulation as intragranular material and half was blended with the granular material in the preparation of the formulation in accordance with the process described in Example IV, and therefore is extragranular material).

| | Batch Size | | |
|---|---|---|---|
| | 3 kg | 40 kg[a] | 250 kg[a] |
| Constituents | kg/Batch | kg/Batch | kg/Batch |
| SCH 503034 | 1.5 (50 wt. %) | 20 (50 wt. %) | 125 (50 wt. %) |
| Lactose Monohydrate | 0.27 (9 wt. %) | 5.6 (14 wt. %) | 35 (14 wt. %) |
| Microcrystalline Cellulose | 0.3 (10 wt. %)[b] | 4 (10 wt. %)[b] | 25 (10 wt. %)[b] |
| Pregelatinized Starch | 0.45 (15 wt. %) | 6 (15 wt. %) | 37.5 (15 wt. %) |
| Croscarmellose Sodium | 0.18 (6 wt. %)[b] | 2.4 (6 wt. %)[b] | 15 (6 wt. %)[b] |
| Tartaric acid | 0.15 (5 wt. %) | — | — |
| Sodium Lauryl Sulfate | 0.09 (3 wt. %) | 1.2 (3 wt. %) | 7.5 (3 wt. %) |
| Magnesium Stearate | 0.06 (2 wt. %) | 0.8 (2 wt. %) | 5 (2 wt. %) |
| Total Batch Weight | 3 | 40 | 250 |
| Process Equipment: | | | |
| Granulator | Low Shear Mixer | High Shear Granulator | High Shear Granulator |
| Dryer | Oven | Fluid Bed Dryer | Fluid Bed Dryer |
| Blender | Tumble Blender | Tumble Blender | Tumble Blender |
| Capsule Filling Machine | Encapsulator (Dosing disc) | Encapsulator (Dosing disc) | Encapsulator (Dosing disc) |

[a]Two blends can be combined into one blend before encapsulation,
[b]Half is intragranular, half extragranular Capsule Dissolution Characteristics Aliquots of each of the granular pharmaceutical formulation prepared above were placed into capsules and tested for dissolution characteristics in accordance with the following process. The dissolution testing apparatus employed was a USPII apparatus Paddle Stirrer filled with 900 mL of dissolution medium consisting of 0.5% sodium lauryl sulfate solution buffered with pH 6.8 sodium phosphate buffer. The dissolution tests were conducted at 37° C. The tests were carried out by stabilizing the dissolution medium at the test temperature with the paddles set at 50 RPM. Test capsules were dropped into the dissolution medium with the paddles actuated. Periodically aliquot samples of the dissolution media were withdrawn and analyzed by HPLC for active content. The total amount of active present in the dissolution media was calculated based on the HPLC determination and reported as a percentage of the total amount of active initially contained in the capsule dissolved into the dissolution media. The results for a representative sample taken from capsules prepared with each batch size are shown below in the table below as an average of 6 capsules.

| | Source | | |
|---|---|---|---|
| Constituents | 3 kg Batch mg/cap | 40 kg Batch mg/cap | 250 kg Batch mg/cap |
| Precipitated Compound of Formula B | 200 | 200 | 200 |
| lactose Monohydrate | 36 | 56 | 56 |
| Mircrocrystalline Cellulose | 40 | 40 | 40 |
| Pregelatinized Starch | 60 | 60 | 60 |
| Croscarmellose Sodium | 24 | 24 | 24 |
| Sodium Lauryl Sulfate | 12 | 12 | 12 |
| Tartaric acid | 20 | — | — |
| Magnesium Stearate | 8 | 8 | 8 |
| Capsule Fill Weight | 400 | 400 | 400 |
| Dissolution Time: | % API Dissolved | % API Dissolved | % API Dissolved |
| 10 minutes | 65 | 78 | 83 |
| 20 minutes | 84 | 88 | 92 |
| 30 minutes | 92 | 91 | 94 |
| 45 minutes | 98 | 95 | 96 |
| 60 minutes | 100 | 98 | 97 |

Comparative PK Results-1

Capsules prepared using a formulation as described above for the 3 Kg batch and a formulation prepared by the same process, albeit on a laboratory scale and not employing sodium lauryl sulfate in the granulating fluid were administered to 12 healthy human volunteers. Accordingly, each of the test subjects received 2 capsules containing 200 mg of the API in a single administration. Blood samples were collected from each volunteer at predose (hour 0) and 0.5, 1, 1.5, 2, 2.5, 3, 4, 5, 6, 7, 8, 9, 10, 12, and 24 hours post administration with the average concentration values for those subjects receiving the API presented graphically in FIG. 6 as the trace represented by the square datapoints. The serum drug levels of the volunteers receiving active drug are reported also in tabular form below, which table contains one column of results for each of the 3% SLS and without SLS formulations. The pharmacokinetic (PK) data from this study showed that for the dosage form prepared with sodium lauryl sulfate in the granulating fluid the mean maximum plasma concentration following a single administration (Cmax) was on average 864 ng/ml, the median time (hours) to reach maximum concentration (Tmax) was 1.71 hours, and the AUC 24 (areas under the plasma concentration time curve in ng·hr/mL for 24 hours post administration) was 2540.

| Time from administration | Plasma Concentration (ng/ml) | |
|---|---|---|
| (hours) | 0% SLS | 3% SLS |
| 0 | 0.0 | 0 |
| 0.5 | 9.34 | 386.1 |
| 1.0 | 86.9 | 671.1 |
| 1.5 | 183.9 | 701.8 |
| 2.0 | 220.0 | 525.8 |
| 2.5 | 211.5 | 484.2 |
| 3.0 | 208.3 | 400.1 |
| 4.0 | 137.9 | 263.9 |
| 5.0 | 173.3 | 145.5 |
| 6.0 | 127.4 | 88.6 |
| 7.0 | 99.8 | 57.7 |
| 8.0 | 77.0 | 45.1 |
| 9.0 | 49.0 | 35.9 |
| 10.0 | 52.8 | 32.4 |
| 12.0 | 34.3 | 19.7 |
| 24.0 | 10.4 | 6.15 |

Figure 6:
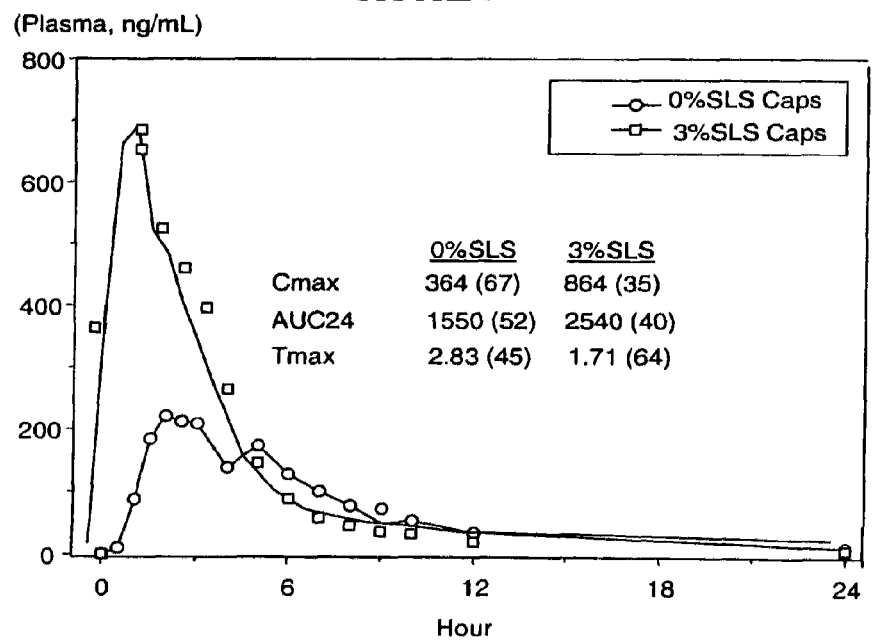
FIG. 6 presents a graphic representation of the effects on bioavailability of using SLS in a formulation compared with a similarly prepared formulation that does not employ SLS.

With reference to FIG. 6, when compared to a formulation not containing sodium lauryl sulfate (trace with open circle datapoints), the present formulation shows improved bioavailability upon administration.

Comparative PK Results-2

A study was conducted to evaluate the effect of both a therapeutic (800 mg TID) and a supratherapeutic (1200 mg TID) dose of the compound of Formula B at steay-state on QT/QTc intervals, as measured by mean maximum change from time-matched baseline ECG recordings compared to placebo. The study was a multi-period, multiple-dose, placebo and active control study in healthy volunteers conducted in a randomized, evaluator blind, 4-way crossover manner. A formulation of the invention prepared as described above herein in Example IV (40 kg. batch scale) comprising the compound of Formula B, was administered in capsules.

Thirty-six subjects who met entry criteria received one of four study treatments for Days 1 to 5 of each treatment period. This study was conducted in a 4-way crossover manner so that subjects were randomized to receive the 4 study treatments in one of four sequences. Prior to treatment crossover, subjects completed an approximately 1-week outpatient washout period. Each treatment group consisted of oral dosing for 5 days of: A) a formulation of the invention comprising the compound of Formula B-800 mg TID; B) a formulation of the invention comprising the compound of Formula B-1200 mg TID; C) moxifloxacin-400 mg QD; and D) placebo.

API Source:
Treatment A:
  A formulation of the invention comprising the compound of Formula B, 800 mg (4×200 mg Capsules) orally Q8° with two placebo capsules
Treatment B:
  A formulation of the invention comprising the compound of Formula B, 1200 mg (6×200 mg Capsules) orally Q8° for 4 days then as a single AM dose on Day 5

Pharmacokinetic samples for the determination of plasma concentrations of the compound of Formula B were collected on Day 5 of each period. PK samples were collected predose (0 hour), 1, 2, 3, 4, 6, 8, 12, and 24-hours postdose.

The following table shows the CV (coefficient of variance) around the mean of the compound of Formula B after multiple (Day 5) oral doses of a formulation of the invention comprising the compound of Formula B in healthy subjects.

Mean (CV) Pharmacokinetic Parameters

| Parameters | Mean (CV, %) | |
| --- | --- | --- |
| | Formula B 800 mg (n = 31)[b,c] | Formula B1200 mg (n = 35)[c] |
| Tmax[a] (hr) | 2.00 (1.00-4.00) | 2.00 (1.00-4.00) |
| Cmax (ng/mL) | 1690 (19)[d] | 1940 (24)[e] |
| Cmin (ng/mL) | 61.9 (41) | 79.9 (46) |
| AUC(τ) (ng · hr/mL) | 5320 (23)[f] | 6500 (22)[g] |
| $t_{1/2}$ (hr) | 2.31 (68) | 3.01 (73) |
| CL/F (L/hr) | 158 (22) | 196 (31) |
| Vd/F (L) | 530 (84) | 879 (85) |

Figure 11:
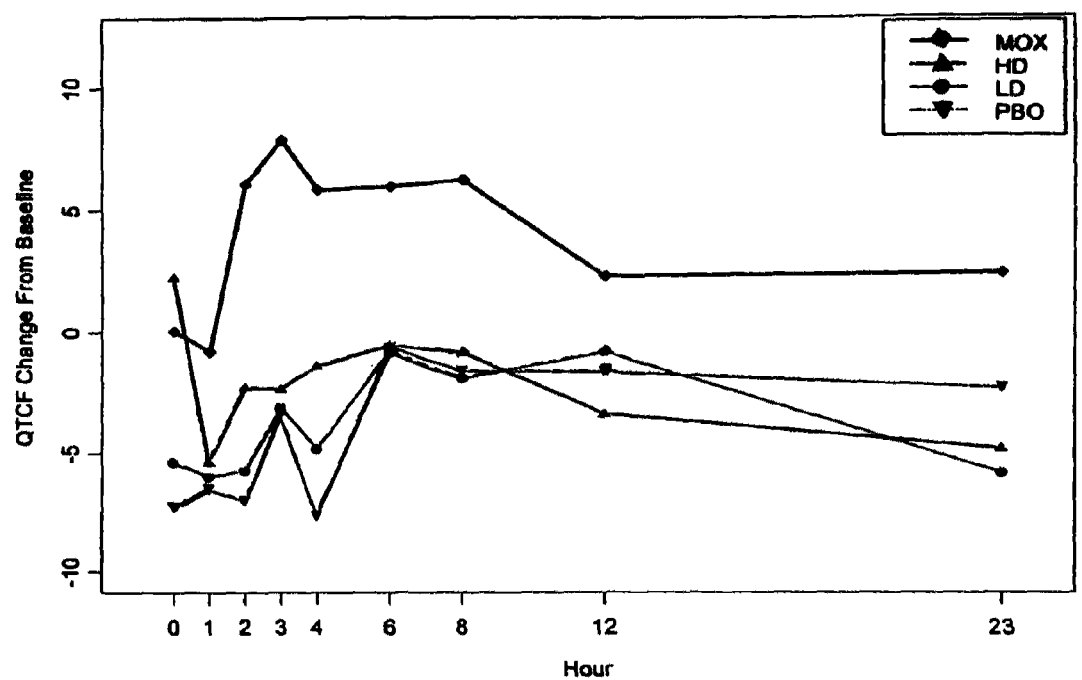
FIG. 11 presents the mean QTcF change from baseline on Day 5 for formulations of the present invention comprising 800 mg (LD) and 1200 mg (HD) doses of the compound of Formula B, moxifloxacin (MOX) and placebo (PBO) versus time.

[a]Median (range)
[b]The four Subjects (101, 109, 160, and 166) were excluded from analysis of the Formula B 800 mg dose group as treatment at this dose was not completed
[c]Subject 105 was excluded from the analysis of both Formula B treatment groups due to early withdrawal
[d]Individual Cmax values ranged from about 1150 ng/ml to about 2500 ng/ml
[e]Individual Cmax values ranged from about 1100 ng/ml to about 3150 ng/ml
[f]Individual AUC(τ) values ranged from about 3250 ng · hr/mL to about 8900 ng · hr/mL
[g]Individual AUC(τ) values ranged from about 2500 ng · hr/mL to about 9400 ng · hr/mL
Abbreviations used in the table:
AUC(τ) = area under the concentration-time curve during the dosing interval, Cmax = maximum observed plasma concentration, Cmin = minimum observed plasma concentration, CL/F = apparent total body clearance, $t_{1/2}$ = terminal phase half-life, Tmax = time of observed maximum concentration, Vd/F = apparent volume of distribution
The values for Formula B represent the calculated value from the sum of its diastereomers FIG. 11 presents the mean QTcF change from a time-matched baseline. The figure shows that a formulation of the invention comprising compound of Formula B does not prolong the QT interval at either the 800 mg therapeutic dose (LD) or the 1200 mg supratherapeutic dose (HD) relative to the placebo. The moxifloxacin results, which show a lengthened QT/QTc interval, were included as a positive control.

Example VI

Pharmaceutical Formulations Using Other API

Using the above-described precipitation process, an API will be prepared for other compounds of the structure of Formula I (other than the compound of Formula B exemplified herein) and of the structure of Formulae II to XXVIII described herein. The precipitated particulate material will be incorporated into a pharmaceutical formulation by substituting it for the API in the process described above for preparation of granular pharmaceutical formulations in Examples IV and V above.

The above description of the invention is intended to be illustrative and not limiting. Various changes or modifications in the embodiments described herein may occur to those skilled in the art. These changes can be made without departing from the scope or spirit of the invention

The invention claimed is:
1. A granular pharmaceutical formulation comprising 50 wt. % API, 14 wt. % lactose monohydrate (intragranular), 5 wt. % intragranular microcrystalline cellulose, 5 wt. % extragranular microcrystalline cellulose, 3 wt. % intragranular croscarmellose sodium, 3 wt. % extragranular croscarmellose sodium, 15 wt. % pregelatinized starch (intragranular), 3 wt. % sodium lauryl sulfate (intragranular), and 2 wt. % magnesium stearate (extragranular), wherein
said API is an agglomerated particulate comprising a compound of Formula B,
said agglomerated particulate having a median bulk surface area of from about 5 m²/g to about 12 m²/g, an agglomerated particulate particle size of from about 1 micron to about 2.5 microns, an agglomerated particulate particle size distribution of from about 1 micron to about 50 microns, a bulk density of from about 0.15 g/ml to about 0.19 g/ml and a softening point of from about 20° C. to about 50° C.,
said agglomerated particulate is prepared by a process comprising combining a 0° C. stream of a solution comprising methyltertiarybutyl ether (MTBE) having dissolved therein 166 mg/ml of the compound of 3-[2-(3-tert-Butyl-ureido)-3,3-dimethyl-butyryl]-6,6-diMethyl-3-aza-bicyclo [3.1.0]hexane-2-carboxylic acid (2-carbamoyl-1-cyclobutylmethyl-2-oxo-ethyl)-amide (the compound of Formula B), with a -20° C. stream of heptane wherein the solution stream is provided under conditions yielding a Reynolds number of 10650, the heptane stream is supplied under conditions yielding a Reynolds number of 23,650 and the solution stream is combined at substantially a 90 degree angle to the anti-solvent stream, thereby providing a slurry comprising precipitated particles of the compound of Formula B, collecting said slurry and distilling supernatant liquid from the collected slurry at subatmospheric pressure and at a temperature that forms an agglomerated particulate having a softening point of greater than about 25° C., and the compound of Formula B has the following structural formula:

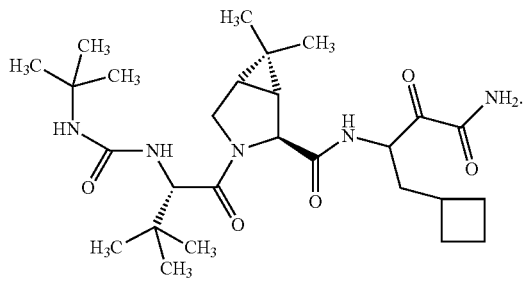

2. A capsule comprising the granular pharmaceutical formulation of claim 1, having on average the following dissolution profile when tested using a USPII dissolution testing apparatus Paddle Stirrer filled with 900 mL of dissolution medium consisting of 0.5% sodium lauryl sulfate solution buffered with pH 6.8 sodium phosphate buffer at 37° C. and with the paddles set at 50 RPM :

| Post DropTime: | % API Dissolved |
|---|---|
| 10 minutes | 80 |
| 20 minutes | 90 |
| 30 minutes | 93 |
| 45 minutes | 96 |
| 60 minutes | 98. |

3. A dosage form comprising an amount of the granular pharmaceutical formulation of claim 1 containing 800 mg of API which dosage form provides a Cmax of 2106 ng/ml at about 3.0 hours and an AUC of 7029 ng.hr/ml when administered to a human.

4. A dosage form comprising an amount of the granular pharmaceutical formulation of claim 1 containing 800 mg of API which dosage form does not prolong the QT interval relative to a placebo when administered to a human.

* * * * *